(12) United States Patent
Sharma et al.

(10) Patent No.: US 10,702,213 B2
(45) Date of Patent: Jul. 7, 2020

(54) DIFFERENTIATION OF HEART FAILURE RISK SCORES FOR HEART FAILURE MONITORING

(71) Applicant: Medtronic, Inc., Minneapolis, MN (US)

(72) Inventors: Vinod Sharma, Maple Grove, MN (US); Joel R. Lauer, Clearwater, MN (US); Holly S. Norman, Chisago City, MN (US)

(73) Assignee: Medtronics, Inc., Minneapolis, MN (US)

( * ) Notice: Subject to any disclaimer, the term of this patent is extended or adjusted under 35 U.S.C. 154(b) by 177 days.

(21) Appl. No.: 15/963,448

(22) Filed: Apr. 26, 2018

(65) Prior Publication Data

US 2019/0125273 A1    May 2, 2019

Related U.S. Application Data

(60) Provisional application No. 62/554,523, filed on Sep. 5, 2017.

(51) Int. Cl.
*A61B 5/00* (2006.01)
*A61B 5/053* (2006.01)
(Continued)

(52) U.S. Cl.
CPC .......... *A61B 5/7275* (2013.01); *A61B 5/0004* (2013.01); *A61B 5/0022* (2013.01);
(Continued)

(58) Field of Classification Search
CPC ... A61B 5/7275; A61B 5/4842; A61B 5/4878; A61B 5/0022; A61B 5/7264;
(Continued)

(56) References Cited

U.S. PATENT DOCUMENTS

| 4,374,382 A | 2/1983 | Markowitz |
| 5,117,824 A | 6/1992 | Keimel et al. |

(Continued)

FOREIGN PATENT DOCUMENTS

| WO | WO 2011/126823 A1 | 10/2011 |
| WO | 2013022760 A1 | 2/2013 |

OTHER PUBLICATIONS

International Search Report and Written Opinion of International Application No. PCT/US2018/049337, dated Nov. 30, 2018, 17 pp.

*Primary Examiner* — Scott M. Getzow

(57) ABSTRACT

A method and device for differentiating heart failure risk scores that includes determining receipt of a current data transmission and acquiring patient metrics from a remote monitoring device, determining a daily heart failure risk score for each day occurring during a time period from a previous received data transmission to the current received data transmission based on the acquired patient metrics, and determining a maximum daily heart failure risk score of the determined daily heart failure risk scores during a lookback window prior to the current received data transmission. A heart failure risk score is determined for the received data transmission based on the determined maximum daily heart failure risk score, and a heart failure risk score alert is determined for the received data transmission based on the proximity of the determined maximum heart failure risk score and the current received data transmission. A display of at least one of the determined heart failure risk score and the determined heart failure risk score alert is generated, and the determined daily heart failure risk score for each day occurring during the time period and the generated display are stored.

24 Claims, 22 Drawing Sheets

(51) Int. Cl.
*A61B 5/0402* (2006.01)
*A61N 1/37* (2006.01)
*A61N 1/372* (2006.01)
*G16H 50/30* (2018.01)
*A61B 5/046* (2006.01)

(52) U.S. Cl.
CPC .......... *A61B 5/0031* (2013.01); *A61B 5/0402* (2013.01); *A61B 5/053* (2013.01); *A61B 5/4878* (2013.01); *A61B 5/686* (2013.01); *A61B 5/7264* (2013.01); *A61B 5/7282* (2013.01); *A61B 5/746* (2013.01); *A61N 1/3702* (2013.01); *A61B 5/046* (2013.01); *A61B 5/0537* (2013.01); *A61N 1/37258* (2013.01); *G16H 50/30* (2018.01)

(58) Field of Classification Search
CPC ..... A61B 5/686; A61B 5/7282; A61B 5/0004; A61B 5/053; A61B 5/746; A61B 5/0402; A61B 5/0031; A61B 5/0537; A61B 5/046; A61N 1/3702; A61N 1/37258; G16H 50/30; G16H 40/63
See application file for complete search history.

(56) References Cited

U.S. PATENT DOCUMENTS

| | | |
|---|---|---|
| 5,545,186 A | 8/1996 | Olson et al. |
| 5,755,736 A | 5/1998 | Gillberg et al. |
| 2010/0152802 A1 | 1/2010 | Min |
| 2010/0030292 A1 | 2/2010 | Sarkar et al. |
| 2012/0253207 A1 | 10/2012 | Sarkar et al. |
| 2016/0206250 A1 | 7/2016 | Sharma et al. |
| 2016/0361026 A1 | 12/2016 | Sarkar et al. |

DIFFERENTIATION OF HEART FAILURE RISK SCORES FOR HEART FAILURE MONITORING

RELATED APPLICATION

This application claims the benefit of U.S. Provisional Patent Application 62/554,523 entitled "Differentiation of Heart Failure Risk Scores for Heart Failure Monitoring" and filed on Sep. 5, 2017, which is incorporated herein by reference in its entirety.

TECHNICAL FIELD

The disclosure relates to medical devices, and, more particularly, to medical devices that monitor cardiac health of a patient.

BACKGROUND

Chronic heart failure (HF) occurs when a heart is unable to consistently pump blood at an adequate rate in response to the filling pressure. To improve the ability of the heart to pump blood, congestive heart failure patients, classified as having New York Heart Association (NYHA) class status of II to IV HF, may require therapy, such as may be provided by implantable medical devices (IMDs) such as implantable cardioverter defibrillators (ICDs) and cardiac resynchronization devices with defibrillation capability (CRT-Ds). Despite using IMDs to improve heart function, some HF patients may require hospitalization. Global health care systems incur billions of dollars each year due to heart failure hospitalizations (HFHs). Identifying patients at risk of HFH to enable timely intervention and prevent expensive hospitalization remains a challenge.

IMDs may be configured to acquire data for a variety of diagnostic metrics that change with HF status and collectively have the potential to signal an increasing risk of HFH. Diagnostic parameter data collected by IMDs include activity, day and night heart rate (NHR), atrial tachycardia/atrial fibrillation (AT/AF) burden, mean rate during AT/AF, percent CRT pacing, number of shocks, and intrathoracic impedance. Additionally, preset or programmable thresholds for diagnostic metrics, when crossed, trigger a notification, referred to as device observation. Each device observation is recorded in an IMD report.

One conventional method for determining heart failure risk status is described in U.S. Publication No. 2012/0253207 A1, entitled "Heart Failure Monitoring," by Sarkar et al., which is incorporated herein by reference in its entirety. In this example, the "High" risk level is associated with 15% or greater risk that the patient will be hospitalized. The "Low" category was chosen to represent diagnostic evaluations where the metric state for all the patient metrics was mostly "Low" (e.g., a risk score of less than ~5%). The "Medium" category comprises of all other metric state combinations that did not get classified as either "High" or "Low." In some cases, a clinician may need to evaluate and respond to numerous high and medium risk level alerts.

SUMMARY

In general, this disclosure describes techniques for enabling alerts generated by the external monitoring device to be further differentiated as being either high/medium alerts or high/medium ongoing alerts, and, in some examples, by enabling further differentiation of an identified current heart failure risk status as high, high new, medium and medium new. Such additional heart failure risk status differentiation of the present disclosure may assist in prioritization of patients, determining patient conditions, assessing the effectiveness of a current therapy, and determining whether therapy adjustments may be necessary. For example, during monitoring of patients, knowing whether an event is an ongoing event, not an ongoing event, a new event, or not a new event enables more efficient prioritization and treatment of patients by the clinician.

In one example, the disclosure describes a method of differentiating heart failure risk status in a heart failure monitoring device that comprises receiving, at the monitoring device, a current data transmission from a remote monitoring device; acquiring patient metrics from the remote monitoring device; determining a daily heart failure risk score for each day occurring during a time period from a previous received data transmission to the current received data transmission based on the acquired patient metrics; determining a maximum daily heart failure risk score of the determined daily heart failure risk scores during a lookback window prior to the current received data transmission; determining a heart failure risk score for the received data transmission based on the determined maximum daily heart failure risk score; determining a heart failure risk score alert for the received data transmission based on the proximity of the determined maximum heart failure risk score and the current received data transmission; and generating a display of at least one of the determined heart failure risk score and the determined heart failure risk score alert.

In another example, the disclosure describes monitoring device for differentiating heart failure risk scores of a patient that comprises an input/output device to receive a current data transmission and acquire patient metrics from a remote monitoring device; and one or more processors configured to: determine a daily heart failure risk score for each day occurring during a time period from a previous received data transmission to the current received data transmission based on the acquired patient metrics; determine a maximum daily heart failure risk score of the determined daily heart failure risk scores during a lookback window prior to the current received data transmission; determine a heart failure risk status for the received data transmission based on the determined maximum daily heart failure risk score; determine a heart failure risk status alert for the received data transmission based on the temporal proximity of the determined maximum heart failure risk score and the current received data transmission; and generate a display of at least one of the determined heart failure risk score and the determined heart failure risk score alert to be output by the input/output device.

In another example, the disclosure describes a heart failure monitoring system that comprises a remote monitoring device to monitor heart failure patient metrics of a patient; and a monitoring device to differentiate heart failure risk scores of the patient, comprising: an input/output device to receive a current data transmission and acquire patient metrics from the remote monitoring device; and one or more processors configured to: determine a daily heart failure risk score for each day occurring during a time period from a previous received data transmission to the current received data transmission based on the acquired patient metrics; determine a maximum daily heart failure risk score of the determined daily heart failure risk scores during a lookback window prior to the current received data transmission; determine a heart failure risk score for the received data transmission based on the determined maximum daily heart failure risk score; determine a heart failure risk score alert for the received data transmission based on the proximity of the determined maximum heart failure risk score and the current received data transmission; and generate a display of at least one of the determined heart failure risk score and the determined heart failure risk score alert to be output by the input/output device.

The details of one or more examples are set forth in the accompanying drawings and the description below. Other features, objects, and advantages will be apparent from the description and drawings, and from the claims.

DETAILED DESCRIPTION

Figure 1:
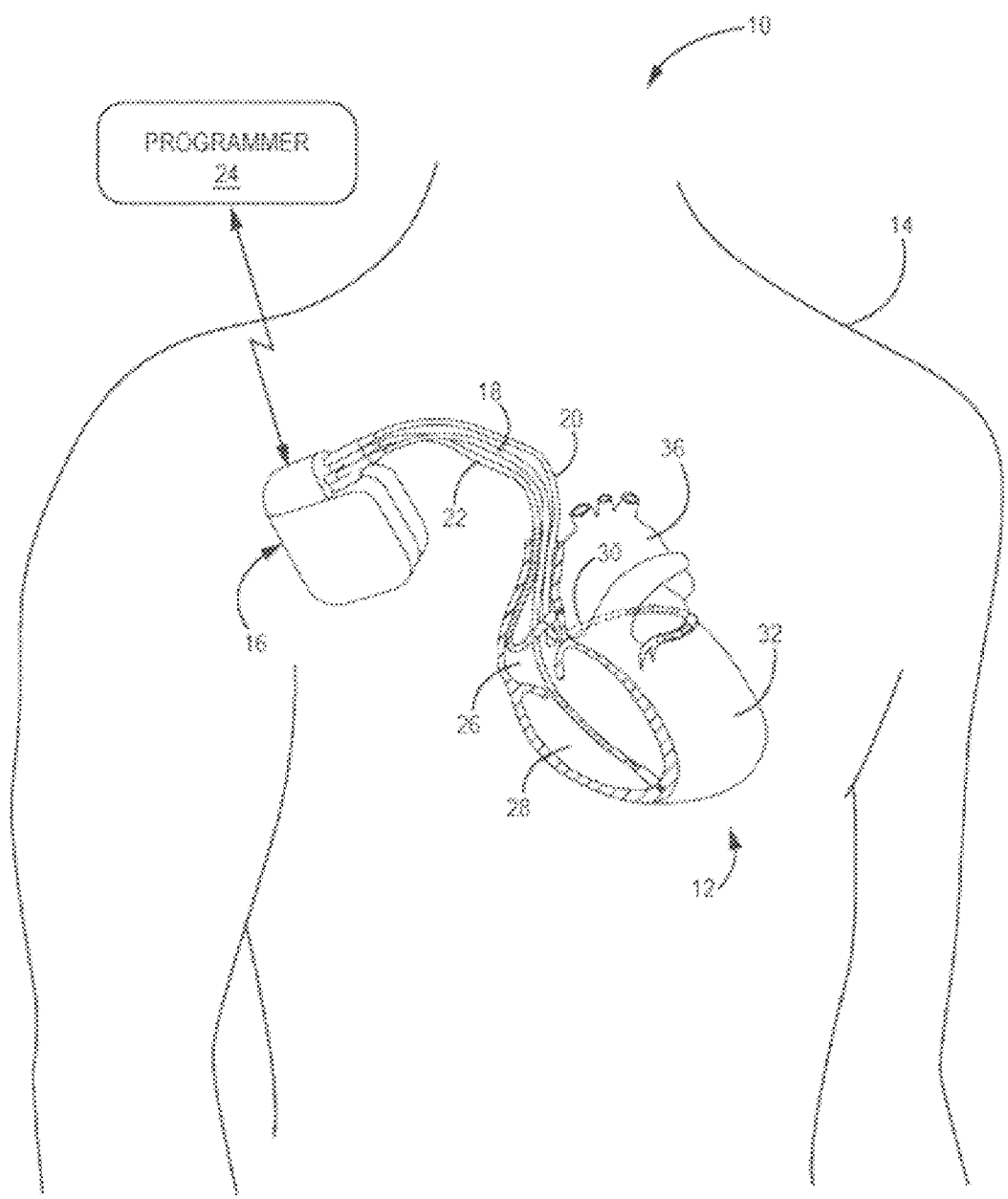
FIG. 1 is a conceptual drawing illustrating an example system configured to transmit diagnostic information indicative of heart failure that includes an implantable medical device (IMD) coupled to implantable medical leads.

This disclosure describes techniques for acquiring and utilizing diagnostic information or patient metrics by an external monitoring device, such as a server, from a remote monitoring device, such as an implantable medical device (IMD), to differentiate between heart failure risk levels. Congestive heart failure may occur gradually over time due to heart disease, patient inactivity, cardiac arrhythmias, hypertension, and other conditions. Often, however, a relatively rapid worsening of the patient's condition, e.g., a decompensation, precipitates hospitalization and, in some cases, death.

One or more implantable medical devices (IMDs) or external medical devices (described hereinafter with respect to a single IMD, although any example herein may be performed by a system including any number of implantable or external medical devices), e.g., a pacemaker, cardioverter and/or defibrillator, or a monitoring device that does not provide therapy, may automatically generate and store patient data regarding patient metrics. The patient metrics may include, as examples, therapy use statistics (e.g., pacing or shocks), thoracic impedance, heart rate, heart rate variability, patient activity, and a percentage of time receiving cardiac resynchronization therapy. Other example patient metrics include weight, blood pressure, respiration rate, sleep apnea burden (which may be derived from respiration rate), temperature, ischemia burden, the occurrence, frequency or duration cardiac events, and sensed cardiac intervals (e.g., heart rate or Q-T intervals). Examples of cardiac events may include atrial and ventricular tachyarrhythmias. Another example patient metric is the ventricular rate during atrial fibrillation. The concentration or levels of various substances, such as blood glucose, hematocrit, troponin and/or brain natriuretic peptide (BNP) levels, within the patient may also be used as one or more patient metrics.

The IMD may provide diagnostic information to one or more users via one or more devices, such as IMD programmers or other computing devices. The diagnostic information may be related to, generated from, or may even include the one or more patient metrics. The diagnostic information may include, as examples, values of the patient metrics and raw data used to derive the values of the patient metrics.

An external monitoring device, such as a server or other computing device, acquires and utilizes the patient metrics associated with diagnostic information from the IMD, and uses the patient metrics to generate heart failure risk scores and differentiate between heart failure risk score alerts. For example, the external monitoring device may receive a transmission of patient metric data for a number of periods, e.g., days, from the IMD, and may generate a periodic heart failure risk score (HFRS) for the periods based on the diagnostic data for the period. The external monitoring device may also differentiate the HFRS based on the maximum periodic HFRS within a lookback window prior to the current period. For example, the external monitoring device may differentiate the alerts as being either high alerts, high ongoing alerts, medium alerts and medium ongoing alerts. In some examples, the external monitoring device may differentiate heart failure risk score ("HFRS") status as being high HFRS, a high new HFRS, a medium HFRS and a medium new HFRS.

Such additional HFRS differentiation of the present disclosure may assist in prioritization of patients, determining patient conditions, assessing the effectiveness of a current therapy, and determining whether therapy adjustments may be necessary. For example, during monitoring of patients, knowing whether an event is an ongoing event, not an ongoing event, a new event, or not a new event enables more efficient prioritization and treatment of patients by the clinician.

FIG. 1 is a conceptual drawing illustrating an example system 10 configured to transmit diagnostic information indicative of heart failure of patient 14. In the example of FIG. 1, system 10 includes IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

In the example of FIG. 1, leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use this impedance to create a fluid index. As the fluid index increases, more fluid is being retained within patient 14 and heart 12 may be stressed to keep up with moving the greater amount of fluid. Therefore, this fluid index may be a patient metric transmitted in higher resolution diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Patent Publication No. 2010/0030292 to Sarkar et al., entitled, "DETECTING WORSENING HEART FAILURE BASED ON IMPEDANCE MEASUREMENTS," which published on Feb. 4, 2010 and is incorporated herein by reference in its entirety.

IMD 16 may also communicate with external programmer 24. In some examples, programmer 24 comprises an external device, e.g., a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to send an interrogation request and retrieve patient metrics or other diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding patient metric data and/or the heart failure risk level. Although programmer 24 may retrieve this information after submitting an interrogation request, IMD 16 may push or transmit the heart failure risk level, for example, if the heart failure risk level indicates a change in patient treatment is necessary. For example, the risk level may be determined based on a predetermined number of patient metrics exceeding their representative thresholds or a weighted score for each of the patient metrics for exceeding one or more thresholds. Additionally or alternatively, the risk level may be determined by a Bayesian Belief Network, or other probability technique, using the values or stratified states of each automatically detected patient metric.

Although IMD 16 may generate the heart failure risk level, IMD 16 may transmit the patient metric data and programmer 24 may generate the heart failure risk level in other examples. Programmer 24 may present an alert to the user with the higher or lower resolution diagnostic information, e.g., the heart failure risk level and/or other patient metric data. The patient metric data may include intracardiac or intravascular pressure, activity, posture, respiration, or thoracic impedance.

As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts, or other higher or lower resolution diagnostic information, to facilitate immediate notification of the heart failure condition.

Programmer 24 may also allow the user to define how IMD 16 senses, detects, and manages each of the patient metrics. For example, the user may define the frequency of sampling or the evaluation window used to monitor the patient metrics. In addition, the user may use programmer 24 to set each metric threshold used to monitor the status of each patient metric. The metric thresholds may be used to determine when each of the patient metrics has reached a magnitude indicative of being at risk for heart failure. In some examples, when a patient metric exceeds its respective metric threshold, the metric may be counted in the predetermined number used to create the HFRS, which may be presented as a risk level. For example, if two of the eight patient metrics exceed their thresholds, the heart failure risk level may be described as a high risk level for patient 14 to be hospitalized within thirty days. This heart failure risk level may indicate that patient 14 is at an increased risk of heart failure if the predetermined number of patient metrics exceeding their respective thresholds is one or more.

The risk level may be a predetermined number that is set to different values for patients of differing age, weight, cardiac condition, or any number of other risk factors. In other examples, the predetermined number may be set to a different number or a risk level percentage (fraction). In this manner, the predetermined number may represent a preset fraction of unweighted or weighted metrics exceeding a threshold with respect to the total number of monitored metrics. Programmer 24 may be used to set this predetermined number or any other factors used to generate and interpret the heart failure risk level.

In other examples, the risk level may be determined by the sum, average, or other combination of weighted scores for each of the patient metrics. Each patient metric may have one or more metric-specific thresholds that stratify the state of the metric. Since some states or metrics may be more indicative of the risk of re-hospitalization, these states and/or metrics may provide a greater contribution to the determined risk level. For example, a high risk state for intrathoracic impedance may have a weighted score that is double that of a high risk state for patient inactivity. In other words, intrathoracic impedance may be a greater risk factor to the patient than patient inactivity. Alternatively, a probability analysis may be performed on some or all of the patient metrics to determine the probability that patient 14 will be re-hospitalized for heart failure. For example, a Bayesian Belief Network may be applied to the values of the patient metrics to determine the risk level, e.g., the probability, that patient 14 will be re-admitted to the hospital for heart failure.

In some examples, one or more patient metrics may be collected or detected outside of IMD 16. Patient metrics collected outside of IMD 16 may be referred to as "non-device metrics." These non-device metrics may be useful for some patients in determining the heart failure risk level before hospitalization, during hospitalization, and/or during the post-hospitalization period. These non-device metrics may be collected, e.g., received via patient input or electronic transmission from another device, and may be analyzed similar to any other patient metrics described herein. Example non-device metrics may include patient weight, medication compliance, consumed food, liquid intake, activity durations, pain levels, pain locations, urinary or fecal voiding events, or any other non-device metrics that may describe or otherwise characterize the health of patient 14.

IMD 16 and programmer 24 may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

As described herein, IMD 16 automatically detects a plurality of patient metrics from patient 14. These patient metrics may alone, or in combination, be indicative of heart failure of patient 14. The patient metrics may include, as examples, thoracic impedance, heart rate variability, the number, frequency or duration of atrial fibrillation after cardioversion therapy, ventricular rate during persistent atrial fibrillation, night heart rate, or any other metrics detectable from patient 14 or based on the treatment of patient 14.

As one example, the heart failure risk level may indicate a high risk of hospitalization when a predetermined number of the plurality of automatically detected patient metrics, such as two or more automatically detected patient metrics, each exceed their respective metric-specific threshold. As another example, the heart failure risk level may indicate a medium risk of hospitalization when a predetermined number of the plurality of automatically detected patient metrics, such as only one automatically detected patient metric, exceeds its respective metric-specific threshold. In an additional example, the heart failure risk level may indicate a low risk of hospitalization when none of the plurality of automatically detected patient metrics exceeds their respective metric-specific thresholds.

IMD 16 may automatically detect each of the patient metrics and store them within the IMD for later transmission. Although IMD 16 may automatically detect eight different patient metrics in some examples, IMD 16 may detect more or less patient metrics in other examples. For example, the patient metrics may include two or more of a thoracic fluid index, an atrial fibrillation duration, a ventricular contraction rate during atrial fibrillation, a patient activity, a nighttime heart rate, a heart rate variability, a cardiac resynchronization therapy (CRT) percentage (e.g., the percentage of cardiac cycles for which cardiac resynchronization pacing was provided), or the occurrence of or number of therapeutic electrical shocks. The metric-specific thresholds may include at least two of a thoracic fluid index threshold of approximately 60, an atrial fibrillation duration threshold of approximately 6 hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, or an electrical shock threshold of 1 electrical shock. In other examples, each of the metric-specific thresholds may have various different values determined by the clinician, based on previous data from other patients, or determined based on a healthy state of patient 14. Alternatively, the metric-specific thresholds may be rate of change thresholds or relative change thresholds, e.g., a heart rate variability that is decreasing faster than a predetermined rate, or a predetermined amount or percentage less than a recently identified variability value.

In other examples, the heart failure risk level may be determined with probability models that determine the probability of hospitalization based on the values of all patient metrics. In this manner, each of the patient metric values may contribute to the risk level regardless of whether a metric-specific threshold is exceeded. For example, IMD 16 may generate a heart failure risk level with a Bayesian Belief Network based on the plurality of automatically generated patient metrics. The risk level may include general levels, e.g., a high risk, medium risk, or low risk of hospitalization, or numerical indications, e.g., a percent probability that patient 14 will be hospitalized.

Figure 2A:
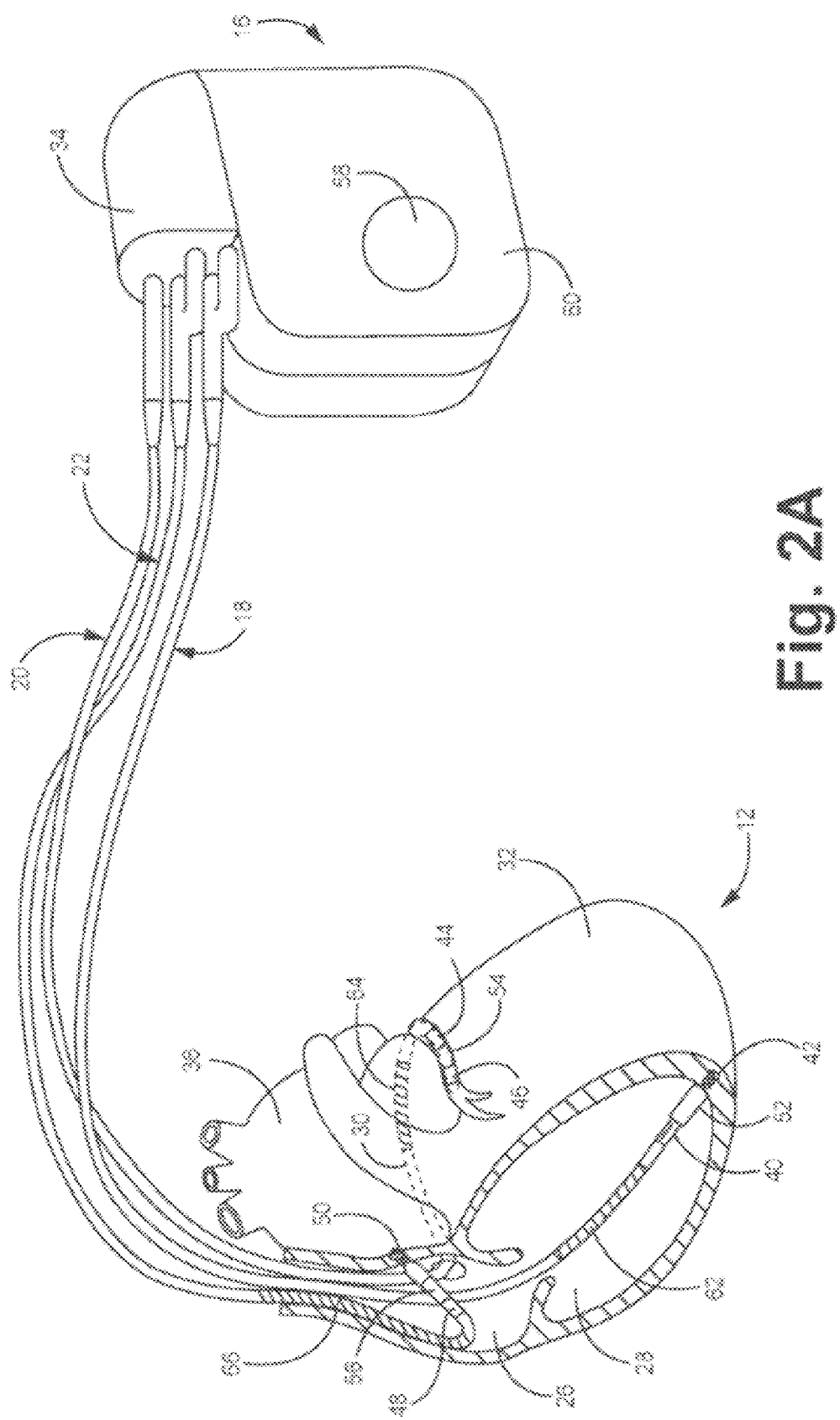
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12. Further, external electrodes or other sensors may be used by IMD 16 to deliver therapy to patient 14 and/or sense and detect patient metrics used to generate the high and lower resolution diagnostic information, e.g., a heart failure risk level.

Figure 2B:
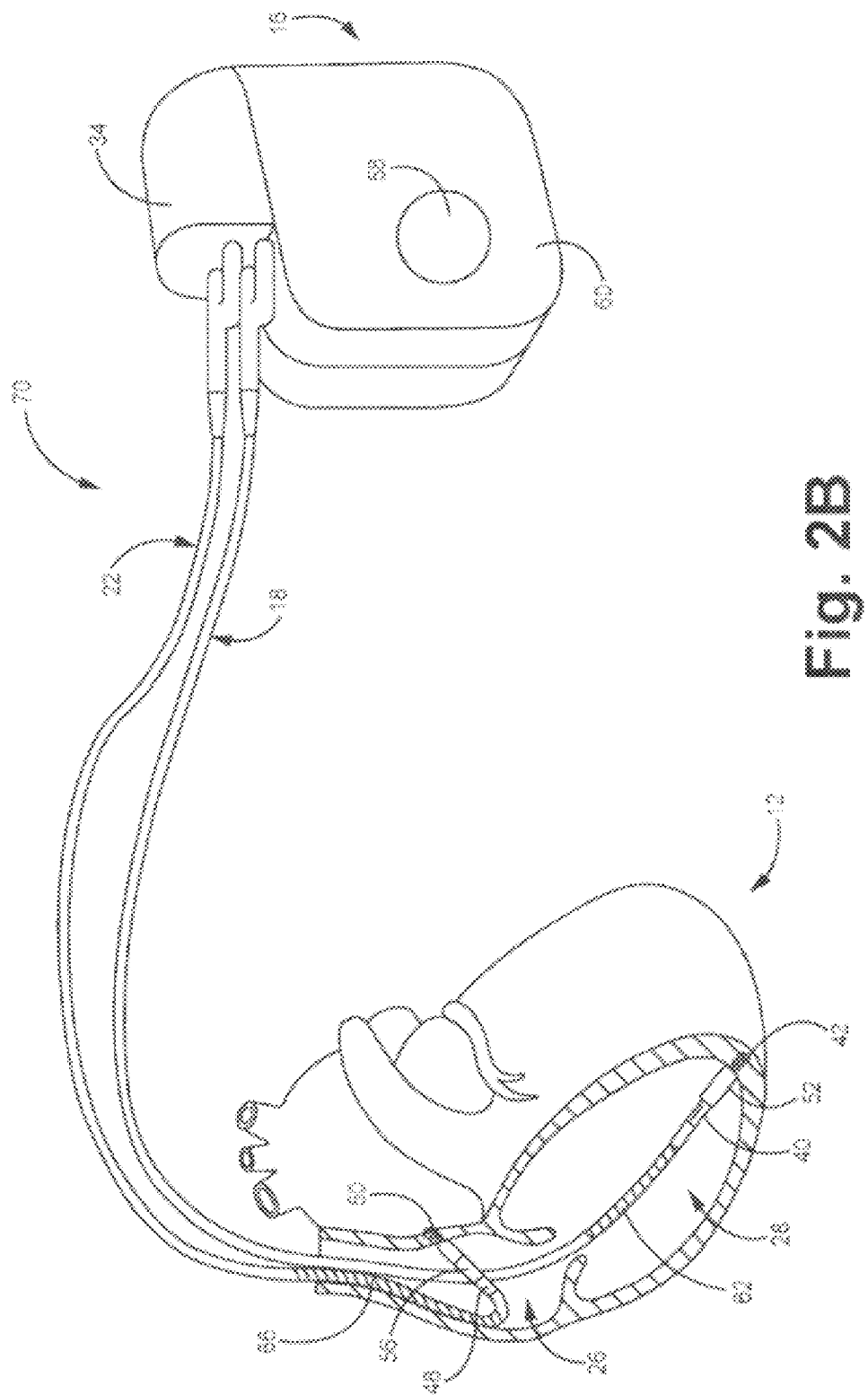
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, systems in accordance with this disclosure may include three transvenous leads located as illustrated in FIGS. 1 and 2, and an additional lead located within or proximate to left atrium 36. As another example, systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

In some examples, a system may additionally or alternatively include one more subcutaneous pacing and/or defibrillation devices coupled to extravascular leads, leadless pacing devices configured for implantation within a heart chamber, and/or implantable or external monitoring devices that monitor patient parameters but do not provide therapy.

Any of electrodes 40, 42, 44, 46, 48, 50, 62, 64, 66, and 58 may be utilized by IMD 16 to sense or detect patient metrics used to generate the heart failure risk level for patient 14. Typically, IMD 16 may detect and collect patient metrics from those electrode vectors used to treat patient 14. For example, IMD 16 may derive an atrial fibrillation duration, heart rate, and heart rate variability metrics from electrograms generated to deliver pacing therapy. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. This intrathoracic impedance may be used to generate a fluid index patient metric that indicates the amount of fluid building up within patient 14. Since a greater amount of fluid may indicate increased pumping loads on heart 12, the fluid index may be used as an indicator of heart failure risk. IMD 16 may periodically measure the intrathoracic impedance to identify a trend in the fluid index over days, weeks, months, and even years of patient monitoring.

In general, the two electrodes used to measure the intrathoracic impedance may be located at two different positions within the chest of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection of patient metrics and differentiation of heart failure risk status according to this disclosure may be performed in two lead systems in the manner described herein with respect to three lead systems. In other examples, a system similar to systems 10 and 70 may only include one lead (e.g., any of leads 18, 20 or 22) to deliver therapy and/or sense and detect patient metrics related to monitoring risk of heart failure. Alternatively, diagnostic data may be implemented in systems utilizing subcutaneous leads, subcutaneous IMDs, or external medical devices. Although FIGS. 1-2 provide an exemplary IMD 16 implantation in which the notification differentiation described below may be implemented, it is understood that IMD 16 and it's associated electrodes may be implemented in other locations of the patient's body, and may include leads or may be leadless.

Figure 3:
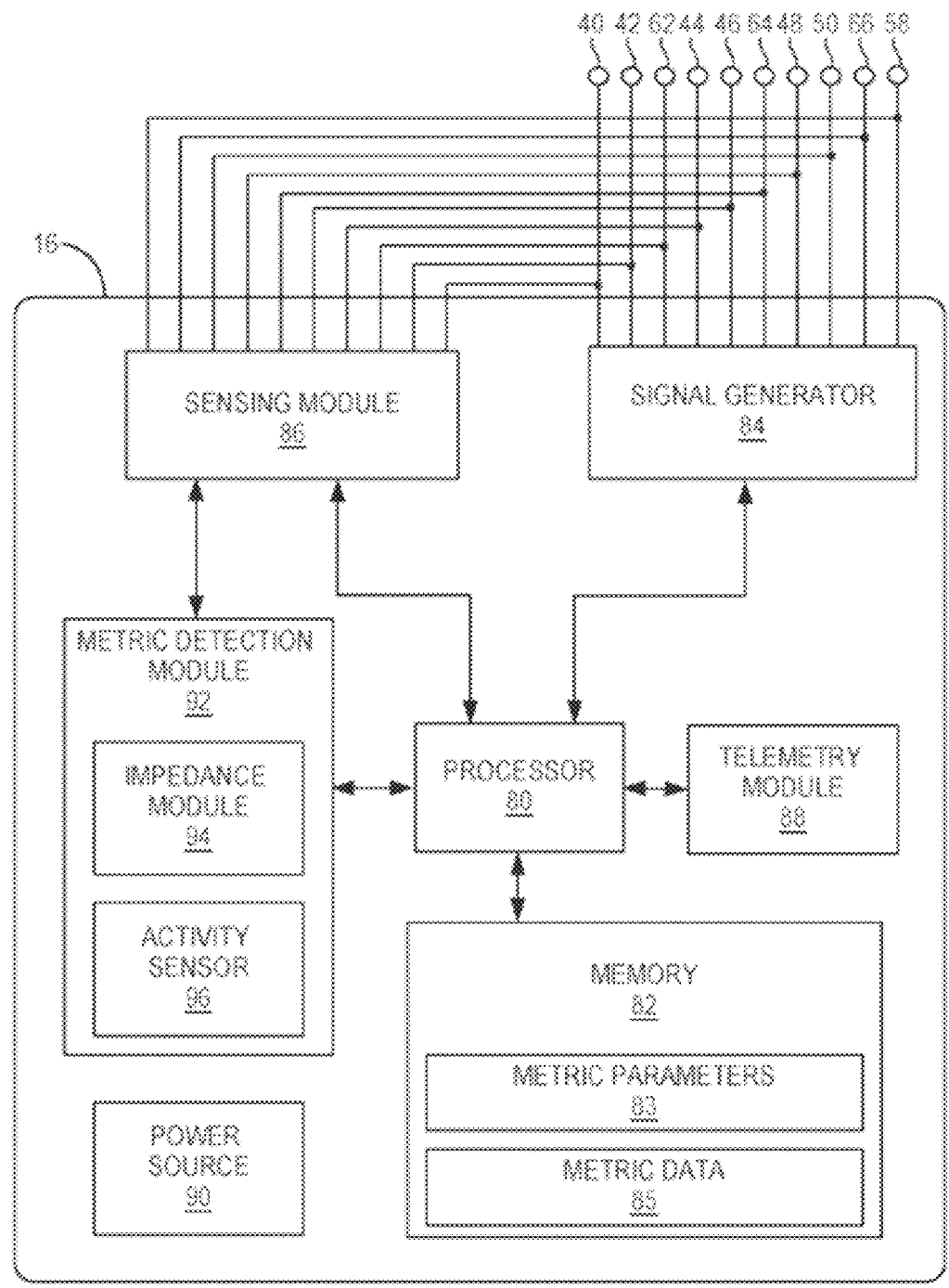
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver therapy to heart 12 according to a therapy parameters and programs which may be stored in memory 82. Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. In the event that processor 80 detects an atrial or ventricular tachyarrhythmia based on signals from sensing module 86, and a cardioversion or defibrillation shock is desired, processor 80 may control the amplitude, form and timing of the shock delivered by signal generator 84.

Memory 82 may be configured to store a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric, the sample rate, calibration schemes, metric-specific thresholds, and any other related information. In one example, the patient metrics for which metric parameters are stored as metric parameters 83 may include a thoracic fluid index (or a thoracic impedance), an atrial tachycardia or fibrillation burden, a ventricular contraction rate during atrial fibrillation, a patient activity, a nighttime heart rate, a difference between night and day heart rate, a heart rate variability, a cardiac resynchronization therapy percentage, a bradyarrhythmia pacing therapy percentage (in a ventricle and/or atrium), and number or frequency of electrical shock events. In other examples, other patient metrics may be stored that may be useful in the detection of heart failure risk, e.g., blood pressure, right ventricular pressure, pulmonary artery pressure, patient temperature, lung volume, lung tidal volume, lung density, breathing rate or even biomarkers such as a brain natriuretic peptide (BNP), troponin, or related surrogates. In such examples, IMD 16 may include or be coupled to sensors known in the art for detecting such metrics. In some examples, the atrial tachycardia or fibrillation burden may be a time of the event, a percent or amount of time over a certain period, a number of episodes, or even a frequency of episodes.

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of approximately 60, an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate. The dynamic storage rate may be higher when processor 80 needs to transmit higher resolution diagnostic information and lower when processor 80 needs to transmit lower resolution diagnostic information. For example, processor 80 may store patient metrics in memory 82 every minute or hour when processor 80 is transmitting higher resolution diagnostic information. However, processor 80 may only store patient metrics in memory 82 once a day, for example, when processor 80 is only transmitting lower resolution diagnostic information that does not necessitate more frequent data. In addition to the dynamic storage rate, the rate at which metric detection module 92 automatically detects each patient metric may be altered to match the dynamic storage rate. In this manner, metric detection module 92 may not waste energy detecting patient metrics if the higher frequency data would just be discarded.

Metric detection module 92 may, for example, transmit lower resolution diagnostic information (e.g., a heart failure risk level) that is based on the patient metrics and whether any of the metrics exceed the respective specific metric thresholds. Any time that an automatically detected patient metric exceeds their respective metric threshold, the patient metric is counted in the risk level. In one example, if two or more of the eight patient metrics exceed their respective metric threshold, then the risk level would be classified as a high risk. In other examples, the risk level may include a numerical value such as 2 out of 8 (e.g., threshold exceeding metrics out of the total number of monitored metrics). The higher the risk level, the more likely that patient 14 is at risk to be admitted to the hospital within a predefined time period, e.g., re-admitted to the hospital within a post-hospitalization period. For example, each threshold exceeding metric counted in the predetermined number may contribute to a higher risk level of heart failure. In this example, a risk level of 1 out of 8 may indicate a medium risk of hospitalization, a risk level of 2 out of 8 may indicate a high level of hospitalization, and a risk level of 3 out of 8 may indicate a very high risk of hospitalization.

It is also noted that exceeding a metric threshold does not require that the detected value of the patient metric becomes greater than the magnitude of the threshold. For some patient metrics, exceeding the metric threshold may occur when the value of the patient metric drops below the metric threshold. Therefore, each threshold may be a boundary that triggers the metric's inclusion in the heart failure risk level any time that the metric threshold is crossed. In other examples, as described above, the risk level may be calculated as a sum of weighted metrics such that some metrics may impact the risk level greater than other metrics (e.g., a trans-thoracic impedance may be weighted double that of other metrics). This use of thresholds for determining the risk levels may be considered heuristic logic.

In this manner, metric detection module 92 may automatically detect each of the patient metrics and store them within metric data 85 for later transmission. Metric detection module 92 may be any type of hardware (e.g., a specialized circuit or processor) or a software module executed by a processor (e.g., processor 80). Metric parameters 83 may generally store one metric-specific threshold per patient metric, but other examples may include several thresholds to apply depending on other patient conditions, delivered therapies, or even the importance of one patient metric. For example, the thoracic fluid index determined from sensed intrathoracic impedance may be subject to two separate metric thresholds each counting towards the predetermined number of the heart failure risk level. The first thoracic fluid index threshold may be set to a value of 60, but the second thoracic fluid index threshold may be set to a value of 100. If the thoracic fluid index metric exceeds the first thoracic fluid index threshold of 60, the fluid index metric may be counted in the heart failure risk level. If the fluid index also crosses the second thoracic fluid index threshold of 100, the fluid index metric may be counted in the heart failure risk level a second time. In this manner, the heart failure risk level may weight more extreme values of some metrics more heavily than other metrics. In one example, the fluid index value may be a unitless number using a recent intrathoracic impedance, a short term mean impedance, an impedance variability value, and a duration value. Example fluid index values and impedance measurements are described in U.S. Patent Application No. 2010/0030292 entitled "DETECTING WORSENING HEART FAILURE BASED ON IMPEDANCE MEASUREMENTS," which is incorporated by reference herein in its entirety. As the intrathoracic impedance remains low, the fluid index may increase. Conversely, as the intrathoracic impedance remains high, the fluid index may decrease. In this manner, the fluid index value maybe a numerical representation of retained fluid that is specific to patient 14. In other examples, the intrathoracic impedance may be alternatively used.

In other examples, a statistical or probability analysis may be performed on some or all of the patient metrics to determine the probability that patient 14 will be re-hospitalized for heart failure. In this manner, the heart failure risk level may be determined without utilizing thresholds for each of the detected patient metrics. Instead, metric detection module 92 or processor 80 may examine the values of each of the patient metrics for relative contributions to the possibility that patient 14 is at a higher risk of being re-hospitalized. For example, a Bayesian Belief Network may use the values of the patient metrics instead of a predetermined threshold to determine the risk level that patient 14 will be re-admitted to the hospital for heart failure. Such a statistical analysis is described in PCT Patent Publication No. WO 2011/126823A1 entitled, "METHOD AND APPARATUS FOR MONITORING TISSUE FLUID CONTENT FOR USE IN AN IMPLANTABLE CARDIAC DEVICE," which is incorporated by reference herein in its entirety.

Metric data 85 is a portion of memory 82 that may store some or all of the patient metric data that is sensed and detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. Processor 80 may access metric data when necessary to retrieve and transmit patient metric data and/or generate heart failure risk levels. In addition, metric data 85 may store heart failure risk levels or other generated information related to the heart failure risk of patient 14. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic information, e.g., risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure score or status or that patient 14 is at risk for hospitalization. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect eight different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of FIG. 1, 2 or 3 to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. The activity patient metric may then be used to generate the heart failure risk level.

In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional sub-modules or sub-routines that detect and monitor other patient metrics used to monitor patient 14 and/or generate the heart failure risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or intrathoracic impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate the heart failure risk level based upon the patient metrics sensed, detected, and stored in metric data 85 of memory 82. For example, processor 80 may continually update the heart failure risk level as metric detection module 92 updates each patient metric. In other examples, processor 80 may periodically update the heart failure risk level according to an updating schedule. Processor 80 may compare each of the automatically detected patient metrics to their respective metric-specific thresholds and automatically generate the heart failure risk level based on the comparison.

Processor 80 may also compare the heart failure risk level to the predetermined number stored in memory 82. The predetermined number may indicate when patient 14 is at an increased risk of heart failure. The predetermined number may be a percentage or a number of patient metrics exceeding the respective metric threshold. At this stage, the risk level may be considered critical. Although a clinician may be presented with the heart failure risk level at any time, processor 80 may push the heart failure risk level to a clinician or other healthcare professional in an alert. This immediacy may be necessary because a critical risk level indicates that heart failure may be imminent in a large number of patients with the same patient metric levels. Therefore, a clinician may receive the transmitted diagnostic information of the critical risk level and initiate alternative treatment to prevent patient 14 from hospitalization.

In some examples, programmer 24, a computing device, or a server may include a metric detection module similar to metric detection module 92 described herein. For example, programmer 24 may generate the risk level based on diagnostic information, including patient metric values, transmitted by IMD 16. However, processor 80 may still collect and store the data for each patient metric or even organize and format the patient metric data before transmitting the patient metrics in metric data 85 to the external device. In addition, processor 80 may transmit the metric thresholds with the patient metric data so that any external device may generate heart failure risk levels specific to patient 14.

As described above, processor 80 may provide an alert to a user, e.g., of programmer 24, regarding the data from any patient metric and/or the heart failure risk level. In one example, processor 80 may provide an alert with the heart failure risk level when programmer 24 or another device communicates with IMD 16. This communication may be in the form of an interrogation request that is sent to IMD 16. In response to the interrogation request, processor 80 may transmit higher resolution diagnostic information if patient 14 is hospitalized or lower resolution diagnostic information if patient 14 is in the post-hospitalization period. In other examples, processor 80 may push an alert to programmer 24 or another device whenever the heart failure risk level becomes critical via transmission by telemetry module 88. Alternatively, IMD 16 may directly indicate to patient 14 that medical treatment is needed due to a critical heart failure risk level. IMD 16 may include a speaker to emit an audible sound through the skin of patient 14 or a vibration module that vibrates to notify patient 14 of needed medical attention. Processor 80 may choose this action, for example, if the alert cannot be sent because of no available connection.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data (higher or lower resolution diagnostic information) to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data in the form of higher resolution diagnostic information or heart failure risk level in the form of lower resolution diagnostic information, to the user. IMD 16 may spontaneously transmit the diagnostic information to the network or in response to an interrogation request from a user. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device. Patient metrics may, in some examples, be compared to means, medians, or outliers from other patients to determine when the patient is at a high risk of hospitalization for heart failure. If one of the automatically detected patient metrics exceeds its respective metric-specific threshold, processor 80 may control telemetry module to transmit that patient metric and possibly other patient metrics to allow the clinician to more accurately diagnose the problem with patient 14.

Figure 4:
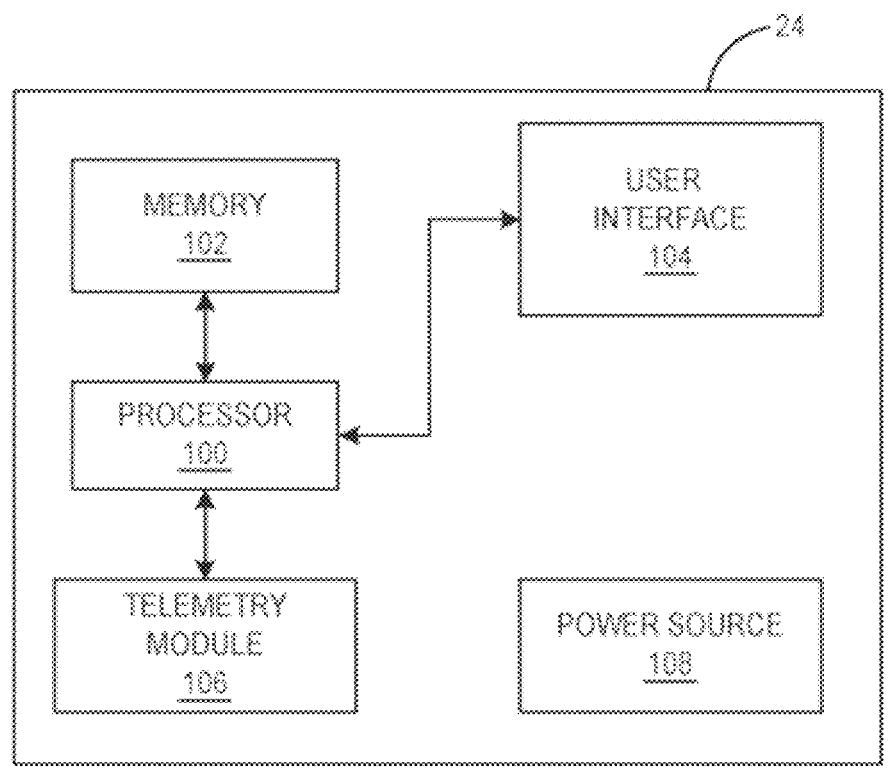
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure the operational parameters of and retrieve data from IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the heart failure risk level and/or patient metrics via programmer 24. In other words, programmer 24 may receive higher or lower resolution diagnostic information from IMD 16.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may transmit an interrogation request to telemetry module 88 of IMD 16. Accordingly, telemetry module 106 may automatically receive diagnostic information, may receive diagnostic information selected by the request, or may receive diagnostic information based on already entered patient status to IMD 16. The diagnostic information may include patient metric values or other detailed information from telemetry module 88 of IMD 16. The diagnostic information may include an alert or notification of the heart failure risk level from telemetry module 88 of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment for the potential heart failure condition that may require re-hospitalization is left untreated. In response to receiving the alert, user interface 104 may present the alert to the healthcare professional regarding the risk level or present an instruction to patient 14 to seek medical treatment.

Either in response to pushed heart failure information, e.g., the risk level or patient metrics, or requested heart failure information, user interface 104 may present the patient metrics and/or the heart failure risk level to the user. In some examples, user interface 104 may also highlight each of the patient metrics that have exceeded the respective one of the plurality of metric-specific thresholds. In this manner, the user may quickly review those patient metrics that have contributed to the identified heart failure risk level.

Upon receiving the alert via user interface 104, the user may also interact with user interface 104 to cancel the alert, forward the alert, retrieve data regarding the heart failure risk level (e.g., patient metric data), modify the metric-specific thresholds used to determine the risk level, or conduct any other action related to the treatment of patient 14. In some examples, the clinician may be able to review raw data (e.g., higher resolution diagnostic information) to diagnose any other problems with patient 14 or monitor the efficacy of treatments given to patient 14. For example, the clinician may check if the intrathoracic impedance has increased after diuretic therapy or if the heart rate has decreased during atrial fibrillation in response to a rate controlling drug. User interface 104 may even suggest treatment along with the alert, e.g., certain drugs and doses, to minimize symptoms and tissue damage that could result from heart failure. User interface 104 may also allow the user to specify the type and timing of alerts based upon the severity or criticality of the heart failure risk level. In addition to the heart failure risk level, in other examples, user interface 104 may also provide the underlying patient metrics to allow the clinician to monitor therapy efficacy and remaining patient conditions.

In some examples, processor 100 of programmer 24 and/or one or more processors of one or more networked computers may perform all or a portion of the techniques described herein with respect to processor 80, metric detection module 92 and IMD 16. For example, processor 100 or a metric detection module 92 within programmer 24 may analyze patient metrics to detect those metrics exceeding thresholds and to generate the heart failure risk level.

Figure 5:
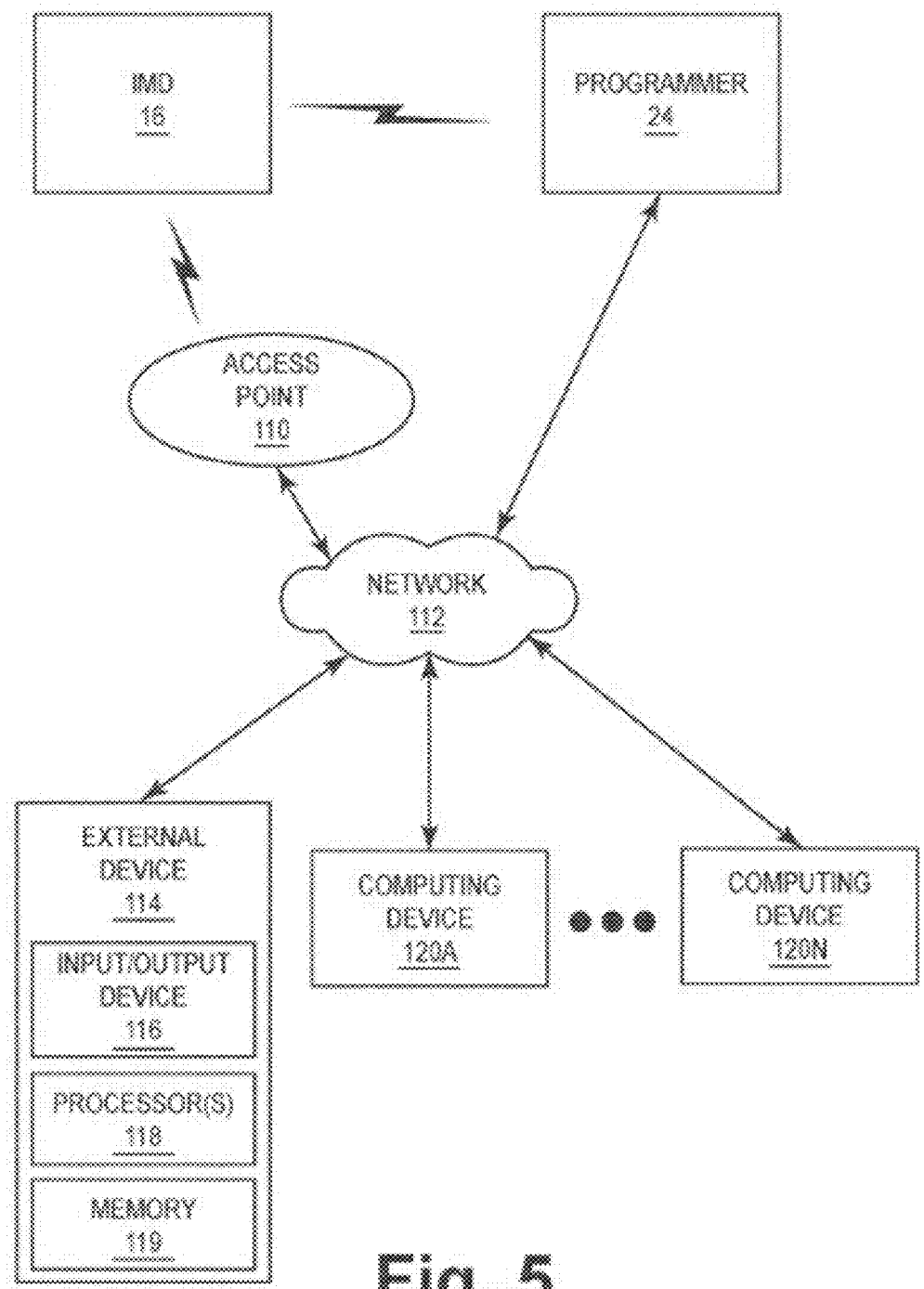
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device 114, such as a server, and one or more computing devices 120A-120N, that are coupled to the IMD 16 and programmer 24 shown in FIG. 1 via a network 112. In the examples of the present disclosure described below, external device 114 acquires and utilizes the patient metrics associated with diagnostic information from the remote implantable monitoring device, such as an IMD 16, and uses the patient metrics to generate heart failure risk scores and differentiate between heart failure risk score alerts. For example, once receipt of a scheduled data transmission from the remote implantable monitoring device is detected, the external monitoring device may acquire patient metrics from the IMD that are used by the external monitoring device to determine an HFRS associated with the data transmission. An HFRS status alert is then generated by the external device based on the temporal proximity of a maximum daily HFRS within a lookback window prior to the current data transmission. For example, the external monitoring device may differentiate the alerts as being either high alerts, high ongoing alerts, medium alerts and medium ongoing alerts. In some examples, the external monitoring device may differentiate heart failure risk score ("HFRS") status as being high HFRS, a high new HFRS, a medium HFRS and a medium new HFRS.

Network 112 may be generally used to transmit diagnostic information (e.g., a risk level) from a remote IMD 16 to another external computing device during a post-hospitalization period. However, network 112 may also be used to transmit diagnostic information from IMD 16 to an external computing device within the hospital so that a clinician or other healthcare professional may monitor patient 14. In this example, IMD 16 may use its telemetry module 88 to communicate with programmer 24 via a first wireless connection, and to communication with an access point 110 via a second wireless connection. In the example of FIG. 5, access point 110, programmer 24, external device 114, and computing devices 120A-120N are interconnected, and able to communicate with each other, through network 112. In some cases, one or more of access point 110, programmer 24, external device 114, and computing devices 120A-120N may be coupled to network 112 through one or more wireless connections. IMD 16, programmer 24, external device 114, and computing devices 120A-120N may each comprise one or more processors, such as one or more microprocessors, DSPs, ASICs, FPGAs, programmable logic circuitry, or the like, that may perform various functions and operations, such as those described herein.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, external device 114 or computing devices 120 may control or perform any of the various functions or operations described herein, e.g., generate a heart failure risk level based on the patient metric comparisons or create patient metrics from the raw metric data.

External device 114 further includes input/output device 116, processor 118 and memory 119. Input/output device 116 includes input devices such as a keyboard, a mouse, voice input etc. and output device includes graphical user interfaces, output displays, printers and other suitable means. Processor 118 includes any suitable processor such as Intel Xeon Phi. Processor 118 is configured to set the start and end dates for each evaluation period. The evaluation period serves as an evaluation window that encompasses data, acquired from each patient, that are within the boundaries (i.e. start and end times). Processor 118 is also configured to perform a variety of calculations. For example, processor 118 calculates risk of HFH for each evaluation period. In one or more embodiments, weighting factors are applied to two or more evaluations periods to determine the risk.

Memory 119 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Exemplary data that may be stored in memory 119 includes heart failure patient data, heart failure prospective risk data etc. Evaluation period start and end times may also be stored in memory 119. Heart failure patient data includes data observations (e.g. data sensed from sensors that cross a threshold). Additionally, evaluation period data is also stored in memory 119. For example, the start and end dates of the evaluation period data is stored in memory 119.

In some cases, external device 114 may be configured to provide a secure storage site for archival of diagnostic information (e.g., patient metric data and/or heart failure risk levels) that has been collected and generated from IMD 16 and/or programmer 24. Network 112 may comprise a local area network, wide area network, or global network, such as the Internet. In some cases, programmer 24 or external device 114 may assemble the diagnostic information in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

In the manner of FIG. 5, computing device 120A or programmer 24, for example, may be remote computing devices that receive and present diagnostic information transmitted from IMDs of multiple patients so that a clinician may prioritize the patients needing treatment immediately. In other words, the clinician may triage patients by analyzing the heart failure risk levels of multiple patients. The computing device may use its communication module to receive the diagnostic information (e.g., heart failure risk levels) transmitted from multiple IMDs via network 112. In this manner, each heart failure risk level is representative of one the patients. Although the IMDs may transmit the diagnostic information at any time, generally the IMDs may transmit diagnostic information on a daily basis or in response to an interrogation request from an external computing device. In other examples, the IMDs may be configured to transmit diagnostic information when the risk level becomes critical or there is a medium or high risk of hospitalization within a predetermined period. A processor within the remote computing device may then automatically rank each of the patients based on each of the heart failure risk levels and the user interface may present the list of ranked patients to the clinician. Generally, the list will start with the most critical patient, e.g., the highest risk level, at the top. This method may be useful for healthcare professionals making house calls, serving patients within a nursing home, or any other circumstance in which a professional treats many patients. The healthcare professionals may thus triage patients in order to minimize any hospitalization due to heart failure.

Figure 6:
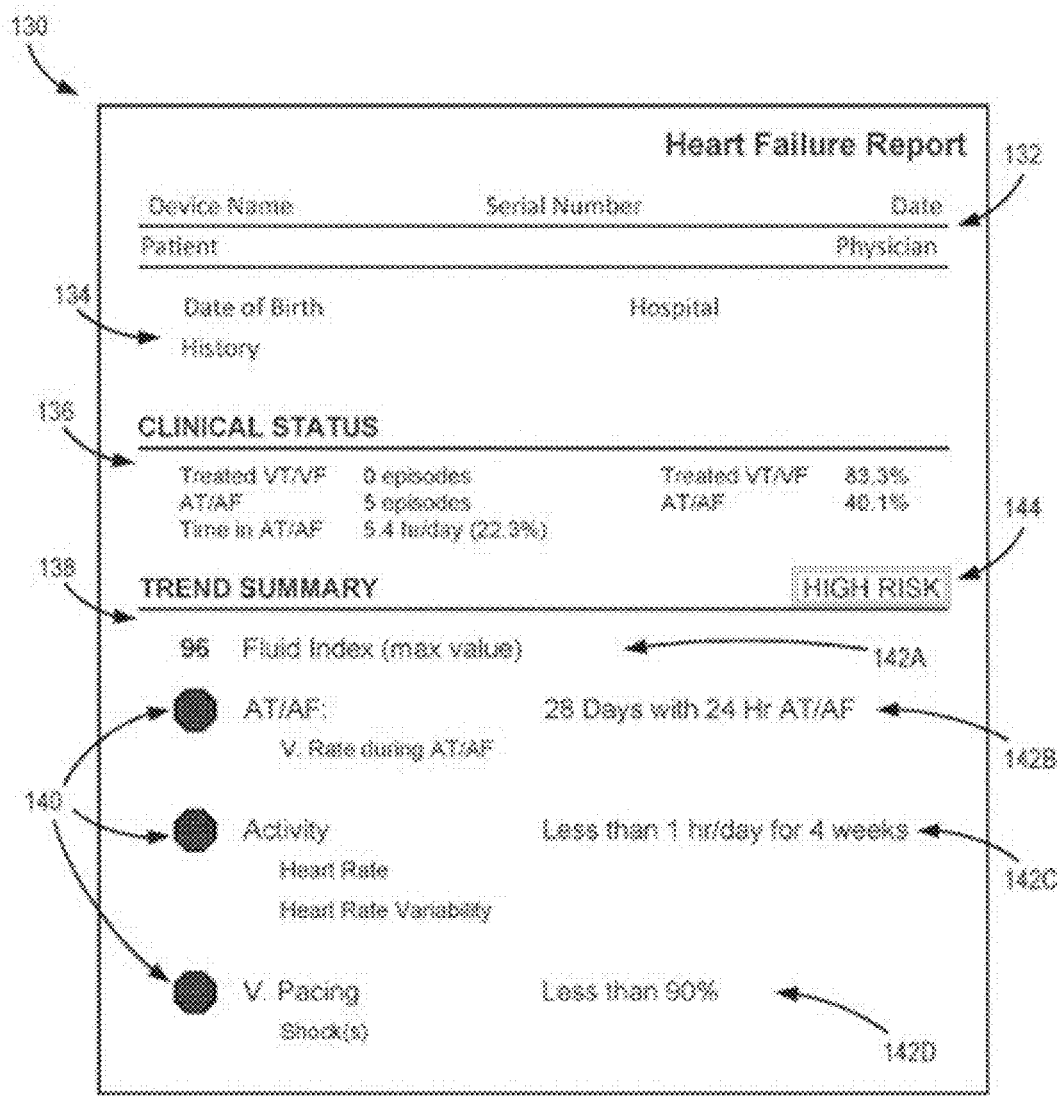
FIG. 6 illustrates an example user interface that includes a heart failure risk score that indicates a risk of the patient for hospitalization due to heart failure.

FIG. 6 illustrates an example screen 130 of user interface 104 that includes lower resolution diagnostic information. As shown in FIG. 6, screen 130 includes risk level 144 that indicates the risk that patient 14 will be hospitalized due to heart failure. Risk level 144 is an example of a periodic HFRS. As described herein, the heart failure risk level may be indicative that patient 14 would be hospitalized. Although screen 130 is described as being presented on user interface 104 of programmer 24, screen 130 may be presented on any user interface of any device used by a healthcare professional. The heart failure report of screen 130 may be transmitted to a user at a scheduled frequency, e.g., once a day or once a week, or in response to an interrogation request from the user. As shown in FIG. 6, screen 130 is a heart failure report that includes identification data 132 and patient history data 134. Identification data 132 includes items such as the patient name, the device name, the serial number of IMD 16, the date, and even the physician name. Patient history data 134 may be relevant data that may help in the treatment of patient 14.

Screen 130 also includes clinical status 136 that includes information regarding the stimulation therapy delivered by IMD 16. Screen 130 also presents trend summary 138. Trend summary 138 presents a snapshot of certain patient metrics that are exceeding their respective metric thresholds to contribute to the severity of heart failure risk level 144. Critical indicator 140 is provided to remind the user that each of the patient metrics with critical indicator 140 is contributing to the heart failure risk level because the metric threshold has been met or exceeded. In examples in which risk level 144 is determined with a statistical analysis, critical indicator 140 may not be necessary. However, certain patient metrics that contribute significantly to the probability that patient 14 may be re-hospitalized may still be presented to the user.

In the example of FIG. 6, trend summary 138 presents four patient metrics 142A, 142B, 142C, and 142D (collectively "patient metrics 142"). Thoracic fluid index metric 142A indicates a maximum detected value of 96. Although thoracic fluid index metric 142A is not contributing to risk level 144 in this example, it is provided because it is an important indicator of thoracic fluid volume and potential heart failure. Atrial fibrillation duration 142B indicates that patient 14 has had 28 days of atrial fibrillation or atrial tachycardia for 24 hours. Activity metric 142C indicates that patient 14 has been active for less than 1 hour per day for the last 4 weeks. In addition, ventricular pacing metric 142D (e.g., a cardiac resynchronization therapy percentage) indicates that IMD 16 has been pacing heart 12 less than 90 percent of the time. As patient metrics 142 indicate, information may be given that is more specific than just a threshold has been exceeded. The actual observed patient metric data, or summary of the data, may be presented in trend summary 138.

Since each of patient metrics 142B-D has exceeded their respective metric-specific threshold, critical indicator 140 is provided for each metric. The user then knows that heart failure risk level 144 is generated with these critical patient metrics. Also, risk level 144 indicates that patient 14 is at "high risk" for being admitted to the hospital for heart failure. As described herein, risk level 144 may have two or more levels that indicate the severity of heart failure for patient 14. In some examples, "low risk" may indicate that no patient metrics have exceeded their respective metric-specific threshold, "medium risk" may indicate that one patient metric has exceeded their respective metric-specific thresholds, and "high risk" may indicate that two or more patient metrics have exceeded their respective metric-specific thresholds. Since three patient metrics, e.g., patient metrics 142B-D, have exceeded their respective metric-specific thresholds, risk level 144 is indicated as "high risk" in this example.

Risk level 144 is highlighted by a double-lined rectangle for easy location by the user. In other examples, risk level 144 may stand out from the rest of screen 130 in different manners. For example, risk level 144 may be of a different color, font size, or be presented with animation (e.g., flashing or scrolling). Alternatively, risk level 144 may be located at the top of screen 130 or other easily identifiable location. Although heart failure risk level 144 is generally presented as a word category, risk level 144 may be presented with a fraction, percentage, weighted average, or other numerical score that indicates that the severity of the heart failure risk level. For example, risk level 144 may be provided as a fraction of the critical patient metrics over the total number of observed patient metrics to give the user an immediate indication of the severity of the heart failure.

Although screen 130 may be a passively presented informational screen, screen 130 may be interactive. The user may select areas of screen 130 to view more details about any of patient metrics 142, e.g., the user may request higher resolution diagnostic information from IMD 16. Screen 130, in other examples, may provide scroll bars, menus, and navigation buttons to allow the user to view additional information, adjust therapy, adjust metric parameters, or perform other operations related to the treatment of patient 14 with the patient metrics and risk level.

In other examples, risk level 144 may be transmitted in a different manner. In other words, the diagnostic information may be transmitted without additional extraneous data such as patient metrics 142. For example, risk level 144 may be transmitted as a single data point associated with the name of patient 14. Alternatively, risk level 144 may be transmitted to a remote computing device as a data point and the remote computing device may update the risk level for that particular patient. In other examples, risk level 144 may be transmitted as part of a text message, electronic mail message, or other formatted message to a mobile computing device carried by a clinician or healthcare professional. After the user receives the diagnostic information, the user may send an interrogation request to IMD 16 for additional information, e.g., higher resolution diagnostic information.

Figure 7:
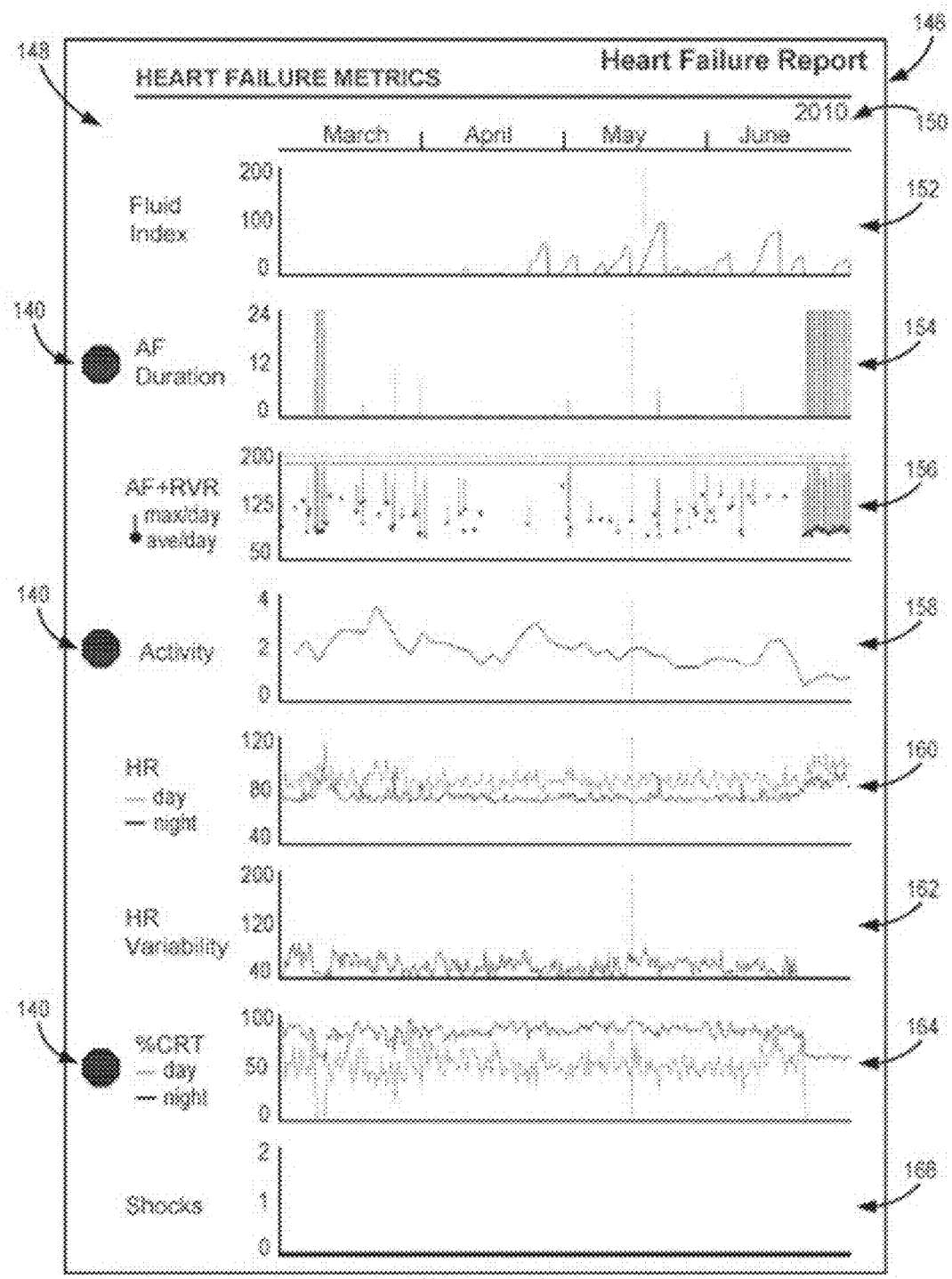
FIG. 7 illustrates an example user interface that includes diagnostic information from a plurality of patient metrics used to generate a heart failure risk scores.

FIG. 7 illustrates an example screen 146 of user interface 104 that includes higher resolution diagnostic information. Screen 146 may include data (e.g., raw or calibrated data)

from all of the patient metrics used to generate the heart failure risk level for patient 14. Since screen 146 includes data collected from patient 14, screen 146 includes higher resolution diagnostic information than the information of screen 130 of FIG. 6. Although screen 146 is described as being presented on user interface 104 of programmer 24, screen 130 may be presented on any user interface of any device used by a healthcare professional. As shown in FIG. 7, screen 146 provides another heart failure report, similar to screen 130 of FIG. 6. However, screen 146 provides higher resolution diagnostic information of heart failure metrics 148 that include those patient metrics used to generate the heart failure risk level 144. Included are the metric data for eight patient metrics 152, 154, 156, 158, 160, 162, 164, and 166. Timeline 150 indicates for which months the data is representative in all the metric graphs. Although this four month period may be the evaluation window, timeline 150 may cover many evaluation windows. For example, the evaluation window may be equal to one week or one month, such that the risk level is reviewed after the evaluation window expires. In addition, the user may move through time with an interactive timeline 150 in other examples. Although not presented in screen 146, the heart failure risk level may also be presented. In some examples, the user may select any point within the graphs for the patient metrics to retrieve specific values of the patient metric at that point in time.

Thoracic fluid index metric 152 is labeled as "Fluid Index." Thoracic fluid index metric 152 illustrates that the thoracic fluid index has been periodically raising and lowering over the months of May and June. In one example, the thoracic fluid index threshold may be approximately 60. However, the thoracic fluid index threshold may be generally between approximately 40 and 200.

Atrial fibrillation duration metric 154 is labeled "AF Duration" and indicates how many hours each day that the patient endured atrial fibrillation. As shown, atrial fibrillation duration metric 154 includes critical indicator 140 because of the days of atrial fibrillation shown at the end of June. An example atrial fibrillation duration threshold may be approximately 6 hours. However, the atrial fibrillation duration threshold may be set generally between approximately 1 hour and 24 hours.

Ventricular contraction metric 156 is labeled "AF+RVR" and indicates the ventricular contraction rate during atrial fibrillation. The graph of ventricular contraction metric 156 provides the average ventricular contraction rate for each day and also the maximum ventricular contraction rate observed during each day. Generally, the ventricular contraction rate during atrial fibrillation threshold may be set between approximately 70 beats per minute and 120 beats per minute for 24 hours. In one example, the ventricular contraction rate threshold may be approximately equal to 90 beats per minute for 24 hours. In other examples, the duration of 24 hours may be shorter or longer.

Activity metric 158 also is highlighted with critical indicator 140. Activity metric 158 is labeled "Activity" and indicates for how many hours the patient is active each day. A patient may be considered active when, for example, the output of an accelerometer exceeds a threshold. Lower activity levels may be a risk factor for heart failure, and the graph of activity metric 158 indicates that patient 14 has been less active at the end of June. In this manner, the patient metric of activity may be a metric where exceeding the metric-specific threshold includes dropping below the threshold. In one example, the patient activity threshold may be approximately equal to 1 hour per day for seven consecutive days. In other examples, the threshold may be set to more or less time over a different duration. Instead of hours per day, other examples of activity metric 158 may provide durations of certain postures, e.g., lying down, sitting up, or standing. In general, activity metric 158 may include measurements of the rigor of patient activity and/or the amount of time patient 14 is active.

Screen 148 also provides for heart rate metrics. Heart rate metric 160 is labeled "HR" and indicates separate graphs for each of the nighttime heart rate and daytime heart rate. In some examples, the nighttime heart rate may be more indicative of heart failure risk. Generally, the nighttime hear rate threshold may be set to between approximately 70 beats per minute and 120 beats per minute for a certain period of time. In one example, the nighttime heart rate threshold may be approximately 85 beats per minute for seven consecutive days. Heart rate variability metric 162 is labeled "HR Variability" and indicates the degree of change in heart rate throughout the day. Since lower heart rate variability may indicate an increased sympathetic tone detrimental to blood flow through the vasculature, heart rate variability may also be a patient metric where exceeding the metric-specific threshold includes dropping below the threshold. In one example, the heart rate variability threshold may be set to approximately 40 milliseconds for seven consecutive days, but other variability thresholds may also be used. In other examples, screen 148 may also provide comparisons between two or more patient metrics, e.g., the difference between day heart rate and nighttime heart rate.

In addition, screen 148 may also provide a few patient metrics derived from therapy delivered to patient 14. Therapy percentage metric 164 is labeled "% CRT" and indicates the percentage of time each day and night that IMD 16 is delivering a cardiac resynchronization therapy, e.g., pacing therapy. Lower percentages of therapy may indicate diminished blood flow through the vasculature. Generally, the cardiac resynchronization therapy percentage threshold may be set to a value between 70 percent and 100 percent for a given period of time. In one example, the cardiac resynchronization therapy percentage threshold may be set to approximately 90 percent for five of seven consecutive days. Since the nighttime therapy percentage is less than 90 percent, critical indicator 140 is used to highlight therapy percentage metric 164.

In other examples, a ventricular pacing percentage may be monitored for patients receiving pacing therapy with dual or single chamber pacing devices. Increased ventricular pacing from single chamber cardiac resynchronization therapy devices may increase the risk of heart failure in some patients due to desynchronization of ventricular contractions in the heart. Conversely, lower ventricular pacing in dual chamber devices may increase the risk of heart failure in some patients.

Further, shock metric 166 is labeled "Shocks" and indicates the number of electrical shock events, e.g., cardioversion or defibrillation, endured by patient 14. As shown in FIG. 7, patient 14 has not been subjected to any shock therapy. Although the threshold may be set to a different value, the electrical shock threshold may generally be set to approximately 1 electrical shock.

Since each of patient metrics 154, 158, and 164 have exceeded their respective metric-specific threshold, critical indicator 140 is provided for each metric. In addition to, or in place of, critical indicators 140, patient metrics may be highlighted with a different text color, circles or boxes surround each metric, or some other indication of the critical level of each metric. In other examples, other patient metrics may be presented in heart failure metrics 148, e.g., blood pressure, blood glucose, lung volume, lung density, or respiration rate, weight, sleep apnea burden derived from respiration, temperature, ischemia burden, sensed cardiac event intervals, and troponin and/or brain natriuretic peptide (BNP) levels.

Although screen 148 may be a passively presented informational screen with higher resolution diagnostic information, screen 148 may be interactive. The user may select areas of screen 148 to view more details about any of the presented patient metrics, for example. The user may also move to different time periods with timeline 150. Screen 130, in other examples, may provide scroll bars, menus, and navigation buttons to allow the user to view additional information, adjust therapy, adjust metric parameters, or perform other operations related to the treatment of patient 14 with the patient metrics and risk level. Further, the user may interact with the graph of each patient metric to expand the graph and view more details of the graph, perhaps even individual values.

In other examples, higher resolution diagnostic information may be presented one patient metric at a time or even raw data that IMD 16 uses to generate the patient metric. For example, during a hospitalization period for patient 14, IMD 16 may transmit the detected thoracic impedances to a remote computing device of a clinician treating patient 14. IMD 16 may transmit detected thoracic impedances at a predetermined interval or in response to an interrogation request from the clinician. The predetermined interval may be generally between approximately one minute and four hours, but other predetermined intervals may be used. The clinician may use some or all of the higher resolution diagnostic information to determine when patient 14 has improved enough to be discharged from a hospital setting, or whether patient 14 should be admitted to the hospital due to heart failure.

Figure 8:
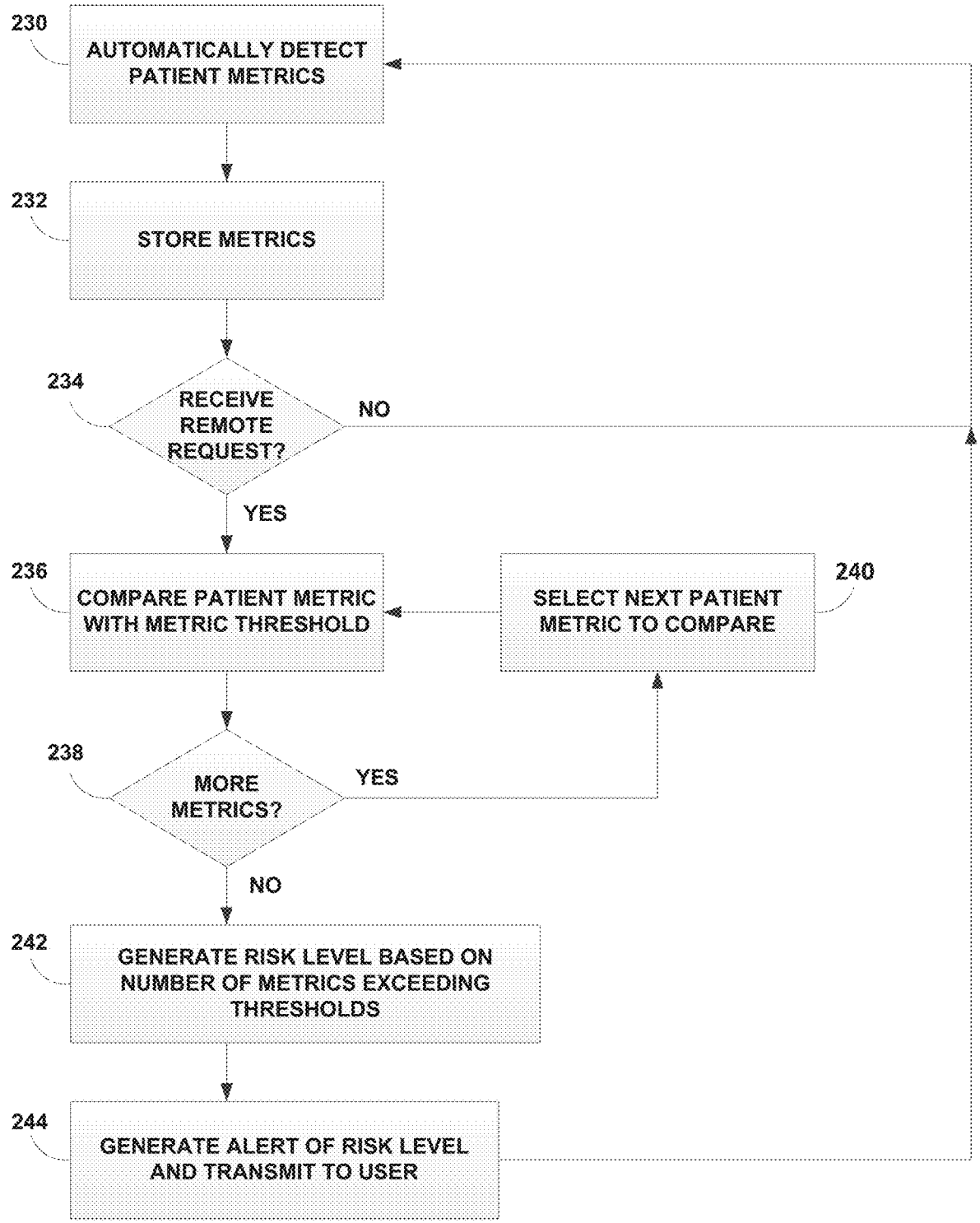
FIG. 8 is a flow diagram of an example technique for generating a heart failure risk score from patient metrics.

FIG. 8 is a flow diagram of an example technique for generating heart failure risk levels, which are examples of HFRSs, from patient metrics. FIG. 8 will be described with IMD 16 both detecting patient metrics and generating heart failure risk levels for the patient, but other examples of the same technique may be applied to other devices (e.g. programmer 24 or external computing device 114 based on diagnostic data received from IMD 16 or one or more other medical devices).

As shown in FIG. 8, metric detection module 92 automatically detects the patient metrics from various electrodes, sensors, and therapy information (230). Metric detection module 92 then stores the patient metrics in metric data 85 of memory 82 (232). If processor 80 does not need to generate the heart failure risk level ("NO" branch of block 204), metric detection module 92 continues to detect patient metrics (230). In some examples, processor 80 may only generate the risk level after an evaluation window expires. For example, if the evaluation window is seven days, processor 80 may only generate the risk level after the seven day period expires. However, processor 80 may generate and transmit the risk level as frequently as every hour or as infrequently as several months. If processor 80 is to generate the heart failure risk level ("Yes" branch of block 234), processor 80 compares one of the patient metrics with the metric-specific threshold of that metric (236). If there are more patient metrics to compare ("Yes" branch of block 238), processor 80 selects the next patient metric to compare (240) and compares the metric to its threshold (236).

Once there are no more patient metrics to compare ("NO" branch of block 208), processor 80 generates the heart failure risk level based on the number of metrics exceeding their thresholds as determined in the comparison step (242). For example, no metrics exceeding their thresholds may be a "low risk" level, one metric exceeding its threshold may be a "medium risk" level, and two or more metrics exceeding their thresholds may be a "high risk" level. In other examples, the risk level may be generated as a fraction, percentage, or other value that represents the number of metrics exceeding their values. In some examples, metric detection module 92 may generate the risk levels with a statistical analysis of the patient metric values instead of using the number of metrics exceeding a threshold.

Once the risk level is generated, processor 80 generates an alert of the risk level and transmits the alert to the user via telemetry module 88 (244). As described herein, the alert may be transmitted on a schedule or as soon as communication is possible to another device or access point. In some examples, the heart failure risk level may only be transmitted when requested by a user. In some examples the alert may also include more detailed information regarding the patient metrics included in the risk level.

The techniques described herein for generating heart failure risk levels were applied in a review of several studies to evaluate for the ability of the generated heart failure risk levels to predict the likelihood that a patient would be re-hospitalized within 30 days for heart failure. Each patient was monitored with an Implantable Cardioverter Defibrillator (ICD) or Cardiac Resynchronization Therapy Defibrillator (CRT-D) devices, e.g., example IMDs, to provide daily measurements of several patient metrics for possible evaluation of heart failure foe each patient. The retrospective analysis evaluated the ability of the generated heart failure risk level to identify which patients are at risk for re-admission to a hospital within 30 days following a hospital discharge after a heart failure event. Only patients with CRT-D devices and at least 90 days of follow-up data were used in the following analysis that included 1,561 patients.

Hospitalization due to heart failure was used as the endpoint in the data analysis. Each cardiovascular hospitalization was carefully adjudicated for signs and symptoms of heart failure which included administration of intra-vascular (IV) or oral diuretic during the hospitalization. A heart failure hospitalization (HFH) group was formed from the evaluated patients, which included patients with at least one heart failure hospitalization and at least 30 days of follow-up data following discharge from the first heart failure hospitalization.

Five patient metrics investigated in this analysis included intra-thoracic impedance, patient activity, night heart rate, heart rate variability, and AF diagnostics. However, other patient metrics could have been evaluated in other examples. AF burden, ventricular rate during AF, and % CRT pacing were combined into AF diagnostics as they may be correlated with each other. Initially each of the patient metrics was evaluated in a univariate fashion to determine the ability of each metric to identify patients at risk for heart failure hospitalization. Criteria were then chosen to determine the metric states of each metric that would correlate to a "High", "Medium", and "Low" risk level. These patient metrics and associated metric states are described in Table 1. In other examples, different criteria may be used to stratify or otherwise determine the metric state of each metric appropriate for effectively identifying the risk level that each patient would be re-hospitalized within 30 days. A "High" metric state may signify the highest probability of identifying a HFH while meeting the criteria approximately 5-10% of the time. The "Medium" metric state signifies a lower risk than the "High" status but a higher risk than the "Low" status. The "Low" metric state signifies minimal risk for a 30-day re-admission to the hospital. However, the metric states are individual risks, not the overall heart failure risk level described later.

As shown in Table 1, the "High" metric state for intra-thoracic impedance is determined based on the cumulative difference between the reference and daily impedance in the previous seven day period. If the daily impedance stays below the reference for the entire period, then the detected impedance is an indicator for a high risk of re-admission. Days with high atrial fibrillation (AF) burden (greater than 6 hours per day) and with poor rate control (Ventricular rate is greater than 90 beats per minute (BPM)) or a loss of CRT pacing (percentage of ventricular pacing less than 90 BPM) was considered "High" evidence for risk of re-hospitalization. Although AF burden may be combined with the loss of CRT pacing or CRT percentage as a single metric, AF burden, CRT percentage, or loss of CRT pacing alone may be used as a single metric in other examples. Days with night heart rate greater than 80 BPM or days with a night heart rate (NHR) greater than or equal to the daytime heart rate (DHR) during the seven day period indicated "High" evidence for risk of re-hospitalization. Similarly, a trend in reducing heart rate variability (HRV) at or below 40 milliseconds (ms) during the seven day period was considered "High" evidence for risk of re-hospitalization. Similarly, a trend in reducing activity during the seven day period indicated "High" evidence for risk of re-hospitalization.

TABLE 1

| Patient Metric | Criteria | Metric State | Score Weight |
|---|---|---|---|
| Intra-thoracic Impedance | ≥1 days Fluid Index ≥60 in 7 days AND Mean(Impedance-Reference) in 7 days <−5.5 Ohms | High | 4 |
| | Not "High" or "Low" | Medium | 2 |
| | Mean(Impedance-Reference) in 7 days >+1.0 and not "High" | Low | 0 |
| Activity | Activity Slope* in 7 days <−100 | High | 2 |
| | Not "High" or "Low" | Medium | 1 |
| | Activity Slope* in 7 days >0 AND not "High" | Low | 0 |
| Heart Rate Variability | ≥5 days with HRV ≤40 ms in last 7 days OR {HRV slope* <−40 AND ≥5 days with HRV ≤40 ms} | High | 2 |
| | HRV slope* <−20 and not "High" | Medium | 1 |
| | Not "High" or "Medium" | Low | 0 |
| Night Heart Rate | ≥1 days with (DHR-NHR) <0 bpm AND ≥5 days with NHR ≥80 min/day | High | 2 |
| | ≥1 days with NHR ≥80 min/day AND not "High" | Medium | 1 |
| | Not "High" or "Medium" | Low | 0 |
| AF + RVR | ≥1 day with AF >6 hrs AND with VR-AF >90 bpm OR 1-6 days with AF >6 hrs AND ≥1 day with % VP <90% | High | 4 |
| | 1-6 days with AF >6 hrs AND ≥1 day with % VP <90% AND Not "High" | Medium | 2 |
| | Not "High" or "Medium" | Low | 0 |

*Slope measurements for HRV and Activity were performed by subtracting the values on day 1-2 from the values on day 6-7 in the window of 7 days post discharge.

A heuristic evaluation of the patient metrics was created by assigning a score to each of the metric states for each patient metric. Then, the five scores were added to determine the heart failure risk level. The scores assigned to each metric state for the patient metrics are shown in Table 1. The intra-thoracic impedance and AF+RVR parameters was weighted double that of the metric states of other parameters. This weighting was used because some patient metrics may have a higher impact of heart failure risk level than other metrics. Alternatively, a Bayesian Belief Network (BBN) model was also created to evaluate all the individual metric states for each patient metric and generate a probabilistic risk score for the heart failure risk level. A 6-node BBN model was created for the patient metrics with heart failure being the parent node and the five different patient metrics as child nodes. The basic assumption of the BBN model is that inadequately treated heart failure causes the patient metrics to change. Therefore, measuring the patient metrics may enable an estimation of the possibility that a heart failure event may reoccur. Also, the BBN model assumes that, in the absence of any information regarding the heart failure status, the patient metrics are independent of each other.

Table 1 provides one example of patient metrics and associated scores based on the values of each metric. In other examples, fewer or greater metrics may be used for the heuristic evaluation of the patient. In addition, the scores provided in Table 1 are examples and may be varied based on the number of metrics evaluated, the number of risk levels for each metric, patient history indicating importance of one or more metrics, or other reasons related to monitoring the patient.

Table 2 provides an alternative set of patient metrics and score weights than the metrics and scores provided in the example of Table 1. For example, the patient metrics of Table 2 may be used when other metrics may not be available or when the patient metrics of Table 2 are those metrics identified as particularly indicative of a re-hospitalization risk. In this manner, a variety of different patient metrics, criteria, and score weights may be used to evaluate the risk of re-hospitalization for a particular patient.

TABLE 2

| Patient Metric | Criteria | Metric State | Score Weight |
|---|---|---|---|
| Intra-thoracic Impedance | ≥1 days Fluid Index ≥60 in 7 days AND Mean(Impedance-Reference) in 7 days <−5.5 Ohms | High | 3 |
| | Mean(Impedance-Reference) in 7 days >+1.0 and not "High" | Medium | 1 |
| | Not "High" or "Medium" | Low | 0 |
| Night Heart Rate | ≥1 days with NHR ≥80 bmp | High | 1 |
| | Not "High" | Low | 0 |
| AF + RVR | TWO or more of: ≥1 day with AF >6 hrs AND with VR-AF >90 bpm; 1-6 days with AF >6 hrs; ≥1 day with % VP <90% | High | 2 |
| | ONE of: ≥1 day with AF >6 hrs AND with VR-AF >90 bpm; 1-6 days with AF >6 hrs; ≥1 day with % VP <90% | Medium | 1 |
| | Not "High" or "Medium" | Low | 0 |

Figure 9:
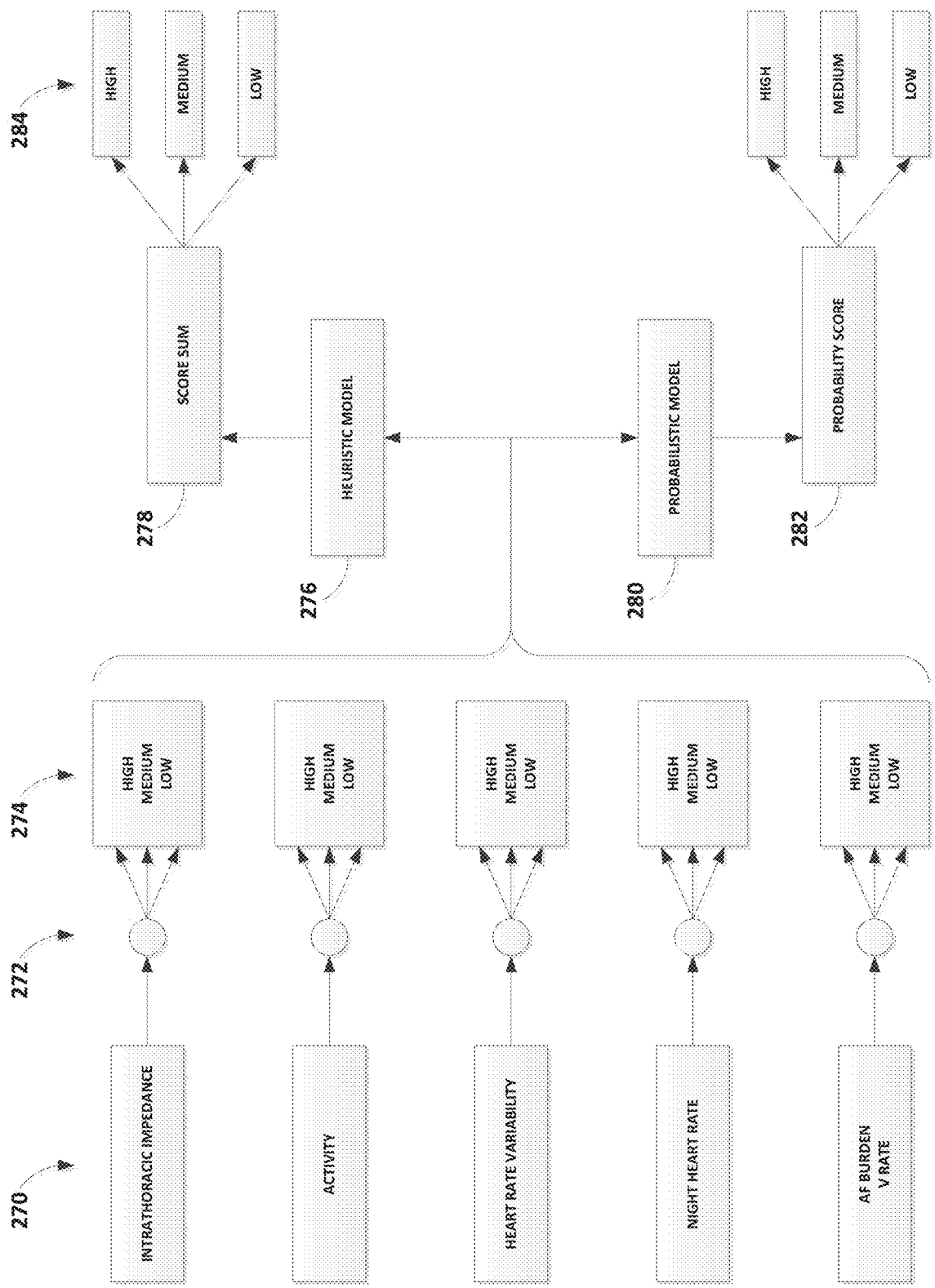
FIG. 9 is a flow diagram of example techniques for generating a heart failure risk score using a heuristic and/or a probabilistic model.

FIG. 9 is a flow diagram of example techniques for generating a heart failure risk level 284 using heuristic model 276 or probabilistic model 280. Heart failure risk level 284 is an example of a periodic HFRS. As shown in FIG. 9, each of the five patient metrics 270 is detected and analyzed using criteria 272. Criteria 272 may be criteria listed in Table 1 or other such metric-specific thresholds. Based on criteria 272, one of the metric states 274 for each patient metric is generated by the implantable device (e.g., IMD 16). Subsequently, the metric states are used to estimate the heart failure risk level using either model. Heuristic model 276 may use score sum 278 to add all of the metric state scores; the resulting sum is used to generate the heart failure risk level 284. Alternatively, probabilistic model 280 may use probability score 282 to identify the probability that the metric states indicate a certain heart failure risk level 284. Heart failure risk level 284 is categorized into three groups for analysis purposes. The thresholds for the different categories were chosen such that the "High" risk level is the top 15% of the scores, or more likely that the patient will be re-hospitalized. The "Low" category was chosen to represent all the diagnostic evaluation where the metric state for all the patient metrics was mostly "Low". The "Medium" category comprises of all other metric state combinations that did not get classified as either "High" or "Low".

At each heart failure hospitalization, the patient metrics were evaluated in the seven days post-hospitalization (e.g., post-discharge) to investigate whether a combined diagnostic criterion can identify the patients who are at higher risk of re-hospitalization for heart failure within the 30 day period following discharge. For patients with multiple heart failure hospitalizations, each hospitalization is considered for the purpose of the analysis if there was at least 30 days of follow-up data after discharge from that hospitalization. During the seven days following discharge after each hospitalization, the patient metrics were evaluated to classify the patient into the different heart failure risk levels. The patients in these risk level groups are then evaluated for heart failure hospitalization in the 30 days following discharge using the Anderson-Gill model, an extension of the Cox proportional hazards model that accounts for multiple evaluations in patients. A Generalized Estimating Equations (GEE) model is also used to estimate the probability of heart failure hospitalization in the next 30 days for each risk level group.

The results for each metric state are shown in Table 3. These results were derived from a heart failure hospitalization group comprising of a total of 254 heart failure hospitalizations in 166 patients. The results show that the "High" metric state during seven days post discharge for impedance, AF+RVR, and night heart rate identifies patients who were at a significantly higher risk for a 30 day re-admission due to heart failure.

TABLE 3

| Patient Metric | Metric State | Number of HF hospitalizations (%) | Number of 30-day readmission (%) |
|---|---|---|---|
| Impedance | High | 27 (11%) | 9 (33.3%) |
|  | Medium | 129 (53%) | 18 (14.0%) |
|  | Low | 88 (36%) | 4 (4.5%) |
| AF + RVR | High | 14 (6%) | 6 (42.9%) |
|  | Medium | 45 (18%) | 11 (24.4%) |
|  | Low | 195 (77%) | 17 (8.7%) |
| Night Heart Rate | High | 30 (13%) | 9 (30.0%) |
|  | Medium | 68 (29%) | 11 (16.2%) |
|  | Low | 139 (59%) | 12 (8.6%) |
| Activity | High | 27 (11%) | 7 (25.9%) |
|  | Medium | 70 (28%) | 10 (14.3%) |
|  | Low | 157 (62%) | 17 (10.8%) |
| Heart Rate Variability | High | 27 (16%) | 7 (25.9%) |
|  | Medium | 27 (16%) | 4 (14.8%) |
|  | Low | 114 (68%) | 11 (9.6%) |

The categorization of the heuristic model of patient metrics, by adding the scores assigned for each metric state during the seven day evaluation period, yielded three groups as shown in Table 4. A score sum of 0-2 indicates low evidence from the patient metrics that re-hospitalization due to heart failure is likely, whereas a score sum of greater than 6 indicates high evidence from patient metrics that re-hospitalization due to heart failure is likely. The cut-off for the low evidence group was chosen such that the metric states from all patient metrics is mostly "low". The cut-off for the high evidence group was chosen such that the high risk group included the top 15% of the sum scores. Based on the results, patients in the high risk group are almost 17 times more likely to be re-hospitalized within 30 days for heart failure than those patients included in the low risk group.

TABLE 4

| Score Sum Groups | Number of HF hospitalizations (%) | Number of 30-day re-admission (%) | HR (95% CI) | p-value |
|---|---|---|---|---|
| 0-2 | 107 (42%) | 3 (2.8%) | Reference Group |  |
| 3-5 | 108 (43%) | 16 (14.8%) | 5.59 (1.66-18.91) | 0.006 |
| 6-14 | 39 (15%) | 15 (38.5%) | 16.76 (4.92-57.08) | <0.001 |

Figure 10:
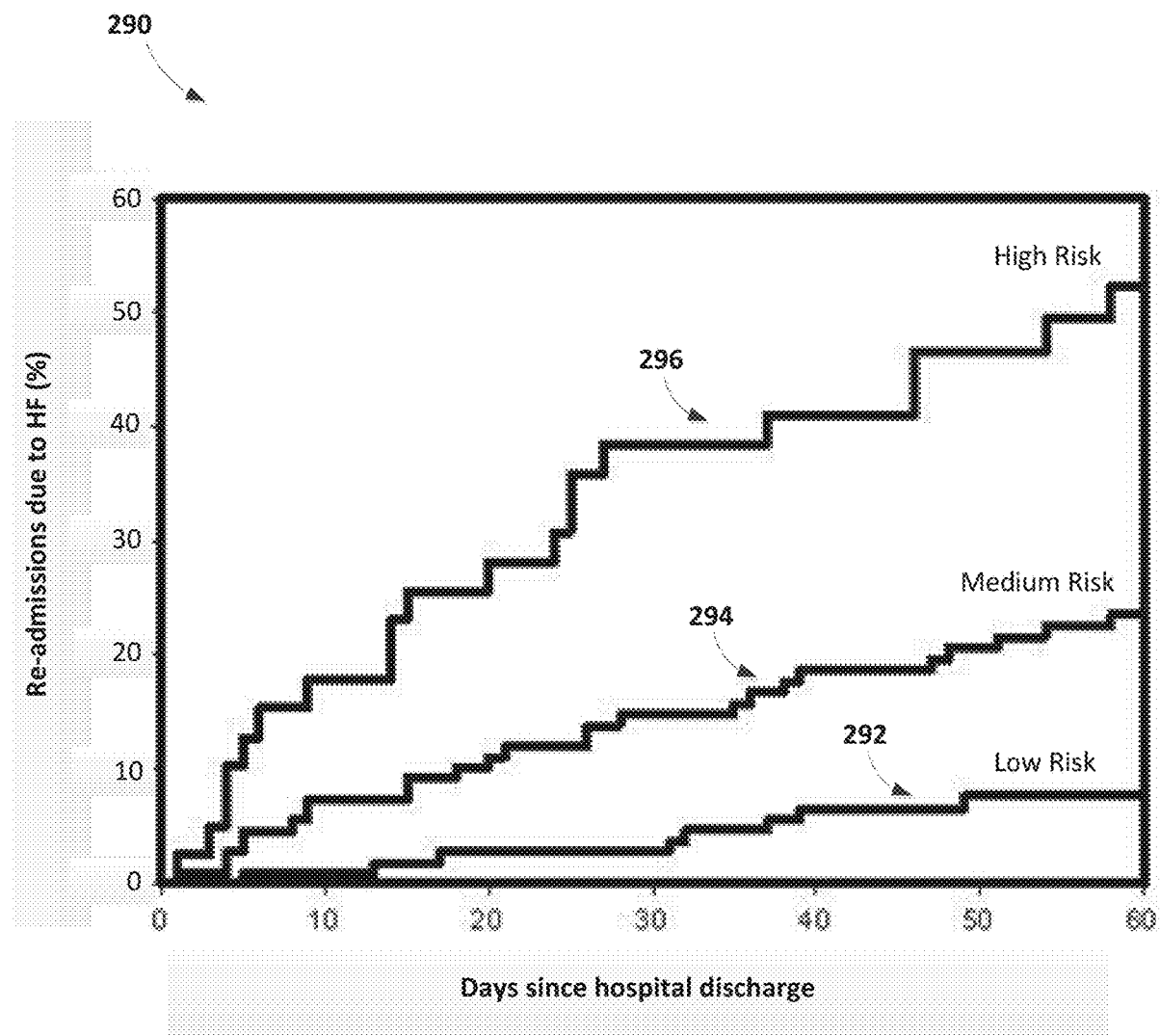
FIG. 10 is a graph of example hospitalization rates based on a generated risk level using a heuristic model and/or a probabilistic model.

FIG. 10 includes graph 290 of example re-hospitalization rates based on a generated risk level using heuristic model 276. Graph 290 was generated as a Kaplan Meier curve for incidence of re-hospitalization due to heart failure. As shown in FIG. 9, graph 290 provides low risk rate 292, medium risk rate 294, and high risk rate 296 over time. In other words, graph 290 indicates the percentage of patients with each risk level that were re-admitted to the hospital a certain number of days from the last hospital discharge. Low risk rate 292 includes patients with a low risk level, medium risk rate 294 includes patients with a medium risk level, and high risk rate 296 includes patients with a high risk level. The risk levels were described above with respect to the sum score. In other examples, similar risk rates may be seen if low risk level patients had no patient metrics exceeding the respective specific metric threshold, medium risk level patients had one patient metric exceeding the respective specific metric threshold, and high risk level patients had two or more patient metrics exceeding the respective specific metric thresholds.

Generally, patients with more severe risk levels had a higher re-admission rate to the hospital than patients with lower risk levels. For example, high risk rate 296 indicates that patients with a high risk level had an approximately 52% re-hospitalization rate after 60 days post-discharge compared with an approximately 8% re-hospitalization rate after 60 days post-discharge for low risk level patients. Since higher risk levels may indicate a higher probability that a particular patient may be re-hospitalized, a clinician may adjust treatment or otherwise help a patient with a more severe risk level to prevent future hospitalization due to heart failure.

The categorization of the probabilistic model of patient metrics, using the Bayesian Belief Network model for the metric state of each patient metric during the seven day diagnostic evaluation, yielded three groups as shown in Table 5. A probability score of less than 5% indicates a low risk level from the patient metrics, whereas a probability score of greater than 25% indicates a high risk level from the patient metrics. The cut-off for the low risk level group was chosen such that the metric state from all patient metrics was mostly "low". The cut-off for the high risk level group was chosen such that the high risk level group included the top 15% of the probability scores. According to the probabilistic model, patients in the high risk level group is 26 times more likely to be re-hospitalized within 30 days of discharge for heart failure than patients in the low risk level group.

TABLE 5

| Probability Score Groups | Number of HF hospitalizations (%) | Number of 30-day readmission (%) | HR (95% CI) | p-value |
|---|---|---|---|---|
| <5% | 111 (44%) | 2 (1.8%) | Reference Group | |
| 5%-25% | 106 (42%) | 18 (17.0%) | 10.11 (2.36-43.22) | 0.002 |
| ≥25% | 37 (15%) | 14 (37.8%) | 26.12 (6.32-107.90) | <0.001 |

Figure 11:
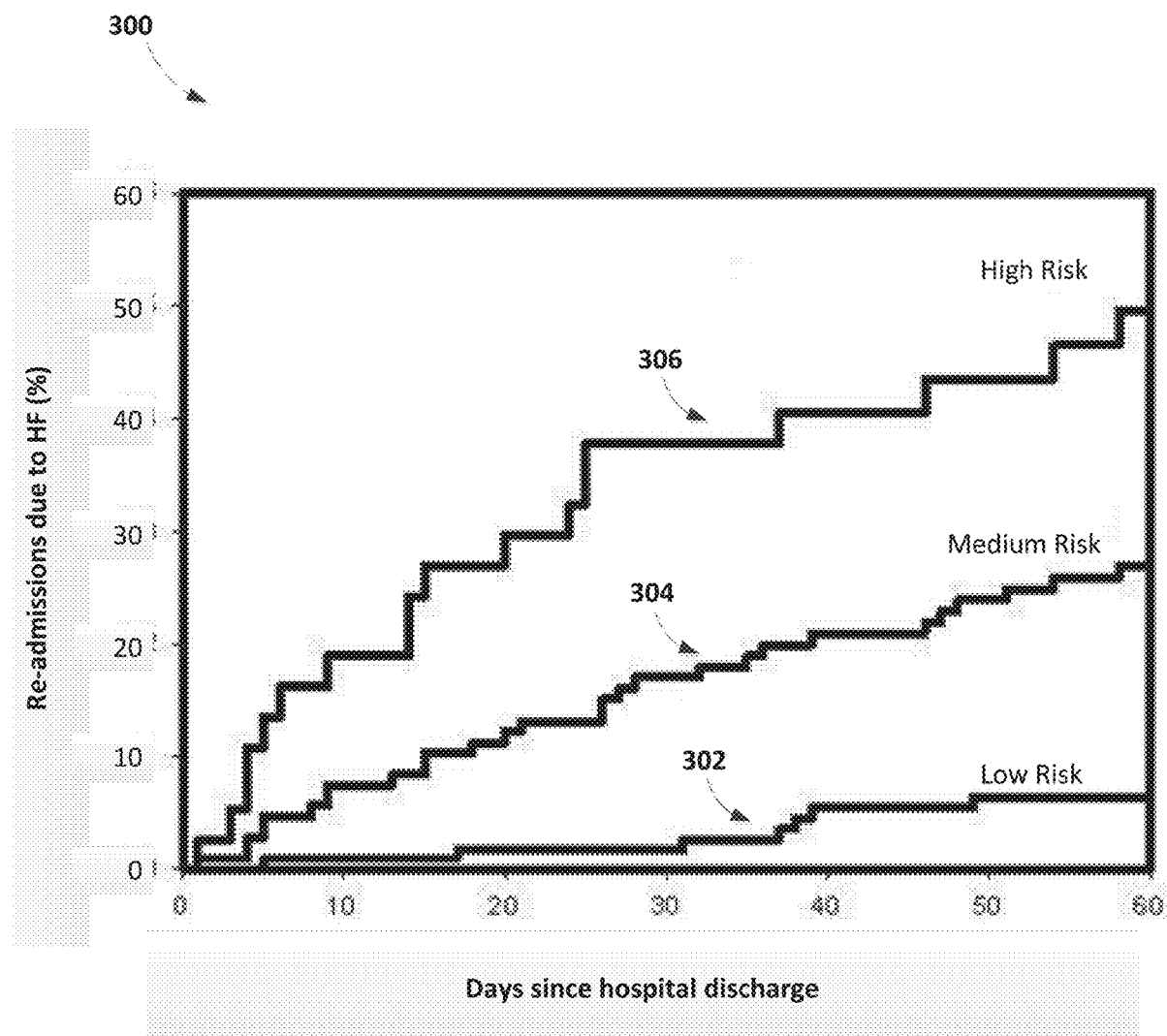
FIG. 11 is a graph of example hospitalization rates based on a generated risk level using a probabilistic model.

FIG. 11 includes graph 300 of example re-hospitalization rates based on a generated risk level using a probabilistic model. Graph 300 was generated as a Kaplan Meier curve for incidence of re-hospitalization due to heart failure, similar to graph 290 of FIG. 10. As shown in FIG. 11, graph 300 provides low risk rate 302, medium risk rate 304, and high risk rate 306 over time. In other words, graph 300 indicates the percentage of patients with each risk level that were re-admitted to the hospital a certain number of days from the last hospital discharge. Low risk rate 302 includes patients with a low risk level, medium risk rate 304 includes patients with a medium risk level, and high risk rate 306 includes patients with a high risk level. This risk rates correspond to the data presented in Table 5. The risk levels were described above with respect to the probability score generated by the BBN model.

Generally, patients with more severe risk levels had a higher re-admission rate to the hospital than patients with lower risk levels. For example, high risk rate 306 indicates that patients with a high risk level had an approximately 50% re-hospitalization rate after 60 days post-discharge compared with an approximately 6% re-hospitalization rate after 60 days post-discharge for low risk level patients. Since higher risk levels may indicate a higher probability that a particular patient may be re-hospitalized, a clinician may adjust treatment or otherwise help a patient with a more severe risk level to prevent future hospitalization due to heart failure.

Figure 12:
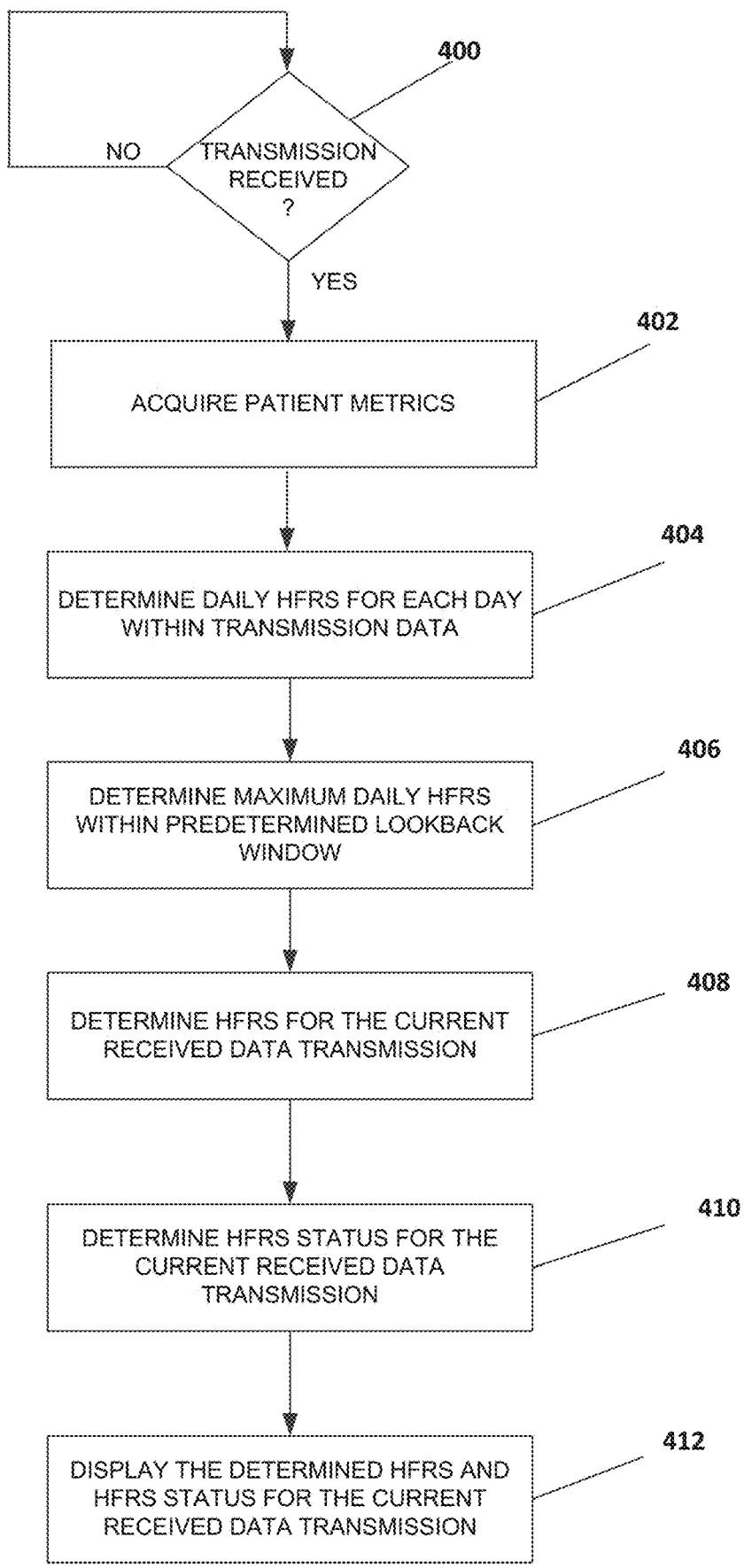
FIG. 12 is a flow diagram of a method of differentiating determined heart failure status in a heart failure monitoring system, according to an example of the present disclosure.

FIG. 12 is a flow diagram of a method of differentiating HFRS status in a heart failure monitoring system, according to an example of the present disclosure. During remote monitoring of patient and/or device status, multiple transmissions of patient data from IMD 16 to external device 114 may occur. For example, data transmissions from the IMD 16 to the external device 114 may be initiated manually by the patient, may be automatic transmissions scheduled by the clinician to occur periodically, such as every three months, or every 30 days for example, or may be device initiated, such as in response to an increased impedance level, or a low battery indication for the device, for example. As a result, given the multiple patients being monitored by a given clinician, the number of such data transmissions that need to be reviewed can tend to be onerous on the clinician. In order to reduce the burden associated with the monitoring of these multiple data transmissions by the clinician, a prioritization technique may be enabled at the external device 114 that provides additional information to further differentiate between notifications regarding/associated with heart failure risk levels resulting from the detected patient metrics. In one example, a differentiated heart failure risk score may be enabled that includes differentiation between a high heart failure risk score ("HFRS") and an ongoing high HFRS. In another example, a differentiated heart failure risk score that includes differentiation between a high HFRS and an ongoing high HFRS may be enabled, along with a differentiated heart failure risk score that includes differentiation between a medium HFRS and an ongoing medium HFRS.

As illustrated in FIG. 12, according to one example prioritization technique, determining heart failure risks levels of a patient for display via a patient monitoring system is initiated upon receipt of a data transmission by external device 114 from a remote medical device, such as from the IMD 16 for example, YES in Block 400. As described above, the received data transmission may result from a data transmission that was initiated manually by the patient, may be as a result of automatic transmissions scheduled by the clinician to occur periodically, such as every three months, or every 30 days for example, or may be device initiated, such as in response to an increased impedance level, or a low battery indication for the device, for example. Upon receipt of the data transmission from the remote medical device, external device 114 acquires patient metrics Block 402, such as the metrics used to determine the high, medium and low risk levels described above, in reference to FIGS. 6-9, for example, from the remote medical device, IMD 16. Based on the acquired patient metrics, one or more of processors 118 of external device 114 determine a daily HFRS for each day (or periodic for any other period) within a time period between a previous received data transmission and the current received data transmission, Block 404. A maximum HFRS of each determined daily HFRS within a lookback window prior to the current received rata transmission, such as 30 days for example, is determined Block 406. An HFRS is determined for the current data transmission based on the determined maximum daily HFRS, Block 408, and an HFRS status is determined for the current received data transmission based on at least one of whether a prior transmission included the maximum HFRS within the lookback window or an HFRS status of a prior transmission within the lookback window, Block 410. The determined HFRS and HFRS status for the current data transmission may then be displayed on the external device 114, Block 412, via input/output device 116.

FIGS. 13A-G are schematic diagrams illustrating exemplary scenarios of differentiation of heart failure risk score alerts in a heart failure monitoring system, according to the present disclosure. In the example illustrated in FIG. 13A, a data transmission 420 from a remote monitoring device, such as IMD 16 for example, was received by the external device 114 on Dec. 9, 2015. Upon receipt of the data transmission 420, one or more processor(s) 118 of external device 114 acquires patient metrics from the remote monitoring device and determines a daily HFRS 422 of either high H, medium M, or low L for each day during a time period extending subsequent to a previous data transmission, or as in the example of FIG. 13A, if there is no data previous transmission, the time period extends subsequent to the date that the HFRS differentiation algorithm of the present disclosure was enabled in the external device 114, i.e., Dec. 1, 2015, to the day of receipt of the current data transmission 420, using the patient metric trends described above, for example.

Figure 13A:
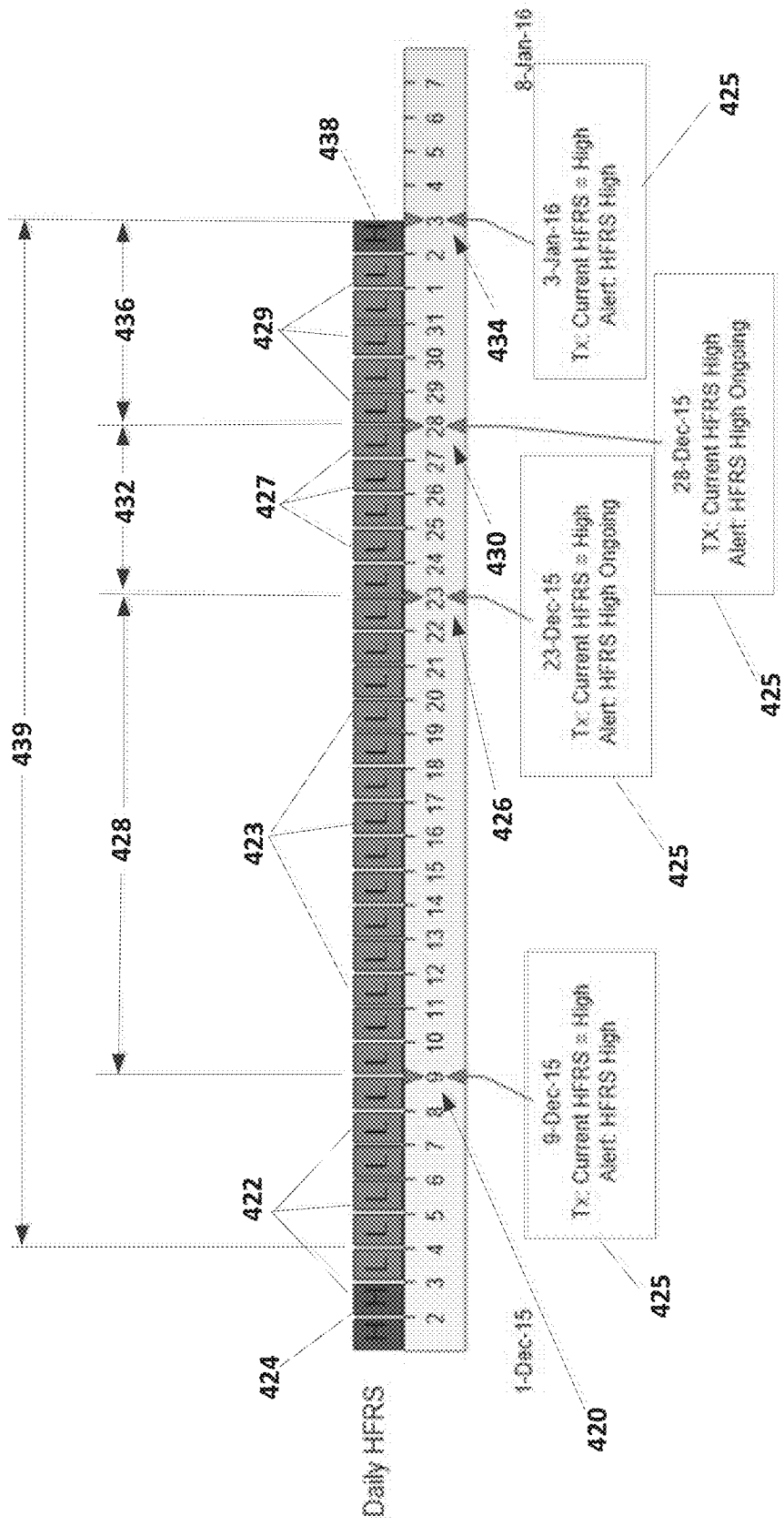
FIGS. 13A-G are schematic diagrams illustrating exemplary scenarios of differentiation of heart failure risk status in a heart failure monitoring system, according to the present disclosure.

External device 114 stores each daily HFRS 422 of either high H, medium M, or low L determined during the time period extending subsequent to a previous data transmission within memory 119. External device 114 then determines a maximum daily HFRS of each daily HFRS determined for each day within a lookback window occurring prior to receipt of the current data transmission 420. In one example, the lookback window may be a 30 day lookback window, and if it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13A, the maximum daily HFRS for the current data transmission 420 is determined to be HFRS 424, which was determined to have a daily HFRS of high H.

Since the maximum daily HFRS was determined to be high H, the external device 114 determines that the HFRS for the current data transmission 420 is HFRS of high H. In addition, since neither an HFRS high H alert nor an HFRS high ongoing alert was generated for a data transmission received prior to the current received data transmission 420 within the lookback window (in the example of FIG. 13A, there was no data transmission received prior to the current received data transmission 420 since the current data transmission 420 is the initial data transmission received since the HFRS differentiation algorithm feature was enabled), the external device 114 determines that an HFRS status for the current data transmission 420 is a high HFRS alert, rather than a high ongoing HFRS alert. Therefore, the external device 114 generates a display 425 associated with the current received data transmission 420 indicating one or both of the determination that the HFRS associated with the current received data transmission 420 is a high HFRS, "Current HFRS=High" and the HFRS alert associated with the current received data transmission 420 is a high HFRS alert, "Alert: HFRS High", which may then be displayed by the external device 114 for subsequent review by a clinician.

After generating display 425 and storing associated with data transmission 420, external device 114 waits for receipt of a next data transmission from the remote monitoring device, which, in the example illustrated in FIG. 13A, is a data transmission 426 received on Dec. 23, 2015. Upon receipt of the next data transmission 426, the external device 114 determines a daily HFRS 423 of either high H, medium M, or low L for each day during a time period 428 subsequent to the previous data transmission 420 and up to receipt of the current data transmission 426.

External device 114 stores each daily HFRS 423 of either high H, medium M, or low L determined during the time period 428 extending subsequent to a previous data transmission within memory 119. External device 114 then determines a maximum daily HFRS of each daily HFRS determined within a lookback window prior to the current received data transmission 426. Assuming a 30 day lookback window, since it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13A, the maximum daily HFRS during the lookback window for the current data transmission 426 is again determined to be daily HFRS 424. Since the maximum daily HFRS in the lookback window for the current data transmission 426 was determined to be a HFRS of high H, the external device 114 determines that the HFRS associated with the current received data transmission 426 is a high H HFRS. In addition, since an HFRS high alert was generated for data transmission 420 received prior to the current data transmission 426, external device 114 determines that an HFRS alert for the current received data transmission 426 is a high ongoing alert. Therefore, the external device 114 generates a display 425 associated with the current received data transmission 426 indicating one or both of the determination that the HFRS associated with the current received data transmission 426 is a high HFRS, "Current HFRS=High" and the HFRS alert associated with the current received data transmission 426 is a high ongoing alert, "Alert: HFRS High Ongoing", which may then be displayed by the external device 114 for subsequent review by a clinician.

After storing the generated the display 425 associated with received data transmission 426, external device 114 waits for receipt of a next data transmission from the remote monitoring device, which, in the example illustrated in FIG. 13A, is a data transmission 430 received on Dec. 28, 2015. Upon receipt of the next data transmission 430, the external device 114 determines a daily HFRS 427 of high H, medium M, or low L for each day during a time period 432 subsequent to the previous data transmission 426 and up to receipt of the current data transmission 430. In the example of FIG. 13A, upon receipt of the current data transmission 430, the external device 114 determines a daily HFRS of low L for each day during the time period 432 between the day of receipt of the previous received data transmission 426 and receipt of the current data transmission 430.

External device 114 stores each daily HFRS 427 of either high H, medium M, or low L determined during the time period 432 extending subsequent to a previous data transmission within memory 119. External device 114 stores each daily HFRS 427 of either high H, medium M, or low L determined during the time period 432 extending subsequent to a previous data transmission within memory 119. External device 114 then determines a maximum daily HFRS of each daily HFRS determined for each day within a lookback window prior to the current received data transmission 430. Assuming a 30 day lookback window, since it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13A, the maximum daily HFRS within the lookback window for the current data transmission is determined to be daily HFRS 424, which was determined to have a daily HFRS of high H. Since the maximum daily HFRS is determined to be high H, the external device 114 determines that the daily HFRS associated with the current received data transmission 430 is a high H HFRS. In addition, since either an HFRS high alert or an HFRS high ongoing alert was generated for a previous data transmission within the lookback window, i.e., for previous data transmission 420 and previous data transmission 426, respectively, the external device 114 determines that an HFRS alert for the current received data transmission 430 is a high ongoing HFRS alert. Therefore, the external device 114 generates a display 425 associated with the current received data transmission 430 indicating one or both of the determination that the HFRS associated with the current received data transmission 430 is a high HFRS, "Current HFRS=High" and the HFRS alert associated with the current received data transmission 430 is a high ongoing HFRS alert, "Alert: HFRS High Ongoing", which may then be displayed by the external device 114 for subsequent review by a clinician.

After generating and storing the display 425 associated with the current data transmission 430, external device 114 waits for receipt of a next data transmission from the remote monitoring device, which, in the example illustrated in FIG. 13A, is data transmission 434 received on Jan. 3, 2016. Upon receipt of the next data transmission 434, the external device 114 determines a daily HFRS 429 of either high H, medium M, or low L for each day during a time period 436 subsequent to the previous data transmission 430 and up to receipt of the current received data transmission 434.

External device 114 stores each daily HFRS 429 of either high H, medium M, or low L determined during the time period 436 extending subsequent to a previous data transmission within memory 119. External device 114 then determines a maximum daily HFRS of the daily HFRS determined for each day within a lookback window 439 prior to the current received data transmission 434, i.e., between Dec. 4, 2015-Jan. 3, 2016. In the example of FIG. 13A, the maximum daily HFRS for the current received data transmission 434 was determined to be daily HFRS 438, which occurred on Jan. 2, 2016 and was determined to be high H. Therefore, since the maximum daily HFRS within the lookback window 439 was determined to be high H, the external device 114 determines that the HFRS for the current received data transmission 434 is a high HFRS. In addition, since either an HFRS high alert or an HFRS high ongoing alert was generated within the lookback window for a previous data transmission, i.e., previous transmission 420, previous data transmission 426 and previous data transmission 430, but the most recent day with a daily HFRS of high H in a prior transmission, i.e., Dec. 3, 2015 associated with received prior data transmission 620, is not included in the lookback window 639, the external device 114 determines that an HFRS alert for the current data transmission 434 is an HFRS high alert, rather than an HFRS ongoing high alert. Therefore, the external device 114 generates a display 425 associated with the current received data transmission 434 indicating one or both of the determination that the HFRS associated with the current received data transmission 434 is a high HFRS, "Current HFRS=High" and the HFRS alert associated with the current received data transmission 434 is a high HFRS alert, "Alert: HFRS High", which may then be stored in memory 119 and displayed by the external device 114 for subsequent review by a clinician.

According to another example, if the daily HFRS 438 on Jan. 2, 2016 was determined to be medium "M" rather than high "H", as illustrated in FIG. 13A, the maximum daily HFRS for the current received data transmission 434 in FIG. 13A would be determined to be medium "M" rather than high "H", since the maximum daily HFRS during the lookup window 439 would be the HFRS of medium determined for daily HFRS 438. As a result, the external device 114 would determine that the HRFS for the current data transmission 434 is medium M, and that the HFRS alert was a medium HFRS alert since a medium alert did not occur prior to the current data transmission 439. Therefore, the external device 114 would generate the display 425 associated with the current received data transmission 434 to indicate one or both of the determination that the HFRS associated with the current received data transmission 434 is a medium HFRS, "Current HFRS=Medium" and the HFRS alert associated with the current received data transmission 434 is a medium HFRS alert, "Alert: HFRS Medium", which may then be stored in memory 119 and displayed by the external device 114 for subsequent review by a clinician.

In the example illustrated in FIG. 13A, or in the example where the daily HFRS 438 is determined to be medium M, the external device 114 could further differentiate the HFRS for the current data transmission 434 by determining that since the maximum daily HFRS occurred during the current data transmission 434, i.e., during time window 436 associated with the current data transmission 434, the HFRS for the current data transmission 434 is a new high HFRS or a new medium HFRS, respectively. As a result, the external device 114 would generate the display to indicate that the HFRS for the current data transmission 434 is a new high, "HFRS=High New", or to indicate that the HFRS for the current data transmission 434 is a new medium, "HFRS=Medium New", respectively.

Similarly, according to another example, if the daily HFRS 438 on Jan. 2, 2016 was determined to be low "L" rather than high "H" as illustrated in FIG. 13A, the maximum daily HFRS for the current received data transmission 434 would be determined to be low "L" rather than high "H", since maximum daily HFRS during the lookback table 439 would be a daily HFRS of low. As a result, the external device 114 would determine that the HRFS for the current data transmission 434 is low L, and that the HFRS alert was a low HFRS alert. Therefore, the external device 114 would generate the display 425 associated with the current received data transmission 434 indicating one or both of the determination that the HFRS associated with the current received data transmission 434 is a low HFRS, "Current HFRS=Low" and the HFRS alert associated with the current received data transmission 434 is a low HFRS alert, "Alert: HFRS Low", which may then be stored and displayed by the external device 114 for subsequent review by a clinician.

It should be noted that, as illustrated in FIG. 13A, no daily HFRS is determined by the external device 114 subsequent to the most recent received data transmission 434, i.e., for Jan. 3, 2016 and beyond. According to the HFRS differentiation algorithm of the present disclosure, a daily HFRS subsequent to a most recent received data transmission is not determined until the next received data transmission (not shown) is received by the external device as part of a subsequent determination of a daily HFRS for each day during a time period (not shown) between the day of receipt of the previous data transmission 438 and up to receipt of the next received transmission. Therefore, for each data transmission received, the external device 114 only determines a daily HFRS of high H, medium M, or low L for each day during a time period subsequent to the previous data transmission and up to receipt of the current data transmission, and updates the previous stored daily HFRS for each previous received data transmission with the current determined daily HFRS for each previous received data transmission associated with the current received data transmission.

Figure 13B:
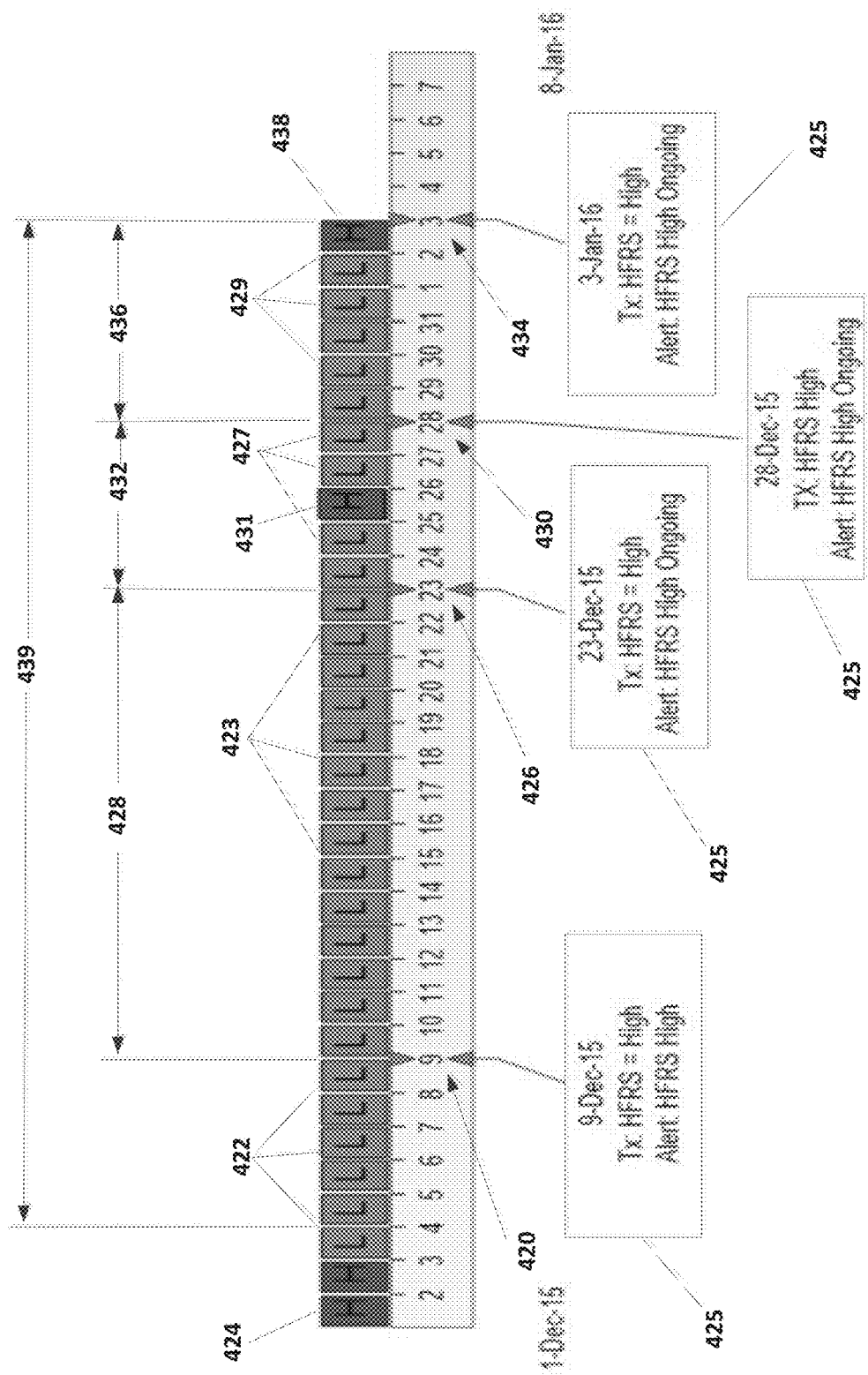

The example illustrated in FIG. 13B is similar to the example illustrated in FIG. 13A with the exception that during the receipt of a data transmission 430 on Dec. 28, 2015, the daily HFRS 431 for Dec. 25, 2015 is determined to be high "H" rather low "L". In the example of FIG. 13 B, after generating the display 425 associated with received data transmission 426, external device 114 waits for receipt of a next data transmission from the remote monitoring device, which, in the example illustrated in FIG. 13B, is data transmission 430 received on Dec. 28, 2015. Upon receipt of the next data transmission 430, the external device 114 acquires patient metrics from the remote monitoring device and determines a daily HFRS 427 of high H, medium M, or low L for each day during a time period 432 subsequent to the previous data transmission 426 and up to receipt of the current data transmission 430. In the example of FIG. 13B, a daily HFRS of high H was determined for daily HFRS 431 occurring during the time period 432 on Dec. 25, 2015.

External device 114 stores each daily HFRS 427 of either high H, medium M, or low L determined during the time period 432 extending subsequent to a previous data transmission within memory 119. External device 114 then determines a maximum daily HFRS of each daily HFRS determined for each day within a lookback window prior to the current received data transmission 430. In the example of FIG. 13B, the maximum daily HFRS for the current data transmission 430 is determined to be daily HFRS 424 (HFRS 424 is determined to be greater than HFRS 431), which occurred on Dec. 1, 2015, and therefore a daily HFRS of high H is determined to have occurred during the current lookback window for the current received data transmission 430. Since the maximum daily HFRS was determined to be high, the external device 114 determines that the HFRS for the current data transmission 430 is a high HFRS. In addition, since either an HFRS high alert or an HFRS high ongoing alert was received for a previous data transmission, i.e., previous data transmission 420 and previous data transmission 426, respectively, external device 114 determines that an HFRS alert for the current received data transmission 430 is a high ongoing HFRS alert. Therefore, the external device 114 generates and stores a display 425 associated with the current received data transmission 430 indicating one or both of the determination that the HFRS associated with the current received data transmission 430 is a high HFRS, "Current HFRS=High" and the HFRS alert associated with the current received data transmission 430 is a high ongoing HFRS alert, "Alert: HFRS High Ongoing", which may then be displayed by the external device 114 for subsequent review by a clinician.

According to another example, the maximum daily HFRS for the current data transmission 430 in FIG. 13B is determined to be daily HFRS 431 (HFRS 431 is determined to be greater than HFRS 424), which was determined to have a daily HFRS of high H. Since the maximum daily HFRS was determined to be high H, the external device 114 determines that the HFRS for the current received data transmission 430 is a high HFRS. In addition, since either an HFRS high alert or an HFRS high ongoing alert was received for a previous data transmission, i.e., previous data transmission 420 and previous data transmission 426, respectively, external device 114 determines that an HFRS alert for the current received data transmission 430 is a high ongoing HFRS alert. Therefore, the external device 114 would generate a display 425 associated with the current received data transmission 430 indicating one or both of the determination that the HFRS associated with the current received data transmission 430 is a high HFRS, "Current HFRS=High" and the HFRS alert associated with the current received data transmission 430 is a high ongoing HFRS alert, "Alert: HFRS High Ongoing", which may then be stored and displayed by the external device 114 for subsequent review by a clinician.

After generating the display 425 associated with data transmission 430, external device 114 waits for receipt of a next data transmission from the remote monitoring device, which, in the example illustrated in FIG. 13B, is data transmission 434, received on Jan. 3, 2016. Upon receipt of the next data transmission 434, the external device 114 determines a daily HFRS 429 of either high H, medium M, or low L for each day during a time period 436 subsequent to the previous data transmission 430 and up to receipt of the current data transmission 434.

External device 114 stores each daily HFRS 429 of either high H, medium M, or low L determined during the time period 436 extending subsequent to a previous data transmission within memory 119. External device 114 then determines a maximum daily HFRS of the daily HFRS determined for each day within a lookback window 439 prior to the current received data transmission 434, i.e., between Dec. 4, 2015-Jan. 3, 2016. In the example of FIG. 13B, the maximum daily HFRS was determined to be daily HFRS 431 (daily HFRS 431 is greater than daily HFRS 438), which occurred on Dec. 25, 2015 and was determined to be high H. Since the maximum daily HFRS determined during the lookback window 439 was determined to be high H, the external device 114 determines that the HFRS for the current received data transmission 434 is a high HFRS. In addition, since either an HFRS high alert or an HFRS high ongoing alert was determined for a previous data transmission within the lookback window 439, i.e., a high ongoing HFRS alert was determined for previous data transmission 426 and 430, external device 114 determines that an HFRS alert for the current received data transmission 430 is a high ongoing HFRS alert. Therefore, the external device 114 generates and stores a display 425 associated with the current received data transmission 434 indicating one or both of the determination that the HFRS associated with the current received data transmission 434 is a high HFRS, "Current HFRS=High" and the HFRS alert associated with the current received data transmission 434 is a high ongoing HFRS alert, "Alert: HFRS High Ongoing", which may then be displayed by the external device 114 for subsequent review by a clinician.

According to another example, the maximum daily HFRS for the current data transmission 434 may be determined to be daily HFRS 438 (HFRS 438 is determined to be greater than HFRS 431), which occurred on Jan. 2, 2016, and therefore a daily HFRS of high H is determined to have occurred during the lookback window 439 for the current received data transmission 434. Since the maximum daily HFRS was determined to be high H, the external device 114 determines that the HFRS for the current received data transmission 438 is a high HFRS. In addition, since either an HFRS high alert or an HFRS high ongoing alert was determined for a previous data transmission, i.e., a high HFRS alert was determined for previous data transmission 420, and a high ongoing HFRS alert previous was determined for previous data transmission 426 and 430, external device 114 determines that an HFRS alert for the current received data transmission 430 is a high ongoing HFRS alert. Therefore, the external device 114 would generate and store a display 425 associated with the current received data transmission 434 indicating the determination that the HFRS associated with the current received data transmission 434 is a high HFRS, "Current HFRS=High" and the HFRS alert associated with the current received data transmission 434 is a high ongoing HRFS alert, "Alert: HFRS High Ongoing, which may then be displayed by the external device 114 for subsequent review by a clinician.

In the example illustrated in FIG. 13B, the external device 114 could further differentiate the HFRS for the current data transmission 434 by determining that since the maximum daily HFRS occurred during the current data transmission 434, i.e., during time window 436 associated with the current data transmission 434, the HFRS for the current data transmission 434 is a new high HFRS. As a result, the external device 114 would generate and store the display to indicate that the HFRS for the current data transmission 434 is a new high, "HFRS=HIGH New". In the same way, the external device 114 could further differentiate the HFRS for the current data transmission 430 by determining that since the maximum daily HFRS occurred during the current data transmission 430, i.e., during time window 432 associated with the current data transmission 430, the HFRS for the current data transmission 430 is a new high HFRS. As a result, the external device 114 would generate and store the display to indicate that the HFRS for the current data transmission 430 is a new high, "HFRS=HIGH New".

Figure 13C:
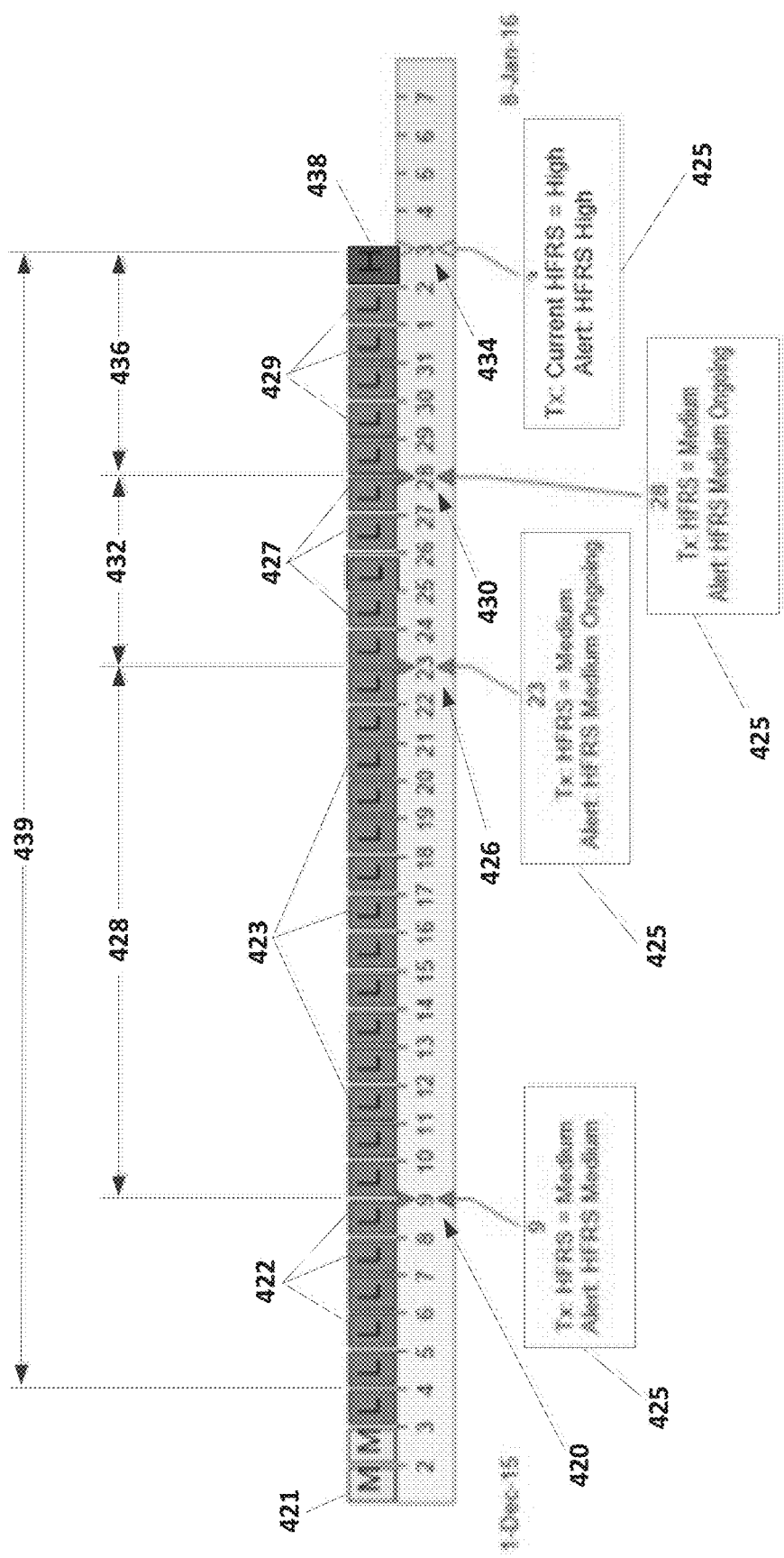

In the example illustrated in FIG. 13C, a data transmission 420 from a remote monitoring device, such as IMD 16, was received by the external device 114 on Dec. 9, 2015. Upon receipt of the data transmission 420, processor(s) 118 of external device 114 acquires patient metrics from the remote monitoring device and determines a daily HFRS 422 of either high H, medium M, or low L for each day during a time period extending subsequent to a previous transmission, or as in the example of FIG. 13C, subsequent to the date that the HFRS differentiation algorithm of the present disclosure was enabled in the external device 114, i.e., Dec. 1, 2015, to the day of receipt of the current data transmission 420, using the patient metric trends described above, for example.

External device 114 stores each daily HFRS 4 of either high H, medium M, or low L determined during the time period extending subsequent to a previous data transmission within memory 119. External device 114 then determines a maximum daily HFRS of each daily HFRS determined for each day within a lookback window occurring prior to receipt of the current data transmission 420, as described above. In the example of FIG. 13C, the maximum daily HFRS for the current data transmission 420 is determined to be HFRS 421, which was determined to have a daily HFRS of medium M. Since the maximum daily HFRS, i.e., daily HFRS 421, that occurred during the current 30 day lookback window was medium M, the external device 114 determines that the HFRS for the current data transmission 420 is a medium M HFRS. In addition, since neither an HFRS medium alert or an HFRS ongoing alert was generated for a data transmission received prior to the current received data transmission 420, the external device 114 determines that an HFRS alert for the current data transmission 420 is a medium HFRS alert. Therefore, the external device 114 generates and stores a display 425 associated with the current received data transmission 420 indicating one or both of the determination that the HFRS associated with the current received data transmission 420 is a medium HFRS, "Current HFRS=Medium" and the HFRS alert associated with the current received data transmission 520 is a medium HFRS alert, "Alert: HFRS Medium", which may then be displayed by the external device 114 for subsequent review by a clinician.

After generating and storing the display 425 associated with data transmission 420, external device 114 waits for receipt of a next data transmission from the remote monitoring device, which, in the example illustrated in FIG. 13C, is a data transmission 426 received on Dec. 23, 2015. Upon receipt of the next data transmission 426, the external device 114 determines a daily HFRS 423 of either high H, medium M, or low L for each day during a time period 428 subsequent to the previous data transmission 420 and up to the day of receipt of the current data transmission 426. In the example of FIG. 13C, upon receipt of the current data transmission 426, the external device 114 determines a daily HFRS of low L for each day during the time period 428 between the day of receipt of the previous received data transmission 420 and receipt of the current data transmission 424.

External device 114 stores each daily HFRS 423 of either high H, medium M, or low L determined during the time period 428 extending subsequent to a previous data transmission within memory 119. External device 114 then determines a maximum daily HFRS of each daily HFRS determined within a lookback window prior to the current received data transmission 426. In the example of FIG. 13C, since the maximum daily HFRS for the current data transmission 426 is determined to be daily HFRS 421, which was determined to have a daily HFRS of medium M. Since the maximum daily HFRS was determined to be medium M, the external device 114 determines that the HFRS for the current received data transmission 434 is a medium HFRS. In addition, since either an HFRS medium alert or an HFRS medium ongoing alert was generated for a data transmission received prior to the current received data transmission 434, the external device 114 determines that an HFRS alert for the current data transmission 420 is a medium ongoing HFRS alert. Therefore, the external device 114 generates and stores a display 425 associated with the current received data transmission 426 indicating one or both of the determination that the HFRS associated with the current received data transmission 426 is a new medium HFRS, "Current HFRS=Medium" and the HFRS alert associated with the current received data transmission 426 is a medium ongoing HFRS alert, "Alert: HFRS Medium Ongoing", which may then be displayed by the external device 114 for subsequent review by a clinician.

After generating and storing the display 425 associated with received data transmission 426, external device 114 waits for receipt of a next data transmission from the remote monitoring device, which, in the example illustrated in FIG. 13C, is a data transmission 430 received on Dec. 28, 2015. Upon receipt of the next data transmission 430, the external device 114 determines a daily HFRS 427 of high H, medium M, or low L for each day during a time period 432 subsequent to the previous data transmission 426 and up to the current received data transmission 430.

External device 114 stores each daily HFRS 427 of either high H, medium M, or low L determined during the time period 432 extending subsequent to a previous data transmission within memory 119. External device 114 then determines a maximum daily HFRS of each daily HFRS determined for each day within a day lookback window prior to the current received data transmission 430, as described above. Since the maximum daily HFRS for the current data transmission is determined to be daily HFRS 421, which occurred on Dec. 1, 2015, a maximum daily HFRS of medium M is determined to have occurred during the lookback window for the current received data transmission 430, and therefore the external device 114 determines that the daily HFRS associated with the current received data transmission 430 is a medium M HFRS. Since either an HFRS medium alert or an HFRS ongoing alert was generated for a data transmission received prior to the current received data transmission 430, the external device 114 determines that an HFRS alert for the current data transmission 420 is a medium ongoing HFRS alert. Therefore, the external device 114 generates and stores a display 425 associated with the current received data transmission 430 indicating one or both of the determination that the HFRS associated with the current received data transmission 430 is a medium HFRS, "Current HFRS=Medium" and the HFRS alert associated with the current received data transmission 430 is a medium ongoing HFRS alert, "Alert: HFRS Medium Ongoing", which may then be displayed by the external device 114 for subsequent review by a clinician.

After generating and storing the display 425 associated with the current data transmission 430, external device 114 waits for receipt of a next data transmission from the remote monitoring device, which, in the example illustrated in FIG. 13C, is data transmission 434 received on Jan. 3, 2016. Upon receipt of the next data transmission 434, the external device 114 determines a daily HFRS 429 of either high H, medium M, or low L for each day 436 during a time period 429 subsequent to the previous data transmission 430 and up to receipt of the next, i.e., current data transmission 434.

External device 114 stores each daily HFRS 429 of either high H, medium M, or low L determined during the time period 439 extending subsequent to a previous data transmission within memory 119. External device 114 then determines a maximum daily HFRS of the daily HFRS determined for each day within a lookback window 439 occurring prior to the current received data transmission 434, i.e., between Dec. 4, 2015-Jan. 3, 2016. In the example of FIG. 13C, the maximum daily HFRS that occurs in the lookback window 439 for the current received data transmission 434 was determined to be daily HFRS 438, which occurred on Jan. 2, 2016 and was determined to be high H.

Therefore, the external device 114 determines that the HFRS for the current received data transmission 434 is a high HFRS. In addition, since neither an HFRS high alert or an HFRS high ongoing alert was generated during the lookback window 439 for the current received data transmission 434, the external device 114 determines that an HFRS alert for the current data transmission 420 is a high HFRS alert. Therefore, the external device 114 generates and stores a display 425 associated with the current received data transmission 434 indicating one or both the determination that the HFRS associated with the current received data transmission 434 is a high HFRS, "Current HFRS=High" and the HFRS alert associated with the current received data transmission 434 is a high HFRS alert, "Alert: HFRS High", which may then be displayed by the external device 114 for subsequent review by a clinician.

Figure 13D:
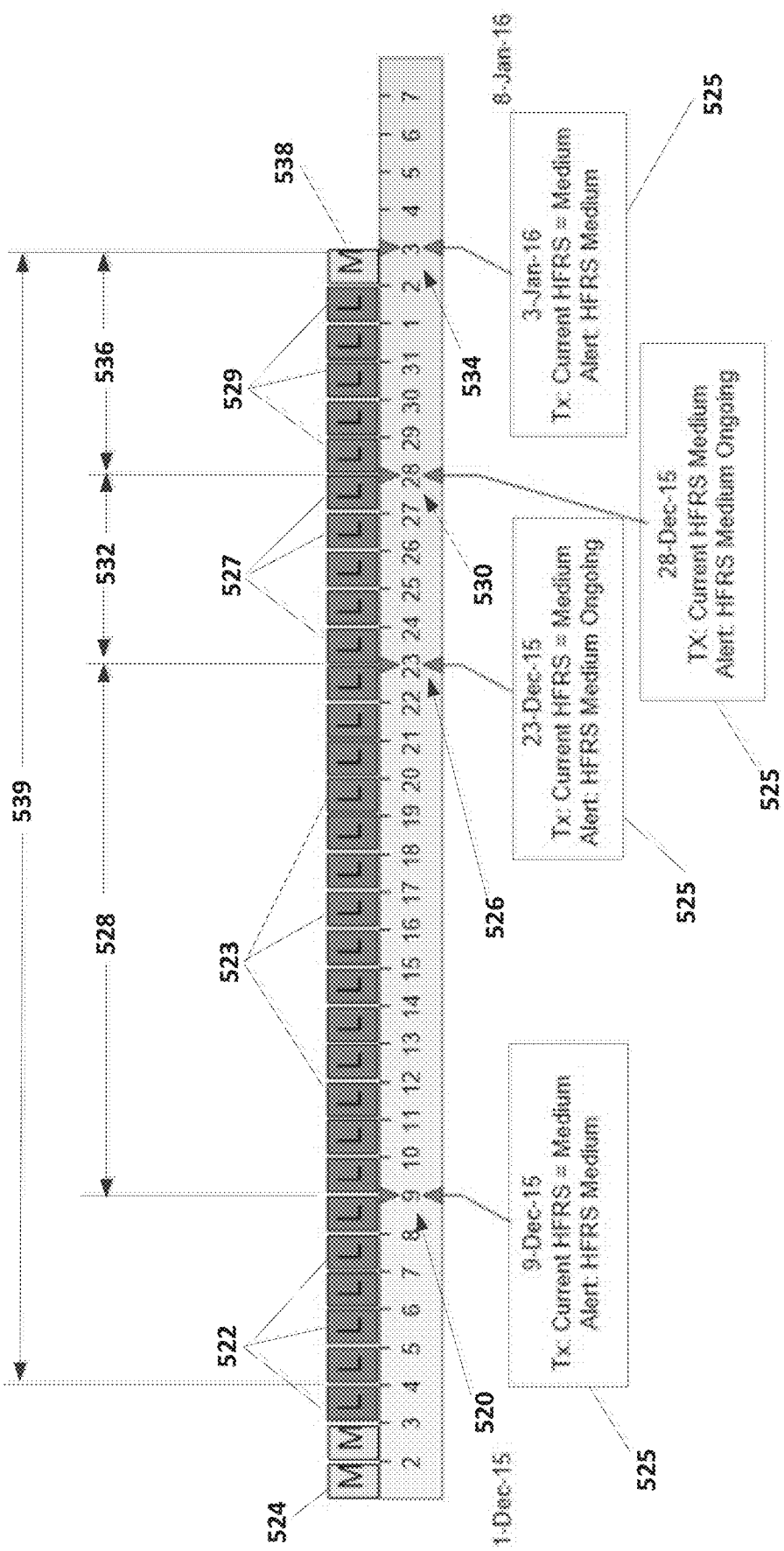

In the example illustrated in FIG. 13D, a data transmission 520 from a remote monitoring device, such as IMD 16, was received by the external device 114 on Dec. 9, 2015. Upon receipt of the data transmission 420, processor(s) 118 of external device 114 acquires patient metrics from the remote monitoring device and determines a daily HFRS 522 of either high H, medium M, or low L for each day during a time period extending subsequent to a previous transmission, or as in the example of FIG. 13A, subsequent to the date that the HFRS differentiation algorithm of the present disclosure was enabled in the external device 114, i.e., Dec. 1, 2015, to the day of receipt of the current data transmission 520, using the patient metric trends described above, for example.

External device 114 then determines a maximum daily HFRS of each daily HFRS determined for each day within a lookback window occurring prior to receipt of the current data transmission 520. In one example, the lookback window may be a 30 day lookback window. In the example of FIG. 13D, the maximum daily HFRS is determined to be HFRS 524, which occurred on Dec. 1, 2015, and the current data transmission 520 is the first data transmission to be received by external device since the HFRS differentiation algorithm of the present disclosure was enabled on the external device 114, i.e., on Dec. 1, 2015. Since the maximum daily HFRS, i.e., daily HFRS 524, that occurred during the current 30 day lookback window was medium M, the external device 114 determines that the HFRS for the current data transmission 520 is a medium M HFRS. In addition, since the maximum daily HFRS, i.e., daily HFRS 524, that occurred during the current 30 day lookback window was medium M and did not occur during receipt of a previous data transmission, the external device 114 determines that an HFRS alert for the current data transmission 520 is a medium HFRS alert, rather than medium ongoing. Therefore, the external device 114 generates and stores a display 525 associated with the current received data transmission 520 indicating the determination that the HFRS associated with the current received data transmission 520 is a medium HFRS, "Current HFRS=Medium" and the HFRS alert associated with the current received data transmission 520 is a medium HFRS alert, "Alert: HFRS Medium", which may then be displayed by the external device 114 for subsequent review by a clinician.

After generating display 525 associated with data transmission 520, external device 114 waits for receipt of a next data transmission from the remote monitoring device, which, in the example illustrated in FIG. 13D, is a data transmission 526 received on Dec. 23, 2015. Upon receipt of the next data transmission 526, the external device 114 determines a daily HFRS 523 of either high H, medium M, or low L for each day during a time period 528 subsequent to the previous data transmission 520 and up to the day of receipt of the current data transmission 526. In the example of FIG. 13D, upon receipt of the current data transmission 526, the external device 114 determines a daily HFRS of low L for each day during the time period 528 between the day of receipt of the previous received data transmission 520 and receipt of the current data transmission 524.

External device 114 stores each daily HFRS 523 of either high H, medium M, or low L determined during the time period 528 extending subsequent to a previous data transmission within memory 119. External device 114 then determines a maximum daily HFRS of each daily HFRS determined within a 30 day lookback window prior to the current received data transmission 526. In the example of FIG. 13D, since the maximum daily HFRS for the current data transmission 526 is determined to be daily HFRS 524, which occurred on Dec. 1, 2015, a maximum daily HFRS of medium M occurred during the current 30 day lookback window. Therefore, the external device 114 determines that the daily HFRS associated with the current received data transmission 526 is a medium M HFRS. In addition, since the maximum daily HFRS for the current received data transmission 526, i.e., daily HFRS 524, occurred during receipt of a previous data transmission 520, external device 114 determines that an HFRS alert for the current received data transmission 526 is a medium ongoing HFRS alert. Therefore, the external device 114 generates and stores a display 525 associated with the current received data transmission 526 indicating the determination that the HFRS associated with the current received data transmission 526 is a medium HFRS, "Current HFRS=Medium" and the HFRS alert associated with the current received data transmission 526 is a medium ongoing HFRS alert, "Alert: HFRS Medium Ongoing", which may then be displayed by the external device 114 for subsequent review by a clinician.

After generating the display 525 associated with received data transmission 526, external device 114 waits for receipt of a next data transmission from the remote monitoring device, which, in the example illustrated in FIG. 13D, is a data transmission 530 received on Dec. 28, 2015. Upon receipt of the next data transmission 530, the external device 114 determines a daily HFRS 527 of high H, medium M, or low L for each day during a time period 532 subsequent to the previous data transmission 526 and up to the current received data transmission 530.

External device 114 stores each daily HFRS 527 of either high H, medium M, or low L determined during the time period 532 extending subsequent to a previous data transmission within memory 119. External device 114 then determines a maximum daily HFRS of each daily HFRS determined for each day within a 30 day lookback window prior to the current received data transmission 530. Since the maximum daily HFRS for the current data transmission is determined to be daily HFRS 524, which occurred on Dec.

1, 2015, a daily HFRS of medium M is determined to have occurred during the current 30 day lookback window for the current received data transmission 530. Therefore, the external device 114 determines that the maximum daily HFRS associated with the current received data transmission 530 is a medium M HFRS. In addition, since the maximum daily HFRS for the current received data transmission 530, i.e., daily HFRS 524, occurred during receipt of a previous data transmission 520, external device 114 determines that an alert for the current received data transmission 530 is a medium ongoing event alert. Therefore, the external device 114 generates and stores a display 525 associated with the current received data transmission 530 indicating the determination that the HFRS associated with the current received data transmission 530 is a medium event, "Current HFRS=Medium" and the alert associated with the current received data transmission 530 is a medium ongoing alert, "Alert: HFRS Medium Ongoing", which may then be displayed by the external device 114 for subsequent review by a clinician.

After generating the display 525 associated with data transmission 530, external device 114 waits for receipt of a next data transmission 534 from the remote monitoring device, which, in the example illustrated in FIG. 13D, is received on Jan. 3, 2016. Upon receipt of the next data transmission 534, the external device 114 determines a daily HFRS 529 of either high H, medium M, or low L for each day during a time period 536 subsequent to the previous data transmission 530 and up to receipt of the next, i.e., current data transmission 534.

External device 114 stores each daily HFRS 529 of either high H, medium M, or low L determined during the time period 536 extending subsequent to a previous data transmission within memory 119. External device 114 then determines a maximum daily HFRS of the daily HFRS determined for each day within a 30 day lookback window 539 occurring prior to the current received data transmission 534, i.e., between Dec. 4, 2015-Jan. 3, 2016. In the example of FIG. 13D, the maximum daily HFRS for the current received data transmission 534 that occurred during the lookback window 539 was determined to be daily HFRS 538, which occurred on Jan. 2, 2016 and was determined to be medium M. Therefore, the external device 114 determines that the HFRS for the current received data transmission 534 is a medium HFRS. In addition, since the maximum daily HFRS, i.e., daily HFRS 538, that occurred during the current 30 day lookback window 539 was medium M and did not occur during receipt of a previous data transmission, the external device 114 determines that an HFRS alert for the current data transmission 534 is a medium HFRS alert, rather than a medium ongoing HFRS alert. Therefore, the external device 114 generates and stores a display 525 associated with the current received data transmission 534 indicating the determination that the HFRS associated with the current received data transmission 534 is a medium HFRS, "Current HFRS=Medium" and the HFRS alert associated with the current received data transmission 534 is a medium HFRS, "Alert: HFRS Medium", which may then be displayed by the external device 114 for subsequent review by a clinician.

According to another example, if the daily HFRS 538 on Jan. 2, 2016 was determined to be high "H" rather than medium "M", as illustrated in FIG. 13D, the maximum daily HFRS for the current received data transmission 434 would be determined to be high "H" rather than medium "M", since the maximum daily HFRS during the lookup window 539 would be the HFRS of high determined for daily HFRS 538. As a result, the external device 114 would generate and store the display 525 associated with the current received data transmission 534 indicating the determination that the HFRS associated with the current received data transmission 534 is a high HFRS, "Current HFRS=High" and the HFRS alert associated with the current received data transmission 534 is a high HFRS alert, "Alert: HFRS High", which may then be displayed by the external device 114 for subsequent review by a clinician.

Similarly, according to another example, if the daily HFRS 538 on Jan. 2, 2016 was determined to be low "L" rather than Medium "M" as illustrated in FIG. 13D, the maximum daily HFRS for the current received data transmission 534 would be determined to be low "L" rather than medium "M", since only a daily HFRS of "L" is determined to occur for each day during the 30 day lookback window from receipt of the current data transmission 534. As a result, the external device 114 would generate and store the display 525 associated with the current received data transmission 534 indicating the determination that the HFRS associated with the current received data transmission 534 is a low HFRS, "Current HFRS=Low" and the HFRS alert associated with the current received data transmission 534 is a low HFRS alert, "Alert: HFRS Low", which may then be displayed by the external device 114 for subsequent review by a clinician.

In the example illustrated in FIG. 13D, a data transmission 520 from a remote monitoring device, such as IMD 16 for example, was received by the external device 114 on Dec. 9, 2015. Upon receipt of the data transmission 520, one or more processor(s) 118 of external device 114 determines a daily HFRS 522 of either high H, medium M, or low L for each day during a time period extending subsequent to a previous data transmission, or as in the example of FIG. 13D, if there is no data previous transmission, the time period extends subsequent to the date that the HFRS differentiation algorithm of the present disclosure was enabled in the external device 114, i.e., Dec. 1, 2015, to the day of receipt of the current data transmission 520, using the patient metric trends described above, for example.

External device 114 stores each daily HFRS 522 of either high H, medium M, or low L determined during the time period extending subsequent to a previous data transmission within memory 119. External device 114 then determines a maximum daily HFRS of each daily HFRS determined for each day within a lookback window occurring prior to receipt of the current data transmission 520. In one example, the lookback window may be a 30 day lookback window, and if it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13D, the maximum daily HFRS for the current data transmission 520 is determined to be HFRS 524, which was determined to have a daily HFRS of medium M.

Since the maximum daily HFRS was determined to be medium M, the external device 114 determines that the HFRS for the current data transmission 520 is HFRS of medium M. In addition, since neither an HFRS medium H alert nor an HFRS medium ongoing alert was generated for a data transmission received prior to the current received data transmission 520 (in the example of FIG. 13D, there was no data transmission received prior to the current received data transmission 520 since the current data transmission 520 is the initial data transmission received since the HFRS differentiation algorithm feature was enabled), the external device 114 determines that an HFRS alert for the current data transmission 520 is a medium HFRS alert, rather than a medium ongoing HFRS alert. Therefore, the external device 114 generates and stores a display 525 associated with the current received data transmission 520 indicating one or both of the determination that the HFRS associated with the current received data transmission 520 is a medium HFRS, "Current HFRS=Medium" and the HFRS alert associated with the current received data transmission 520 is a medium HFRS alert, "Alert: HFRS Medium", which may then be displayed by the external device 114 for subsequent review by a clinician.

After generating and storing the display 525 associated with data transmission 520, external device 114 waits for receipt of a next data transmission from the remote monitoring device, which, in the example illustrated in FIG. 13D, is a data transmission 526 received on Dec. 23, 2015. Upon receipt of the next data transmission 526, the external device 114 determines a daily HFRS 523 of either high H, medium M, or low L for each day during a time period 523 subsequent to the previous data transmission 520 and up to receipt of the current data transmission 526.

External device 114 stores each daily HFRS 523 of either high H, medium M, or low L determined during the time period 523 extending subsequent to a previous data transmission within memory 119. External device 114 then determines a maximum daily HFRS of each daily HFRS determined within a lookback window prior to the current received data transmission 526. Assuming a 30 day lookback window, since it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13D, the maximum daily HFRS during the lookback window for the current data transmission 526 is again determined to be daily HFRS 524. Since the maximum daily HFRS in the lookback window for the current data transmission 530 was determined to be a HFRS of medium M, the external device 114 determines that the maximum daily HFRS associated with the current received data transmission 526 is a medium M HFRS. In addition, since an HFRS medium alert was generated for data transmission 520 received prior to the current data transmission 526, external device 114 determines that an HFRS alert for the current received data transmission 526 is a medium ongoing alert. Therefore, the external device 114 generates and stores a display 525 associated with the current received data transmission 526 indicating one or both of the determination that the HFRS associated with the current received data transmission 526 is a medium HFRS, "Current HFRS=Medium" and the HFRS alert associated with the current received data transmission 526 is a medium ongoing alert, "Alert: HFRS Medium Ongoing", which may then be displayed by the external device 114 for subsequent review by a clinician.

After generating and storing the display 525 associated with received data transmission 526, external device 114 waits for receipt of a next data transmission from the remote monitoring device, which, in the example illustrated in FIG. 13D, is a data transmission 530 received on Dec. 28, 2015. Upon receipt of the next data transmission 530, the external device 114 determines a daily HFRS 527 of high H, medium M, or low L for each day during a time period 532 subsequent to the previous data transmission 526 and up to receipt of the current data transmission 530. In the example of FIG. 13D, upon receipt of the current data transmission 530, the external device 114 determines a daily HFRS of low L for each day during the time period 532 between the day of receipt of the previous received data transmission 526 and receipt of the current data transmission 530.

External device 114 stores each daily HFRS 527 of either high H, medium M, or low L determined during the time period 532 extending subsequent to a previous data transmission within memory 119. External device 114 then determines a maximum daily HFRS of each daily HFRS determined for each day within a lookback window prior to the current received data transmission 530. Assuming a 30 day lookback window, since it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13D, the maximum daily HFRS within the lookback window for the current data transmission is determined to be daily HFRS 524, which was determined to have a daily HFRS of medium M. Since the maximum daily HFRS is determined to be medium M, the external device 114 determines that the daily HFRS associated with the current received data transmission 530 is a medium M HFRS. In addition, since either an HFRS medium alert or an HFRS medium ongoing alert was generated for a previous data transmission, i.e., for previous data transmission 520 and previous data transmission 526, respectively, the external device 114 determines that an HFRS alert for the current received data transmission 530 is a medium ongoing HFRS alert. Therefore, the external device 114 generates and stores a display 525 associated with the current received data transmission 530 indicating one or both of the determination that the HFRS associated with the current received data transmission 530 is a medium HFRS, "Current HFRS=Medium" and the HFRS alert associated with the current received data transmission 530 is a medium ongoing HFRS alert, "Alert: HFRS Medium Ongoing", which may then be displayed by the external device 114 for subsequent review by a clinician.

After generating and storing the display 525 associated with data transmission 530, external device 114 waits for receipt of a next data transmission from the remote monitoring device, which, in the example illustrated in FIG. 13D, is data transmission 534 received on Jan. 3, 2016. Upon receipt of the next data transmission 534, the external device 114 determines a daily HFRS 529 of either high H, medium M, or low L for each day during a time period 536 subsequent to the previous data transmission 530 and up to receipt of the current received data transmission 534.

External device 114 stores each daily HFRS 529 of either high H, medium M, or low L determined during the time period 536 extending subsequent to a previous data transmission within memory 119. External device 114 then determines a maximum daily HFRS of the daily HFRS determined for each day within a lookback window 539 prior to the current received data transmission 534, i.e., between Dec. 4, 2015-Jan. 3, 2016. In the example of FIG. 13D, the maximum daily HFRS for the current received data transmission 534 was determined to be daily HFRS 538, which occurred on Jan. 2, 2016 and was determined to be medium M. Therefore, since the maximum daily HFRS within the lookback window 539 was determined to be medium M, the external device 114 determines that the HFRS for the current received data transmission 534 is a medium HFRS. In addition, since either an HFRS medium alert or an HFRS medium ongoing alert was generated for a previous data transmission, i.e., previous transmission 520, previous data transmission 526 and previous data transmission 530, the external device 114 determines that an HFRS alert for the current data transmission 534 is a medium HFRS alert. Therefore, the external device 114 generates and stores a display 525 associated with the current received data transmission 534 indicating one or both of the determination that the HFRS associated with the current received data transmission 534 is a medium HFRS, "Current HFRS=Medium" and the HFRS alert associated with the current received data transmission 534 is a medium HFRS alert, "Alert: HFRS Medium", which may then be displayed by the external device 114 for subsequent review by a clinician.

According to another example, if the daily HFRS 538 on Jan. 2, 2016 was determined to be high H rather than medium M, as illustrated in FIG. 13D, the maximum daily HFRS for the current received data transmission 534 in FIG. 13D would be determined to be high H rather than medium M, since the maximum daily HFRS during the lookup window 539 would be the HFRS of high H determined for daily HFRS 538. As a result, the external device 114 would determine that the HRFS for the current data transmission 534 is high H, and that the HFRS alert was a high HFRS alert since no HFRS high or HFRS high ongoing was generated during the lookback window 539. Therefore, the external device 114 would generate and store the display 525 associated with the current received data transmission 534 to indicate one or both of the determination that the HFRS associated with the current received data transmission 534 is a high HFRS, "Current HFRS=High" and the HFRS alert associated with the current received data transmission 534 is a high HFRS alert, "Alert: HFRS High", which may then be displayed by the external device 114 for subsequent review by a clinician.

In the example illustrated in FIG. 13D, or in the example where the daily HFRS 538 is determined to be high H, the external device 114 could further differentiate the HFRS for the current data transmission 534 by determining that since the maximum daily HFRS occurred during the current data transmission 534, i.e., during time window 536 associated with the current data transmission 534, the HFRS for the current data transmission 534 is a new medium HFRS or a new high HFRS, respectively. As a result, the external device 114 would generate and store the display to indicate that the HFRS for the current data transmission 534 is a new medium, "HFRS=Medium New", or to indicate that the HFRS for the current data transmission 534 is a new high, "HFRS=High New", respectively.

Similarly, according to another example, if the daily HFRS 538 on Jan. 2, 2016 was determined to be low "L" rather than medium "M" as illustrated in FIG. 13D, the maximum daily HFRS for the current received data transmission 534 would be determined to be low "L" rather than medium "M", since maximum daily HFRS during the lookback table 539 would be a daily HFRS of low. As a result, the external device 114 would determine that the HRFS for the current data transmission 534 is low L, and that the HFRS alert was a low HFRS alert. Therefore, the external device 114 would generate and store the display 525 associated with the current received data transmission 534 indicating one or both of the determination the HFRS associated with the current received data transmission 534 is a low HFRS, "Current HFRS=Low" and the HFRS alert associated with the current received data transmission 534 is a low HFRS alert, "Alert: HFRS Low", which may then be displayed by the external device 114 for subsequent review by a clinician.

Figure 13E:
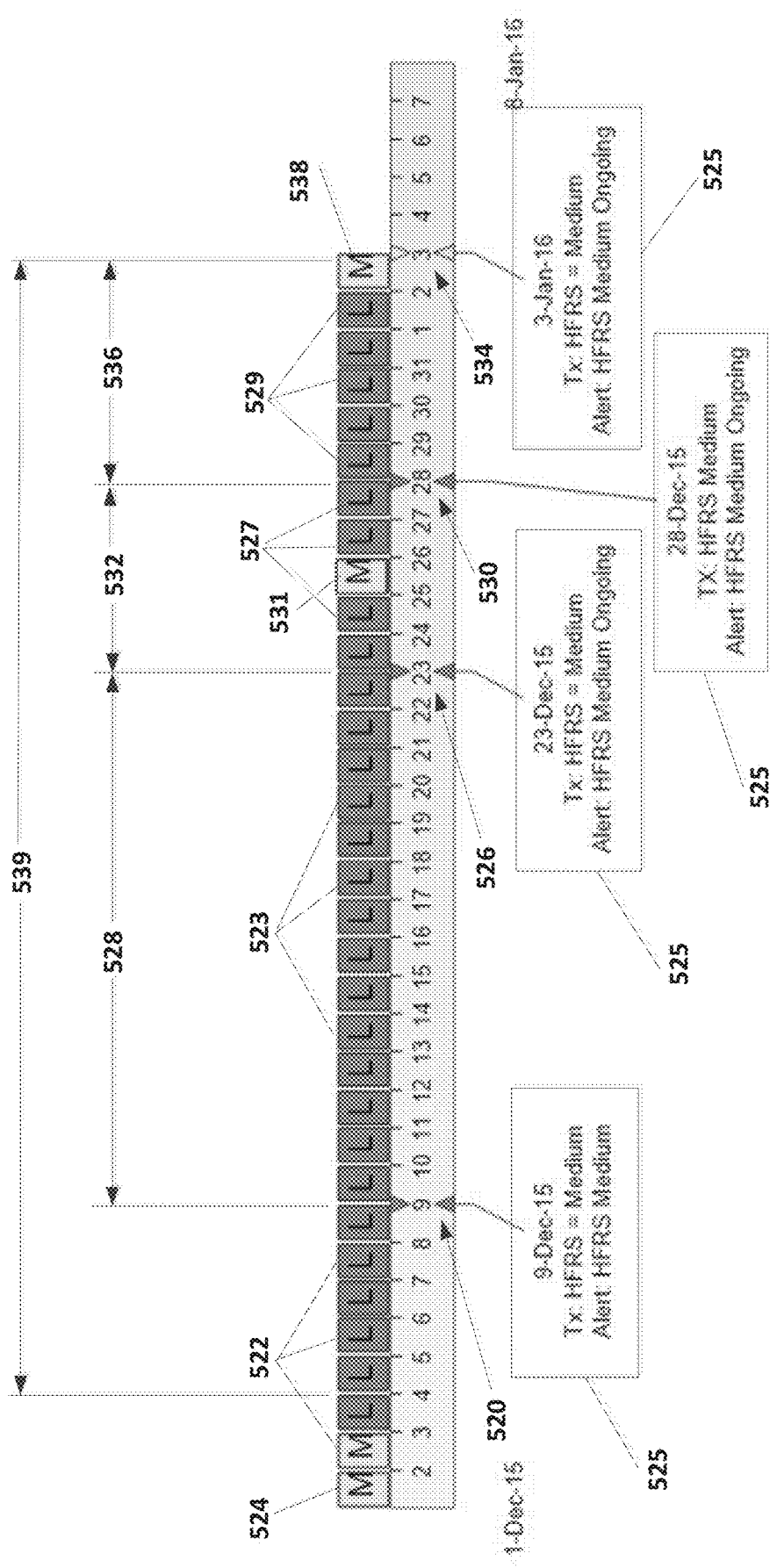

The example illustrated in FIG. 13E is similar to the example illustrated in FIG. 13D with the exception that during the receipt of a data transmission 530 on Dec. 28, 2015, the daily HFRS 531 for Dec. 25, 2015 is determined to be medium "M" rather low "L". In the example of FIG. 13 B, after generating the display 525 associated with received data transmission 526, external device 114 waits for receipt of a next data transmission from the remote monitoring device, which, in the example illustrated in FIG. 13E, is data transmission 530 received on Dec. 28, 2015. Upon receipt of the next data transmission 530, the external device 114 determines a daily HFRS 527 of high H, medium M, or low L for each day during a time period 532 subsequent to the previous data transmission 526 and up to receipt of the current data transmission 530. In the example of FIG. 13E, a daily HFRS of medium M was determined for daily HFRS 531 occurring during the time period 532 on Dec. 25, 2015.

External device 114 stores each daily HFRS 527 of either high H, medium M, or low L determined during the time period 532 extending subsequent to a previous data transmission within memory 119. External device 114 then determines a maximum daily HFRS of each daily HFRS determined for each day within a lookback window prior to the current received data transmission 530. In the example of FIG. 13E, the maximum daily HFRS for the current data transmission 530 is determined to be daily HFRS 524 (HFRS 524 is determined to be greater than HFRS 531), which occurred on Dec. 1, 2015, and therefore a daily HFRS of medium M is determined to have occurred during the current lookback window for the current received data transmission 530. Since the maximum daily HFRS was determined to be medium, the external device 114 determines that the HFRS for the current data transmission 530 is a medium HFRS. In addition, since either an HFRS medium alert or an HFRS medium ongoing alert was received for a previous data transmission, i.e., previous data transmission 520 and previous data transmission 526, respectively, external device 114 determines that an HFRS alert for the current received data transmission 530 is a medium ongoing HFRS alert. Therefore, the external device 114 generates and stores a display 525 associated with the current received data transmission 530 indicating one or both of the determination that the HFRS associated with the current received data transmission 530 is a medium HFRS, "Current HFRS=Medium" and the HFRS alert associated with the current received data transmission 530 is a medium ongoing HFRS alert, "Alert: HFRS Medium Ongoing", which may then be displayed by the external device 114 for subsequent review by a clinician.

According to another example, the maximum daily HFRS for the current data transmission 530 in FIG. 13E is determined to be daily HFRS 531 (HFRS 531 is determined to be greater than HFRS 524), which was determined to have a daily HFRS of medium M. Since the maximum daily HFRS was determined to be medium M, the external device 114 determines that the HFRS for the current received data transmission 530 is a medium HFRS. In addition, since either an HFRS medium alert or an HFRS medium ongoing alert was received for a previous data transmission, i.e., previous data transmission 520 and previous data transmission 526, respectively, external device 114 determines that an HFRS alert for the current received data transmission 530 is a medium ongoing HFRS alert. Therefore, the external device 114 would generate and store a display 525 associated with the current received data transmission 530 indicating one or both of the determination that the HFRS associated with the current received data transmission 530 is a medium HFRS, "Current HFRS=Medium" and the HFRS alert associated with the current received data transmission 530 is a medium ongoing HFRS alert, "Alert: HFRS Medium Ongoing", which may then be displayed by the external device 114 for subsequent review by a clinician.

After generating and storing the display 525 associated with data transmission 530, external device 114 waits for receipt of a next data transmission from the remote monitoring device, which, in the example illustrated in FIG. 13E, is data transmission 534, received on Jan. 3, 2016. Upon receipt of the next data transmission 534, the external device 114 determines a daily HFRS 529 of either high H, medium M, or low L for each day during a time period 536 subsequent to the previous data transmission 530 and up to receipt of the current data transmission 534.

External device 114 stores each daily HFRS 529 of either high H, medium M, or low L determined during the time period 436 extending subsequent to a previous data transmission within memory 119. External device 114 then determines a maximum daily HFRS of the daily HFRS determined for each day within a lookback window 539 prior to the current received data transmission 534, i.e., between Dec. 4, 2015-Jan. 3, 2016. In the example of FIG. 13E, the maximum daily HFRS was determined to be daily HFRS 531 (daily HFRS 531 is greater than daily HFRS 538), which occurred on Dec. 25, 2015 and was determined to be medium M. Since the maximum daily HFRS determined during the lookback window 539 was determined to be medium M, the external device 114 determines that the HFRS for the current received data transmission 534 is a medium HFRS. In addition, since either an HFRS medium alert or an HFRS medium ongoing alert was determined for a previous data transmission within the lookback window 539, i.e., a medium ongoing HFRS alert was determined for previous data transmission 526 and 530, external device 114 determines that an HFRS alert for the current received data transmission 530 is a medium ongoing HFRS alert. Therefore, the external device 114 generates and stores a display 525 associated with the current received data transmission 534 indicating one or both of the determination that the HFRS associated with the current received data transmission 534 is a medium HFRS, "Current HFRS=Medium" and the HFRS alert associated with the current received data transmission 534 is a medium ongoing HFRS alert, "Alert: HFRS Medium Ongoing", which may then be displayed by the external device 114 for subsequent review by a clinician.

According to another example, the maximum daily HFRS for the current data transmission 534 may be determined to be daily HFRS 538 (HFRS 538 is determined to be greater than HFRS 531), which occurred on Jan. 2, 2016, and therefore a daily HFRS of medium is determined to have occurred during the lookback window 539 for the current received data transmission 534. Since the maximum daily HFRS was determined to be medium M, the external device 114 determines that the HFRS for the current received data transmission 538 is a medium HFRS. In addition, since either an HFRS medium alert or an HFRS medium ongoing alert was determined for a previous data transmission, i.e., a medium HFRS alert was determined for previous data transmission 520, and a medium ongoing HFRS alert previous was determined for previous data transmission 526 and 530, external device 114 determines that an HFRS alert for the current received data transmission 530 is a medium ongoing HFRS alert. Therefore, the external device 114 would generate and store a display 525 associated with the current received data transmission 534 indicating the determination that the HFRS associated with the current received data transmission 534 is a medium HFRS, "Current HFRS="Medium" and the HFRS alert associated with the current received data transmission 534 is a medium ongoing HRFS alert, "Alert: HFRS Medium Ongoing, which may then be displayed by the external device 114 for subsequent review by a clinician.

In the example illustrated in FIG. 13E, the external device 114 could further differentiate the HFRS for the current data transmission 534 by determining that since the maximum daily HFRS occurred during the current data transmission 534, i.e., during time window 536 associated with the current data transmission 534, the HFRS for the current data transmission 534 is a new medium HFRS. As a result, the external device 114 would generate and store the display to indicate that the HFRS for the current data transmission 534 is a new medium, "HFRS=Medium New". In the same way, the external device 114 could further differentiate the HFRS for the current data transmission 530 by determining that since the maximum daily HFRS occurred during the current data transmission 530, i.e., during time window 532 associated with the current data transmission 530, the HFRS for the current data transmission 530 is a new medium HFRS. As a result, the external device 114 would generate and store the display to indicate that the HFRS for the current data transmission 530 is a new medium, "HFRS=Medium New".

Figure 13F:
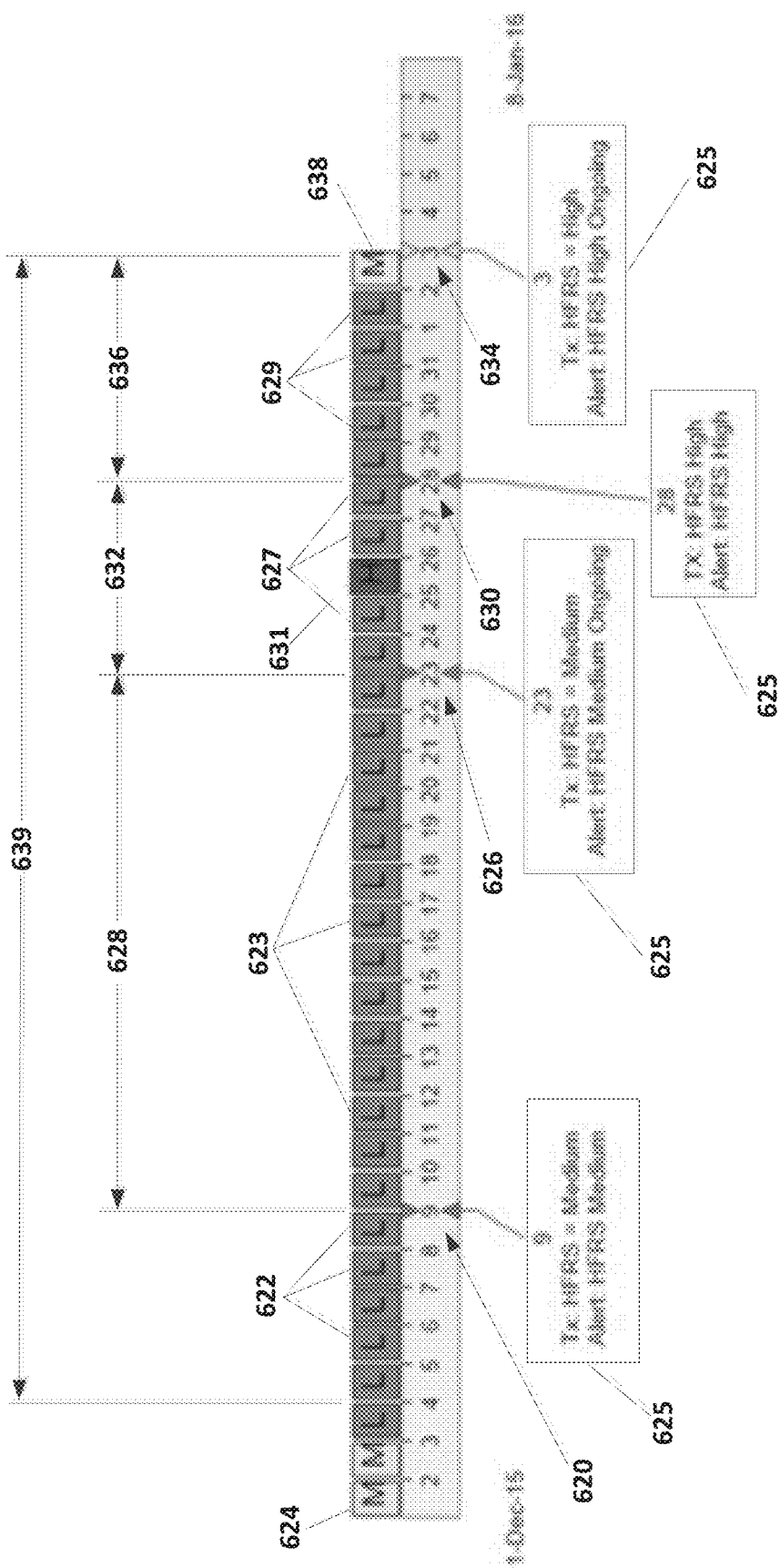

FIG. 13F is similar to the example illustrated in FIG. 13E with the exception that during the receipt of a data transmission 630 on Dec. 28, 2015 in FIG. 13F, the daily HFRS 631 for Dec. 25, 2015 is determined to be medium "H" rather than low "M" as in the example of FIG. 13E. As illustrated in FIG. 13F, after generating and storing the display 625 associated with received data transmission 626, external device 114 waits for receipt of a next data transmission from the remote monitoring device, which, in the example illustrated in FIG. 13F, is data transmission 630 received on Dec. 28, 2015. Upon receipt of the next data transmission 630, the external device 114 determines a daily HFRS 627 of high H, medium M, or low L for each day during a time period 632 subsequent to the previous data transmission 626 and up to receipt of the current data transmission 630. In the example of FIG. 13F, a daily HFRS of high H was determined for daily HFRS 631 occurring during the time period 532 on Dec. 25, 2015.

External device 114 stores each daily HFRS 627 of either high H, medium M, or low L determined during the time period 632 extending subsequent to a previous data transmission within memory 119. External device 114 then determines a maximum daily HFRS of each daily HFRS determined for each day within a 30 day lookback window prior to the current received data transmission 630. In the example of FIG. 13F, the maximum daily HFRS for the current data transmission 630 is determined to be daily HFRS 631, which occurred on Dec. 25, 2015, and therefore a maximum daily HFRS of high H is determined to have occurred during the current 30 day lookback window for the current received data transmission 630. As a result, the external device 114 would determine that the HFRS associated with the current received data transmission 630 is a high H HFRS. In addition, since neither an HFRS high alert or an HFRS high ongoing alert was generated during the lookback window associated with the current data transmission 630, the external device 114 determines that an HFRS alert for the current received data transmission 630 is a HFRS high alert rather than a HFRS high ongoing alert. Therefore, the external device 114 would generate and store a display 625 associated with the current received data transmission 630 indicating one or both of the determination that the HFRS associated with the current received data transmission 630 is a high HFRS, "Current HFRS=High" and the HFRS alert associated with the current received data transmission 630 is a high HFRS alert, "Alert: HFRS High", which may then be displayed by the external device 114 for subsequent review by a clinician.

After generating and storing the display 625 associated with data transmission 630, external device 114 waits for receipt of a next data transmission 634 from the remote monitoring device, which, in the example illustrated in FIG. 13F, is received on Jan. 3, 2016. Upon receipt of the next data transmission 634, the external device 114 determines a daily HFRS 629 of either high H, medium M, or low L for each day during a time period 636 subsequent to the previous data transmission 630 and up to receipt of the current data transmission 634.

External device 114 stores each daily HFRS 629 of either high H, medium M, or low L determined during the time period 636 extending subsequent to a previous data transmission within memory 119. External device 114 then determines a maximum daily HFRS of the daily HFRS determined for each day within a 30 day lookback window 639 prior to the current received data transmission 634, i.e., between Dec. 4, 2015-Jan. 3, 2016. Since the maximum daily HFRS for the lookback window 639 was determined to be daily HFRS 631, the external device 114 determines that the HFRS for the current received data transmission 634 is a high HFRS. In addition, since an HFRS high alert was generated during the current lookback window 639 during receipt of a previous data transmission 630, the external device 114 determines that an HFRS alert for the current data transmission 634 is a high ongoing HFRS alert. Therefore, the external device 114 generates and stores a display 625 associated with the current received data transmission 634 indicating one or both of the determination that the HFRS associated with the current received data transmission 634 is a high HFRS, "Current HFRS=High" and the HFRS alert associated with the current received data transmission 634 is a high ongoing HFRS alert, "Alert: HFRS High Ongoing", which may then be displayed by the external device 114 for subsequent review by a clinician.

Figure 13G:
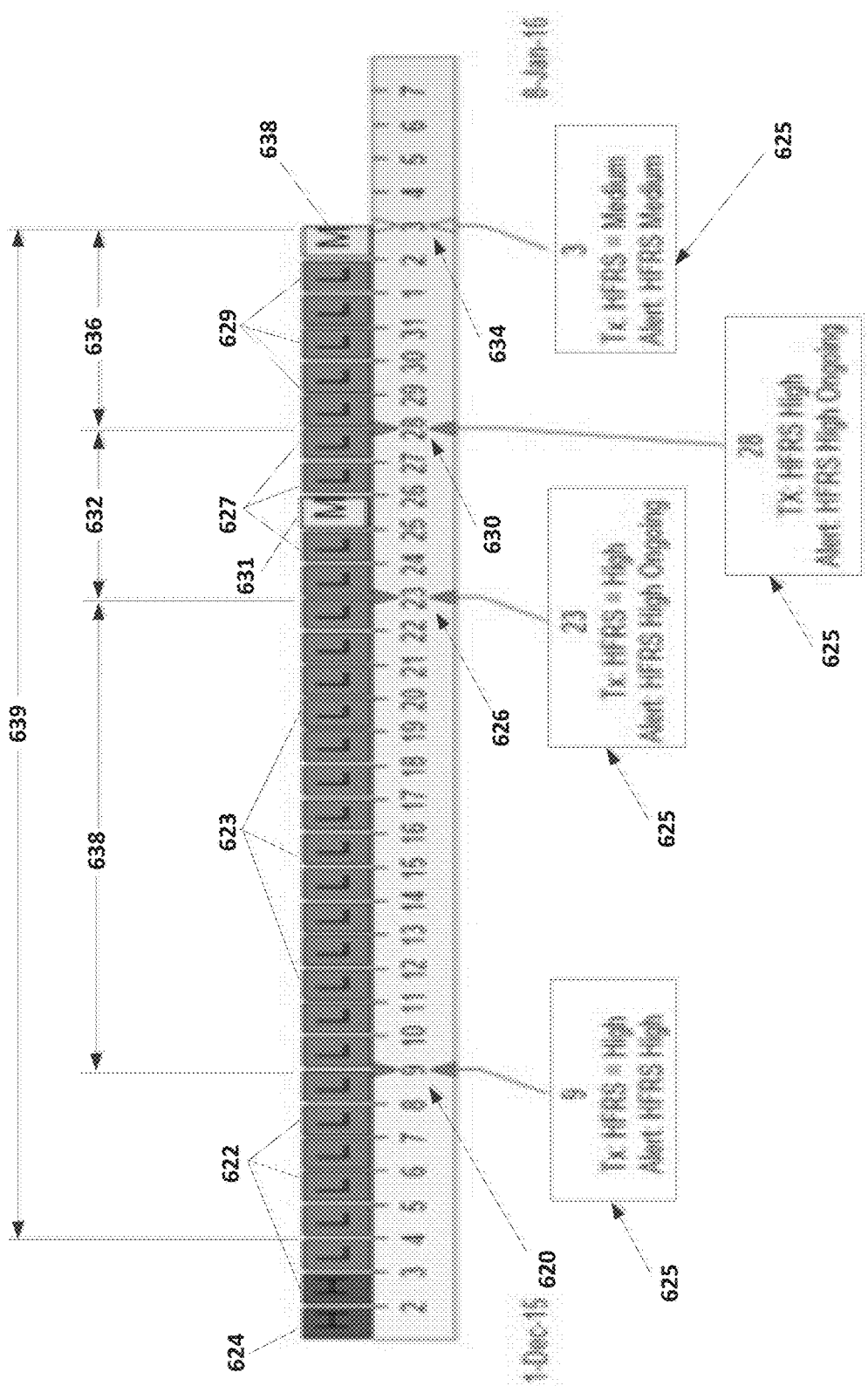

In the example illustrated in FIG. 13G, a data transmission 620 from a remote monitoring device, such as IMD 16 for example, was received by the external device 114 on Dec. 9, 2015. Upon receipt of the data transmission 620, one or more processor(s) 118 of external device 114 acquires patient metrics from the remote monitoring device and determines a daily HFRS 622 of either high H, medium M, or low L for each day during a time period extending subsequent to a previous transmission, or as in the example of FIG. 13G, subsequent to the date that the HFRS differentiation algorithm of the present disclosure was enabled in the external device 114, i.e., Dec. 1, 2015, to the day of receipt of the current data transmission 620, using the patient metric trends described above, for example.

External device 114 stores each daily HFRS 622 of either high H, medium M, or low L determined during the time period extending subsequent to a previous data transmission within memory 119. External device 114 then determines a maximum daily HFRS of each daily HFRS determined for each day within a lookback window occurring prior to receipt of the current data transmission 620. In one example, the lookback window may be a 30 day lookback window, or if it has been less than 30 days since the HFRS differentiation algorithm of the present disclosure was enabled in the external device 114, the lookback window extends back to the date that the HFRS differentiation algorithm was enabled, i.e., Dec. 1, 2015. In the example of FIG. 13G, the maximum daily HFRS is determined to be HFRS 624, which occurred on Dec. 1, 2015, and data transmission 620 is the first data transmission to be received by external device since the HFRS differentiation algorithm of the present disclosure was enabled on the external device 114, i.e., on Dec. 1, 2015. Since the maximum daily HFRS that occurred during the current lookback window was high H, the external device 114 determines that the HFRS for the current data transmission 620 is a high H HFRS. In addition, since nether an HFRS high alert or an HRFS high ongoing alert was generated during the lookback window associated with the current received data transmission 620, the external device 114 determines that a HFRS alert for the current data transmission 620 is a high HFRS alert. Therefore, the external device 114 generates and stores a display 625 associated with the current received data transmission 620 indicating one or both of the determination that the HFRS associated with the current received data transmission 620 is a high HFRS, "Current HFRS=High" and the HFRS alert associated with the current received data transmission 620 is high, "Alert: HFRS High", which may then be displayed by the external device 114 for subsequent review by a clinician.

After generating and storing display 625 associated with data transmission 620, external device 114 waits for receipt of a next data transmission from the remote monitoring device, which, in the example illustrated in FIG. 13G, is a data transmission 626 received on Dec. 23, 2015. Upon receipt of the next data transmission 626, the external device 114 determines a daily HFRS 623 of either high H, medium M, or low L for each day during a time period 628 subsequent to the previous data transmission 620 and up to the day of receipt of the current data transmission 626. In the example of FIG. 13G, upon receipt of the current data transmission 626, the external device 114 determines a daily HFRS of low L for each day during the time period 628 between the day of receipt of the previous received data transmission 620 and receipt of the current data transmission 624.

External device 114 stores each daily HFRS 623 of either high H, medium M, or low L determined during the time period 628 extending subsequent to a previous data transmission within memory 119. External device 114 then determines a maximum daily HFRS of each daily HFRS determined within a lookback window prior to the current received data transmission 626, as described above. In the example of FIG. 13G, since the maximum daily HFRS occurring within the lookback window associated with the current data transmission 626 is determined to be daily HFRS 624, which occurred on Dec. 1, 2015, a maximum daily HFRS of high H occurred during the current 30 day lookback window. Therefore, the external device 114 determines that the HFRS associated with the current received data transmission 626 is a high H HFRS. In addition, since an HFRS high alert was generated during the lookback window of the current received data transmission 626 for previously received data transmission 620, the external device 114 determines that a HFRS alert for the current received data transmission 626 is a high ongoing event alert. Therefore, the external device 114 generates and stores a display 625 associated with the current received data transmission 626 indicating one or both of the determination that the HFRS associated with the current received data transmission 626 is a high HFRS, "Current HFRS=High" and the HFRS alert associated with the current received data transmission 626 is a high ongoing alert, "Alert: HFRS High Ongoing", which may then be displayed by the external device 114 for subsequent review by a clinician.

After generating and storing the display 625 associated with received data transmission 626, external device 114 waits for receipt of a next data transmission from the remote monitoring device, which, in the example illustrated in FIG. 13G, is a data transmission 630 received on Dec. 28, 2015. Upon receipt of the next data transmission 630, the external device 114 determines a daily HFRS 627 of high H, medium M, or low L for each day during a time period 632 subsequent to the previous data transmission 626 up to receipt of the next data transmission 630.

External device 114 stores each daily HFRS 627 of either high H, medium M, or low L determined during the time period 632 extending subsequent to a previous data transmission within memory 119. External device 114 then determines a maximum daily HFRS of each daily HFRS determined for each day within a lookback window prior to the current received data transmission 630, as described above. Despite there being a medium M HFRS determined for daily HFRS 631 for the current received data transmission, because the high H HFRS that was determined for the data transmission 620 received on Dec. 1, 2015 is greater than daily HFRS 631, the maximum daily HFRS remains HFRS 624 and therefore a daily HFRS of high H is determined to have occurred during the current lookback window for the current received data transmission 630. Since the maximum daily HFRS is determined to high, H, the external device 114 determines that the HFRS for the current data transmission 630 is high H. In addition, since either an HFRS high alert or an HFRS high ongoing alert occurred for a previous received data transmission during the lookback window of the current received data transmission 630, i.e. data transmissions 620 and 626 respectively, the external device 114 determines that the an HFRS alert for the current received data transmission 630 is a high ongoing HFRS alert. Therefore, the external device 114 generates and stores a display 625 associated with the current received data transmission 630 indicating one or both of the determination that the HFRS associated with the current received data transmission 630 is a high HFRS, "Current HFRS=High" and the HFRS alert associated with the current received data transmission 630 is a high ongoing HFRS alert, "Alert: HFRS High Ongoing", which may then be displayed by the external device 114 for subsequent review by a clinician.

After generating and storing the display 625 associated with data transmission 630, external device 114 waits for receipt of a next data transmission from the remote monitoring device, which, in the example illustrated in FIG. 13G, is data transmission 634 received on Jan. 3, 2016. Upon receipt of the next data transmission 634, the external device 114 determines a daily HFRS 629 of either high H, medium M, or low L for each day during a time period 636 subsequent to the previous data transmission 630 and up to receipt of the current received data transmission 634.

External device 114 stores each daily HFRS 629 of either high H, medium M, or low L determined during the time period 636 extending subsequent to a previous data transmission within memory 119. External device 114 then determines a maximum daily HFRS of the daily HFRS determined for each day within a lookback window 639 prior to the current received data transmission 634, i.e., between Dec. 4, 2015-Jan. 3, 2016. In the example of FIG. 13G, the maximum daily HFRS was determined to be daily HFRS 638, which occurred on Jan. 2, 2016 (because in the example HFRS 638 is greater than HFRS 631) and was determined to be medium M. Therefore, the external device 114 determines that the HFRS for the current received data transmission 634 is a medium HFRS. In addition, since no HFRS medium alert or HFRS medium ongoing alert was determined during the lookback window 639, the external device 114 determines that an HFRS alert for the current data transmission 634 is a medium HFRS alert. Therefore, the external device 114 generates and stores a display 625 associated with the current received data transmission 634 indicating one or both of the determination that the HFRS associated with the current received data transmission 634 is a medium HFRS, "Current HFRS=Medium" and the HFRS alert associated with the current received data transmission 634 is a medium HFRS alert, "Alert: HFRS Medium", which may then be displayed by the external device 114 for subsequent review by a clinician.

In this way, by enabling the high and medium alerts generated by the external device 114 to be further differentiated as being either high alerts or high ongoing alerts, and by enabling further differentiation of an identified current HFRS status as high, high new, medium and medium new, the HFRS differentiation algorithm of the present disclosure may reduce the number of alerts needing to be evaluated by the clinician. For example, knowing whether an event is an ongoing event, not an ongoing event, a new high HFRS event, or not a new high HFRS event enables more efficient prioritization by the clinician.

Figure 14A:
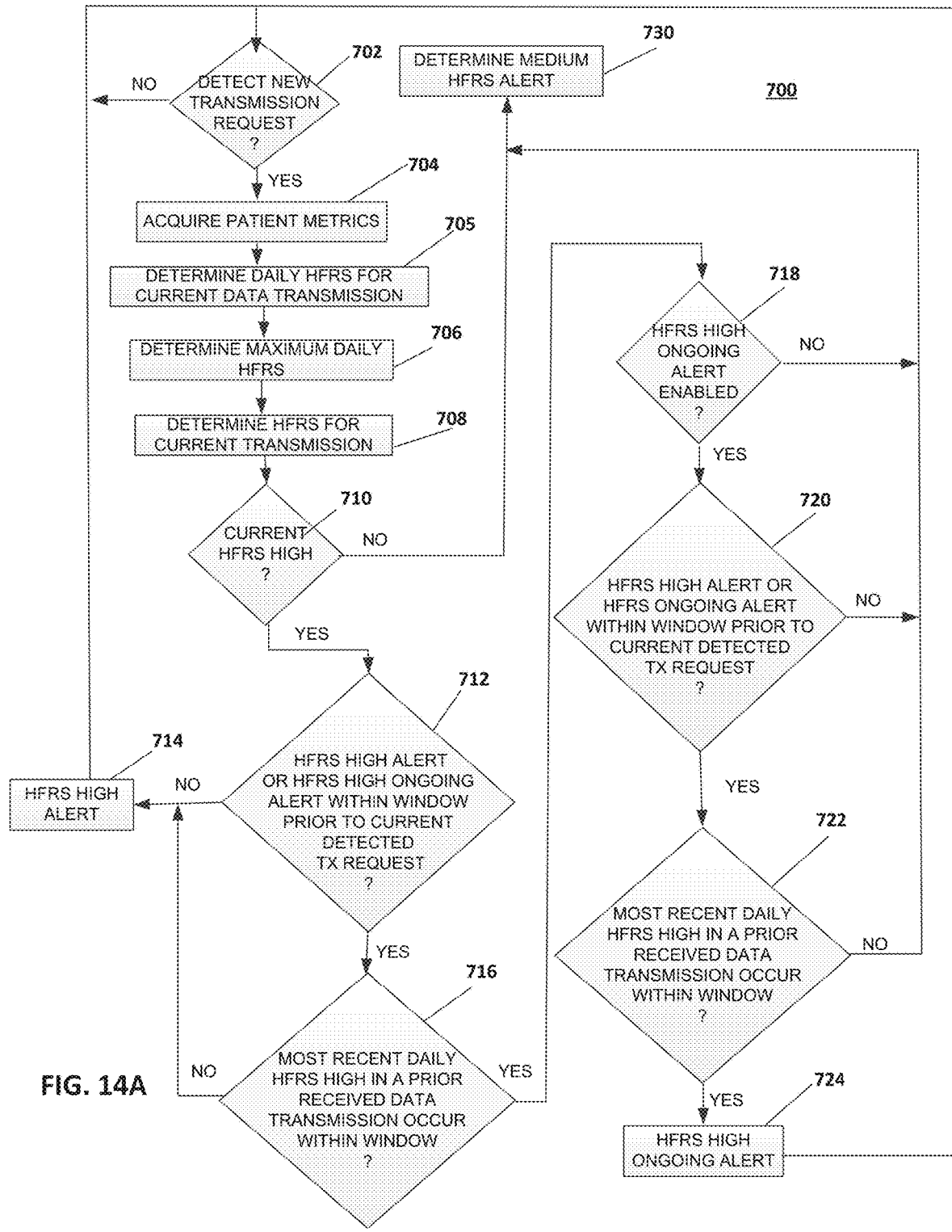
FIGS. 14A and 14B are flow diagrams of a method of differentiating determined heart failure risk status in a heart failure monitoring system, according to an example of the present disclosure.
Figure 14B:
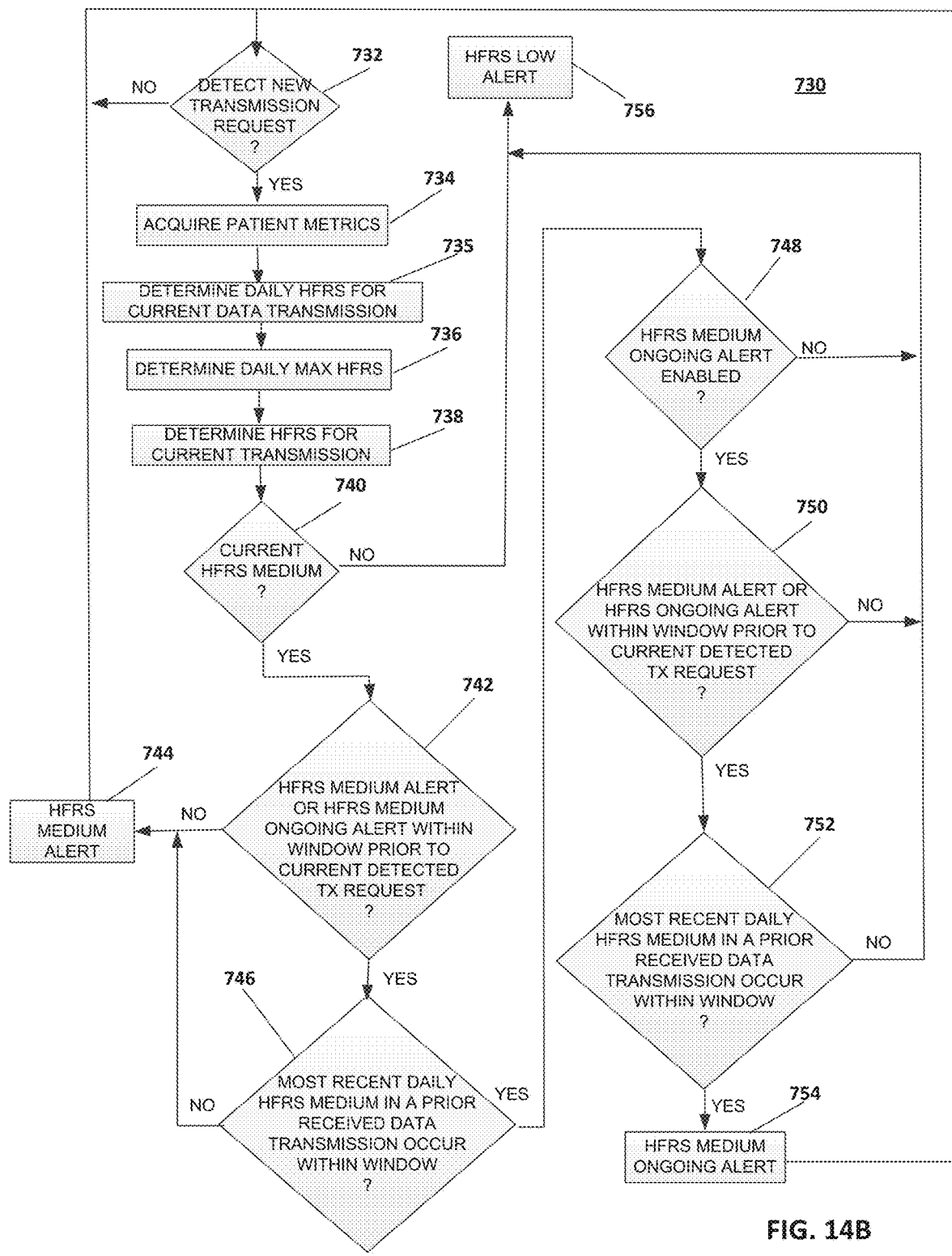

FIGS. 14A and 14B are flow diagrams of a method of differentiating determined heart failure risk score alerts in a heart failure monitoring system, according to an example of the present disclosure. As illustrated in FIG. 14A, in one example of a method of differentiating determined heart failure risk score alerts 700 in a heart failure monitoring system, one or more processor(s) 118 of external device 114 detect receipt of a new data transmission from the remote monitoring device, such as IMD 16 for example, Block 702. For example, data transmissions from the IMD 16 to the external device 114 may be initiated manually by the patient, may be automatic transmissions scheduled by the clinician to occur periodically, such as every three months, or every 30 days for example, or may be device initiated, such as in response to an increased impedance level, or a low battery indication for the device, for example. Upon detecting a new data transmission, the external devices 114 acquires patient metrics from the remote monitoring device, Block 704, determines a daily HFRS of either high H, medium M, or low L for each day during a time period extending subsequent to a previous data transmission based on the acquired patient metrics, Block 705, and determines a maximum daily HFRS during a lookback window from the current received data transmission, Block 706. An HFRS for the current received data transmission is then determined based on the determined maximum daily HFRS, Block 708.

Based on the HFRS for the current data transmission determined in Block 708, the external device 114 determines whether the HFRS for the current data transmission is a high HFRS, Block 710. If the HFRS for the current data transmission is a high HFRS, Yes in Block 710, the device determines whether an HFRS high alert or an HFRS ongoing alert was determined within the lookback window prior to the current received data transmission, Block 712. If an HFRS high alert or an HFRS ongoing alert was not determined within the lookback window prior to the current received data transmission, No in Block 712, the external device 114 determines that the HFRS alert for the current data transmission is a high alert, Block 714, and waits for the next received data transmission, Block 702. If an HFRS high alert or an HFRS high ongoing alert was determined within the lookback window prior to the current received data transmission, Yes in Block 712, the external device 114 determines whether the most recent day with a daily HFRS of high H in a prior transmission is included in the lookback window associated with the current data transmission, Block 716. If the most recent day with a daily HFRS of high H in a prior transmission is not included in the lookback window associated with the current data transmission, i.e., is greater than 30 days from the receipt of the current data transmission, No in Block 716, the external device 114 determines that the HFRS alert for the current data transmission is a high alert, Block 714, and waits for the next received data transmission, Block 702.

In this way, the external device 114 determines an HFRS high alert if the HFRS for the current data transmission is high (Yes in Block 710) and either no HFRS alert or HFRS high ongoing alert is determined within the lookback window prior to the current data transmission (No in Block 712), or an HFRS high alert or an HFRS high ongoing alert is determined within the lookback window prior to the current data transmission (Yes in Block 712), but the most recent day with a daily HFRS of high in a prior transmission is not included in the lookback window associated with the current data transmission, i.e., is greater than 30 days from the receipt of the current data transmission (No in Block 716).

If the most recent day with a daily HFRS of high H in a prior transmission is included in the lookback window associated with the current data transmission, i.e., is less than 30 days from the receipt of the current data transmission, Yes in Block 716, and therefore an HFRS high alert is not determined to occur, and if the HFRS high ongoing alert is enabled in the external device 114, Yes in Block 718, the external device 114 determines whether an HFRS high alert or an HFRS ongoing alert was determined to occur within the lookback window of the current received data transmission, Block 720. If an HFRS high alert or an HFRS ongoing alert was determined to occur within the lookback window of the current received data transmission, Yes in Block 720, the external device 114 determines whether the most recent day with a daily HFRS of high H in a prior transmission is included in the lookback window associated with the current data transmission, i.e., within than 30 days from the receipt of the current data transmission, Block 722. If the most recent day with a daily HFRS of high H in a prior transmission is included in the lookback window associated with the current data transmission, Yes in Block 722, the external device 114 determines that the HFRS alert for the current data transmission is a high ongoing alert, Block 724, and waits for the next received data transmission, Block 702.

According to an example illustrated in FIG. 14A, if the HFRS for the current data transmission is not a high HFRS, No in Block 710, the HFRS high ongoing alert is not enabled, No in Block 718, or if the HFRS alert for the current data transmission is not determined to be either a high alert or a high ongoing alert, No in Block 720 or Block 722, the external device 114 determines whether an HFRS medium alert or an HFRS medium ongoing alert is detected, Block 730, which is described below in FIG. 14B. According to another example, if the HFRS for the current data transmission is not a high HFRS, No in Block 710, the HFRS high ongoing alert is not enabled, No in Block 718, if an HFRS high alert or an HFRS high ongoing alert was not determined to occur within the lookback window of the current received data transmission, No in Block 720, or the most recent day with a daily HFRS of high H in a prior transmission is not included in the lookback window associated with the current data transmission, No in Block 722, the external device 114 may wait for the next received data transmission, Block 702.

In this way, the external device 114 determines an HFRS high ongoing alert, Block 724, if the HFRS for the current data transmission is high (Yes in Block 710), the high ongoing alert feature is enabled in the external device 114, (Yes in Block 718) and both an HFRS high alert or an HFRS ongoing alert was determined to occur within the lookback window of the current received data transmission, Yes in Block 720, and the most recent day with a daily HFRS of high H in a prior transmission is included in the lookback window associated with the current data transmission from the receipt of the current data transmission, Yes in Block 722.

As illustrated in FIG. 14B, in one example of a method of differentiating determined heart failure risk score alerts 730 in a heart failure monitoring system, one or more processor(s) 118 of external device 114 detect receipt of a new data transmission from the remote monitoring device, such as IMD 16 for example, Block 732. Upon detecting a new data transmission, the external devices 114 acquires patient metrics from the remote monitoring device, Block 734, determines a daily HFRS of either high H, medium M, or low L for each day during a time period extending subsequent to a previous data transmission based on the acquired patient metrics, Block 735, and determines a maximum daily high HFRS during a lookback window from the current received data transmission based on the acquired patient metrics, Block 736. An HFRS for the current received data transmission is then determined based on the determined maximum daily HFRS, Block 738.

Based on the HFRS for the current data transmission determined in Block 738, the external device 114 determines whether the HFRS for the current data transmission is a medium HFRS, Block 740. If the HFRS alert for the current data transmission is a medium HFRS, Yes in Block 740, the device determines whether an HFRS medium alert or an HFRS medium ongoing alert was determined within the lookback window prior to the current received data transmission, Block 742. If an HFRS medium alert or an HFRS medium ongoing alert was not determined within the lookback window prior to the current received data transmission, No in Block 742, the external device 114 determines that the HFRS for the current data transmission is a medium alert, Block 744, and waits for the next received data transmission, Block 732. If an HFRS medium alert or an HFRS medium ongoing alert was determined within the lookback window prior to the current received data transmission, Yes in Block 742, the external device 114 determines whether the most recent day with a daily HFRS of medium M in a prior transmission is included in the lookback window associated with the current data transmission, Block 746. If the most recent day with a daily HFRS of medium M in a prior transmission is not included in the lookback window associated with the current data transmission, i.e., is greater than 30 days from the receipt of the current data transmission, No in Block 746, the external device 114 determines that the HFRS for the current data transmission is a medium alert, Block 744, and waits for the next received data transmission, Block 732.

In this way, the external device 114 determines an HFRS medium alert if the HFRS for the current data transmission is medium (Yes in Block 740) and either no HFRS medium alert or HFRS medium ongoing alert is determined within the lookback window prior to the current data transmission (No in Block 742), or an HFRS medium alert or an HFRS medium ongoing alert is determined within the lookback window prior to the current data transmission (Yes in Block 742), but the most recent day with a daily HFRS of medium in a prior transmission is not included in the lookback window associated with the current data transmission, i.e., is greater than 30 days from the receipt of the current data transmission (No in Block 746).

If the most recent day with a daily HFRS of medium M in a prior transmission is included in the lookback window associated with the current data transmission, i.e., is less than 30 days from the receipt of the current data transmission, Yes in Block 746, and therefore an HFRS medium alert is not determined to occur, and if the HFRS medium ongoing alert is enabled in the external device 114, Yes in Block 748, the external device 114 determines whether an HFRS medium alert or an HFRS medium ongoing alert was determined to occur within the lookback window of the current received data transmission, Block 750. If an HFRS medium alert or an HFRS medium ongoing alert was determined to occur within the lookback window of the current received data transmission, Yes in Block 750, the external device 114 determines whether the most recent day with a daily HFRS of medium in a prior transmission is included in the lookback window associated with the current data transmission, i.e., within than 30 days from the receipt of the current data transmission, Block 752. If the most recent day with a daily HFRS of medium M in a prior transmission is included in the lookback window associated with the current data transmission, Yes in Block 752, the external device 114 determines that the HFRS alert for the current data transmission is a medium ongoing alert, Block 754, and waits for the next received data transmission, Block 732.

According to the example illustrated in FIG. 14B, if the HFRS for the current data transmission is not a medium HFRS, No in Block 740, the HFRS medium ongoing alert is not enabled, No in Block 748, or if the HFRS alert for the current data transmission is not determined to be either a medium alert or a medium ongoing alert, No in Block 750 or Block 752, the external device 114 determines that an HFRS low alert is detected, Block 756. According to another example, if the HFRS for the current data transmission is not a medium HFRS, No in Block 740, the HFRS medium ongoing alert is not enabled, No in Block 748, if the HFRS alert for the current data transmission is not determined to be either a medium alert or a medium ongoing alert, No in Block 750, or the most recent day with a daily HFRS of medium M in a prior transmission is not included in the lookback window associated with the current data transmission, No in Block 752, the external device 114 may wait for the next received data transmission, Block 732.

In this way, the external device 114 determines an HFRS medium ongoing alert, Block 754, if the HFRS for the current data transmission is medium (Yes in Block 740), the medium ongoing alert feature is enabled in the external device 114, (Yes in Block 748) and both an HFRS medium alert or an HFRS medium ongoing alert was determined to occur within the lookback window of the current received data transmission, Yes in Block 750, and the most recent day with a daily HFRS of medium M in a prior transmission is included in the lookback window associated with the current data transmission from the receipt of the current data transmission, Yes in Block 752.

The techniques described herein describe techniques for enabling the high and medium alerts generated by the external monitoring device to be further differentiated as being either alerts or ongoing alerts, and, in some examples, by enabling further differentiation of an identified current heart failure risk score ("HFRS") status as high, high new, medium and medium new. Such additional HFRS differentiation of the present disclosure may assist in prioritization of patients, determining patient conditions, assessing the effectiveness of a current therapy, and determining whether therapy adjustments may be necessary. For example, during monitoring of patients, knowing whether an event is an ongoing event, not an ongoing event, a new event, or not a new event enables more efficient prioritization and treatment of patients by the clinician.

Various examples have been described that include detecting and storing patient metrics and transmitting high and lower resolution diagnostic data from an IMD. These examples include techniques for identifying patients with an elevated risk of being re-hospitalized due to heart failure. In addition, an alert of patient risk levels may be remotely delivered to a healthcare professional from multiple different patients for triage and earlier diagnosis and treatment of heart failure before re-hospitalization. Any combination of detection and notification of heart failure risk level is contemplated. These and other examples are within the scope of the following claims.

The invention claimed is:

1. A method of differentiating heart failure risk scores in a heart failure monitoring device, comprising:
   receiving, at the monitoring device, a current data transmission from a remote monitoring device;
   acquiring patient metrics from the remote monitoring device;
   determining a daily heart failure risk score for each day occurring during a time period from a previous received data transmission to the current data transmission based on the acquired patient metrics;
   determining a maximum daily heart failure risk score of the determined daily heart failure risk scores during a lookback window prior to receipt of the current data transmission;
   determining a heart failure risk score for the current data transmission based on the determined maximum daily heart failure risk score;
   determining a heart failure risk score alert for the current data transmission based on whether the heart failure risk score for the current data transmission matches a prior heart failure risk score determined during the lookback window prior to receipt of the current data transmission; and
   generating a display of at least one of the determined heart failure risk score for the current data transmission and the determined heart failure risk score alert.

2. The method of claim 1, wherein the determined heart failure risk score for the current data transmission comprises one of a high heart failure risk score, a medium heart failure risk score, and a low heart failure risk score.

3. The method of claim 2, further comprising:
   determining, in response to the determined heart failure risk score for the current data transmission being high, whether a high alert or a high ongoing alert was determined within the lookback window prior to receipt of the current data transmission; and
   determining that the heart failure risk score alert for the current data transmission is a high alert in response to the high alert or the high ongoing alert not being determined within the lookback window prior to receipt of the current data transmission.

4. The method of claim 3, further comprising waiting for a next received data transmission in response to at least one of the determined heart failure risk score for the current data transmission not being high, the high ongoing alert not being enabled, a high alert or a high ongoing alert was not determined to occur within the lookback window prior to receipt of the current data transmission, or the most recent day with a daily heart failure risk score of high in a prior transmission is not included within the lookback window prior to receipt of the current data transmission.

5. The method of claim 3, further comprising determining a high heart failure risk score alert in response to at least one of the determined heart failure risk score for the current data transmission not being high, the high ongoing alert not being enabled, a high alert or a high ongoing alert not being determined to occur within the lookback window prior to receipt of the current data transmission, or the most recent day with a daily heart failure risk score of high in a prior transmission not being included within the lookback window prior to receipt of the current data transmission.

6. The method of claim 3, further comprising:
  determining, in response to the determined heart failure risk score for the current data transmission being high, whether a high alert or a high ongoing alert was determined within the lookback window prior to receipt of the current data transmission;
  determining, in response to the high alert or the high ongoing alert being determined within the lookback window prior to receipt of the current data transmission, whether the most recent day with a daily heart failure risk score of high in a prior transmission is included within the lookback window prior to receipt of the current data transmission; and
  determining that the heart failure risk score alert for the current data transmission is a high alert in response to the most recent day with a daily heart failure risk score of high in a prior transmission not being included within the lookback window prior to receipt of the current data transmission.

7. The method of claim 1, further comprising:
  determining, in response to the determined heart failure risk score for the current data transmission being medium, whether a medium alert or a medium ongoing alert was determined within the lookback window prior to receipt of the current data transmission; and
  determining that the heart failure risk score for the current data transmission is a medium alert in response to a medium alert or a medium ongoing alert not being determined within the lookback window prior to receipt of the current data transmission.

8. The method of claim 7, further comprising waiting for a next received data transmission in response to at least one of the determined heart failure risk score for the current data transmission not being medium, the medium ongoing alert not being enabled, a medium alert or a medium ongoing alert was not determined to occur within the lookback window prior to receipt of the current data transmission, or the most recent day with a daily heart failure risk score of medium in a prior transmission is not included within the lookback window prior to receipt of the current data transmission.

9. The method of claim 7, further comprising determining a medium heart failure risk score alert in response to at least one of the determined heart failure risk score for the current data transmission not being medium, the medium ongoing alert not being enabled, a medium alert or a medium ongoing alert not being determined to occur within the lookback window prior to receipt of the current data transmission, or the most recent day with a daily heart failure risk score of medium in a prior transmission not being included within the lookback window prior to receipt of the current data transmission.

10. The method of claim 7, further comprising:
  determining, in response to the determined heart failure risk score for the current data transmission being medium, whether a medium alert or a medium ongoing alert was determined within the lookback window of the current data transmission;
  determining, in response to the medium alert or the medium ongoing alert being determined within the lookback window prior to receipt of the current data transmission, whether the most recent day with a daily heart failure risk score of medium in a prior transmission is included within the lookback window prior to receipt of the current data transmission; and
  determining that the heart failure risk score alert for the current data transmission is a medium alert in response to the most recent day with a daily heart failure risk score of medium in a prior transmission not being included within the lookback window prior to receipt of the current data transmission.

11. The method of claim 1, further comprising:
  determining whether the maximum daily heart failure risk score occurred during the time window prior to receipt of the current data transmission; and
  determining the heart failure risk score as being new in response to determining the maximum daily heart failure risk score occurred during the time window prior to receipt of the current data transmission.

12. An external monitoring device for differentiating heart failure risk scores of a patient, comprising:
  an input/output device to receive a current data transmission and acquire patient metrics from a remote monitoring device; and
  one or more processors configured to:
    determine a daily heart failure risk score for each day occurring during a time period from a previous received data transmission to the current data transmission based on the acquired patient metrics;
    determine a maximum daily heart failure risk score of the determined daily heart failure risk scores during a lookback window prior to the current data transmission;
    determine a heart failure risk score for the current data transmission based on the determined maximum daily heart failure risk score;
    determine a heart failure risk score alert for the current data transmission based on whether the determined heart failure risk score for the current data transmission matches a prior heart failure risk score determined during the lookback window prior to the current data transmission; and
    generate a display of at least one of the determined heart failure risk score for the current data transmission and the determined heart failure risk score alert to be output by the input/output device.

13. The device of claim 12, wherein the determined heart failure risk score for the current data transmission comprises one of a high heart failure risk score, a medium heart failure risk score, and a low heart failure risk score.

14. The device of claim 12, wherein the one or more processors are further configured to:
  determine, in response to the determined heart failure risk score for the current data transmission being high, whether a high alert or a high ongoing alert was determined within the lookback window prior to receipt of the current data transmission; and determine that the heart failure risk score alert for the current data transmission is a high alert in response to the high alert or the high ongoing alert not being determined within the lookback window prior to receipt of the current data transmission.

15. The device of claim 14, wherein the one or more processors are further configured to wait for a next received data transmission in response to at least one of the determined heart failure risk score for the current data transmission not being high, the high ongoing alert not being enabled, a high alert or a high ongoing alert was not determined to occur within the lookback window of the current data transmission, or the most recent day with a daily heart failure risk score of high in a prior transmission is not included within the lookback window prior to receipt of the current data transmission.

16. The device of claim 14, wherein the one or more processors are further configured to determine a high heart failure risk score alert in response to at least one of the determined heart failure risk score for the current data transmission not being high, the high ongoing alert not being enabled, a high alert or a high ongoing alert not being determined to occur within the lookback window prior to receipt of the current data transmission, or the most recent day with a daily heart failure risk score of high in a prior transmission not being included within the lookback window prior to receipt of the current data transmission.

17. The device of claim 14, wherein the one or more processors are further configured to:
   determine, in response to the determined heart failure risk score for the current data transmission being high, whether a high alert or a high ongoing alert was determined within the lookback window prior to receipt of the current data transmission;
   determine, in response to the high alert or the high ongoing alert being determined within the lookback window prior to receipt of the current data transmission, whether the most recent day with a daily heart failure risk score of high in a prior transmission is included within the lookback window prior to receipt of the current data transmission; and
   determine that the heart failure risk score alert for the current data transmission is a high alert in response to the most recent day with a daily heart failure risk score of high in a prior transmission not being included within the lookback window prior to receipt of the current data transmission.

18. The device of claim 12, wherein the one or more processors are further configured to:
   determine, in response to the determined heart failure risk score for the current data transmission being medium, whether a medium alert or a medium ongoing alert was determined within the lookback window prior to receipt of the current data transmission; and
   determine that the heart failure risk score for the current data transmission is a medium alert in response to a medium alert or a medium ongoing alert not being determined within the lookback window prior to receipt of the current data transmission.

19. The device of claim 18, wherein the one or more processors are further configured to wait for a next received data transmission in response to at least one of the determined heart failure risk score for the current data transmission not being medium, the medium ongoing alert not being enabled, a medium alert or a medium ongoing alert was not determined to occur within the lookback window prior to receipt of the current data transmission, or the most recent day with a daily heart failure risk score of medium in a prior transmission is not included within the lookback window prior to receipt of the current data transmission.

20. The device of claim 18, wherein the one or more processors are further configured to determine a low heart failure risk score alert in response to at least one of the determined heart failure risk score for the current data transmission not being medium, the medium ongoing alert not being enabled, a medium alert or a medium ongoing alert not being determined to occur within the lookback window prior to receipt of the current data transmission, or the most recent day with a daily heart failure risk score of medium in a prior transmission not being included within the lookback window prior to receipt of the current data transmission.

21. The device of claim 18, wherein the one or more processors are further configured to:
   determine, in response to the determined heart failure risk score for the current data transmission being medium, whether a medium alert or a medium ongoing alert was determined within the lookback window prior to receipt of the current data transmission;
   determine, in response to the medium alert or the medium ongoing alert being determined within the lookback window prior to receipt of the current data transmission, whether the most recent day with a daily heart failure risk score of medium in a prior transmission is included within the lookback window prior to receipt of the current data transmission; and
   determine that the heart failure risk score alert for the current data transmission is a medium alert in response to the most recent day with a daily heart failure risk score of medium in a prior transmission not being included within the lookback window prior to receipt of the current data transmission.

22. The device of claim 12, wherein the one or more processors are further configured to:
   determine whether the maximum daily heart failure risk score occurred during the time window prior to receipt of the current data transmission; and
   determine the heart failure risk score as being new in response to determining the maximum daily heart failure risk score occurred during the time window prior to receipt of the current data transmission.

23. An implantable medical device monitoring system comprising:
   an implantable medical device to sense a cardiac signal of a patient and monitor heart failure patient metrics of the patient in response to the sensed cardiac signal;
   an external device to differentiate heart failure risk scores of the patient, comprising:
      an input/output device to receive a current data transmission and acquire patient metrics from the implantable medical device; and
      one or more processors configured to:
         determine a daily heart failure risk score for each day occurring during a time period from a previous received data transmission to the current data transmission based on the acquired patient metrics;
         determine a maximum daily heart failure risk score of the determined daily heart failure risk scores during a lookback window prior to the current data transmission;

determine a heart failure risk score for the current data transmission based on the determined maximum daily heart failure risk score;

determine a heart failure risk score alert for the current data transmission based on whether the determined heart failure risk score for the current data transmission matches a prior heart failure risk score determined during the lookback window prior to the current data transmission; and generate a display of at least one of the determined heart failure risk score for the current data transmission and the determined heart failure risk score alert to be output by the input/output device.

24. A method of differentiating heart failure risk score in a heart failure monitoring device, comprising:

receiving, at the monitoring device, a current data transmission and acquired patient metrics from a remote monitoring device;

determining a daily heart failure risk score for each day occurring during a time period from a previous received data transmission to the current data transmission based on the acquired patient metrics;

determining a maximum daily heart failure risk score of the determined daily heart failure risk scores during a lookback window prior to receipt of the current data transmission;

determining a heart failure risk score for the current data transmission based on the determined maximum daily heart failure risk score;

determining a heart failure risk score alert for the current data transmission based on whether the determined heart failure risk score for the current data transmission matches a prior heart failure risk score determined during the lookback window prior to receipt of the current data transmission; and generating a display of at least one of the determined heart failure risk score for the current data transmission and the determined heart failure risk score alert.

* * * * *